US008172826B2

(12) United States Patent
Hyde et al.

(10) Patent No.: US 8,172,826 B2
(45) Date of Patent: May 8, 2012

(54) DEVICE FOR ACTIVELY REMOVING A TARGET CELL FROM BLOOD OR LYMPH OF A VERTEBRATE SUBJECT

(75) Inventors: Roderick A. Hyde, Redmond, WA (US); Muriel Y. Ishikawa, Livermore, CA (US); Edward K. Y. Jung, Bellevue, WA (US); Robert Langer, Newton, MA (US); Eric C. Leuthardt, St. Louis, MO (US); Nathan P. Myhrvold, Bellevue, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 121 days.

(21) Appl. No.: 12/802,854

(22) Filed: Jun. 14, 2010

(65) Prior Publication Data

US 2010/0255057 A1    Oct. 7, 2010

Related U.S. Application Data

(63) Continuation of application No. 12/660,928, filed on Mar. 5, 2010, and a continuation-in-part of application No. 12/660,926, filed on Mar. 5, 2010, and a continuation-in-part of application No. 12/380,400, filed on Feb. 25, 2009, and a continuation-in-part of application No. 12/380,399, filed on Feb. 25, 2009.

(51) Int. Cl.
*A61M 31/00*    (2006.01)
(52) U.S. Cl. ...................................... 604/500
(58) Field of Classification Search ............... 604/891.1, 604/4.01, 65, 66, 28, 27, 500; 600/309, 439; 424/140.1, 422
See application file for complete search history.

(56) References Cited

U.S. PATENT DOCUMENTS 4,955,857 A    9/1990 Shettigar
(Continued)

FOREIGN PATENT DOCUMENTS

EP    1 550 454 A1    7/2005

OTHER PUBLICATIONS

Ng, David C. et al.; Real time in vivo imaging and measurement of serine protease activity in the mouse hippocampus using a dedicated complementary metal-oxide semiconductor imaging device; Journal of Neuroscience Methods; 2006; pp. 23-30; vol. 156; Elsevier B.V.

(Continued)

*Primary Examiner* — Christopher D Koharski

(57) ABSTRACT

Devices, systems, and methods are described herein for controlling the level of one or more target cell types in the blood fluid and/or lymph fluid of a vertebrate subject. Devices and systems are provided that include a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate a physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor.

55 Claims, 5 Drawing Sheets

U.S. PATENT DOCUMENTS

| | | | |
|---|---|---|---|
| 5,092,886 | A | 3/1992 | Dobos-Hardy |
| 5,107,422 | A | 4/1992 | Kamentsky et al. |
| 5,281,199 | A | 1/1994 | Ensminger et al. |
| 5,411,551 | A | 5/1995 | Winston et al. |
| 5,474,772 | A | 12/1995 | Maddock |
| 5,790,691 | A | 8/1998 | Narayanswamy et al. |
| 5,804,563 | A | 9/1998 | Still et al. |
| 5,831,012 | A | 11/1998 | Nilsson et al. |
| 6,030,653 | A | 2/2000 | Rosenthal |
| 6,190,691 | B1 | 2/2001 | Mak |
| 6,240,312 | B1 | 5/2001 | Alfano et al. |
| 6,255,461 | B1 | 7/2001 | Mosbach et al. |
| 6,287,516 | B1 | 9/2001 | Matson et al. |
| 6,425,867 | B1 | 7/2002 | Vaezy et al. |
| 6,471,872 | B2 | 10/2002 | Kitaevich et al. |
| 6,670,427 | B1 | 12/2003 | Ulbricht et al. |
| 6,673,596 | B1 | 1/2004 | Sayler et al. |
| 6,733,471 | B1 | 5/2004 | Ericson et al. |
| 6,797,522 | B1 | 9/2004 | Still et al. |
| 6,956,961 | B2 | 10/2005 | Cong et al. |
| 7,097,662 | B2 | 8/2006 | Evans, III et al. |
| 7,151,847 | B2 | 12/2006 | Vaisberg et al. |
| 7,244,232 | B2 | 7/2007 | Connelly et al. |
| 7,264,794 | B2 | 9/2007 | Georgakoudi et al. |
| 7,303,875 | B1 | 12/2007 | Bock et al. |
| 7,319,038 | B2 | 1/2008 | Southard |
| 7,326,240 | B1 | 2/2008 | Caro et al. |
| 7,355,334 | B2 | 4/2008 | Anazawa et al. |
| 7,413,846 | B2 | 8/2008 | Maloney et al. |
| 7,415,359 | B2 | 8/2008 | Hill et al. |
| 7,892,766 | B2 | 2/2011 | King et al. |
| 8,000,784 | B2 | 8/2011 | Ferren et al. |
| 2002/0034757 | A1 | 3/2002 | Cubicciotti |
| 2003/0231981 | A1 | 12/2003 | Johnson et al. |
| 2004/0018508 | A1 | 1/2004 | Friedman |
| 2004/0191246 | A1 | 9/2004 | Connelly et al. |
| 2004/0218724 | A1 | 11/2004 | Chornenky et al. |
| 2005/0121411 | A1 | 6/2005 | Cohen |
| 2005/0126916 | A1 | 6/2005 | Lockard et al. |
| 2005/0221529 | A1 | 10/2005 | Bang et al. |
| 2005/0251347 | A1 | 11/2005 | Perona et al. |
| 2005/0272974 | A1 | 12/2005 | Iddan |
| 2006/0039593 | A1 | 2/2006 | Sammak et al. |
| 2006/0083716 | A1 | 4/2006 | Kaufman et al. |
| 2006/0183223 | A1 | 8/2006 | King et al. |
| 2006/0234369 | A1 | 10/2006 | Sih |
| 2007/0021927 | A1 | 1/2007 | Ishikawa et al. |
| 2007/0066929 | A1* | 3/2007 | Ferren et al. ............ 604/8 |
| 2007/0066939 | A1 | 3/2007 | Krulevitch et al. |
| 2007/0083333 | A1 | 4/2007 | Vitiello et al. |
| 2007/0093739 | A1 | 4/2007 | Brady et al. |
| 2007/0156211 | A1 | 7/2007 | Ferren et al. |
| 2007/0178084 | A1 | 8/2007 | King et al. |
| 2007/0225633 | A1* | 9/2007 | Ferren et al. ............ 604/27 |
| 2007/0225634 | A1 | 9/2007 | Ferren et al. |
| 2007/0276208 | A1 | 11/2007 | Connelly et al. |
| 2007/0294150 | A1 | 12/2007 | Jung et al. |
| 2008/0058785 | A1 | 3/2008 | Boyden et al. |
| 2008/0201122 | A1 | 8/2008 | Kelly et al. |
| 2008/0275376 | A1 | 11/2008 | Howell et al. |
| 2008/0281400 | A1 | 11/2008 | Philipp et al. |
| 2009/0022768 | A1 | 1/2009 | King et al. |
| 2009/0054908 | A1 | 2/2009 | Zand et al. |
| 2009/0093728 | A1 | 4/2009 | Hyde et al. |
| 2010/0167372 | A1 | 7/2010 | King et al. |
| 2010/0185134 | A1 | 7/2010 | Houwen et al. |

OTHER PUBLICATIONS

Alexander et al.; "Molecular imprinting science and technology: a survey of the literature for the years up to and including 2003"; Journal of Molecular Recognition; 2006; pp. 106-180; vol. 19; John Wiley & Sons, Ltd.

Ammor, Mohammed Salim; "Recent Advances in the Use of Intrinsic Fluorescence for Bacterial Identification and Characterization"; J Fluoresc; 2007; pp. 1-5; Springer-Science + Business Media LLC.

An, Gary; "Theoretical Biology and Medical Modelling"; 2008; pp. 1-20; vol. 5, No. 11; BioMed Central Ltd.

Anderson et al.; "Inactivation of Food-Borne Enteropathogenic Bacteria and Spoilage Fungi Using Pulsed-Light"; IEEE Transactions on Plasma Science; Feb. 2000; pp. 83-88; vol. 28, No. 1; IEEE.

Baddour et al.; "High Frequency Ultrasound Imaging of Changes in Cell Structure Including Apoptosis"; IEEE Ultrasonics Symposium-1639; 2002; 6 pgs.; IEEE.

Békássy, Zoltán; "Long-Term Follow-Up of Cervical Intraepithelial Neoplasia Treated with Minimal Conization by Carbon Dioxide Laser"; Lasers in Surgery and Medicine; 1997; pp. 461-466; vol. 20; Wiley-Liss, Inc.

Bellin et al.; "Polymeric triple-shape materials"; PNAS; Nov. 28, 2006; pp. 18043-18047; vol. 103, No. 48; The National Academy of Sciences of the USA.

Bezrouk et al.; "Temperature Characteristics of Nitinol Spiral Stents"; Scripta Medica (BRNO); Oct. 2005; pp. 219-226; vol. 78, No. 4.

Bins et al.; "Texture of White Blood Cells Expressed by the Counting Densitogram"; Cytometry; 1981; pp. 321-324; vol. 1, No. 5; Society for Analytical Cytology.

Bouchard et al.; "Optical characterization of *Pseudomonas fluorescens* on meat surfaces using time-resolved fluorescence"; Journal of Biomedical Optics; Jan./Feb. 2006; pp. 0140011-1-0140011-7; vol. 11, No. 1; Society of Photo-Optical Instrumentation Engineers.

Cao et al.; "Molecular Beacon Aptamers for Protein Monitoring in Real-Time and in Homogeneous Solutions"; Current Proteomics; 2005; pp. 31-40; vol. 2, No. 1; Bentham Science Publishers Ltd.

Chan et al.; "Bactericidal effects of different laser wavelengths on periodontopathic germs in photodynamic therapy"; Lasers Med Sci; 2003; pp. 51-55; vol. 18; Springer-Verlag London Limited.

Chen et al.; Aptamer from whole-bacterium SELEX as new therapeutic reagent against virulent *Mycobacterium tuberculosis*; Biochemical and Biophysical Research Communications; 2007; pp. 743-748; vol. 357; Elsevier Inc.

Chung et al.; "Size Comparisons among Integral Membrane Transport Protein Homologues in *Bacteria, Archaea*, and *Eucarya*"; Journal of Bacteriology; Feb. 2001; pp. 1012-1021; vol. 183, No. 3; American Society for Microbiology.

"Complete Blood Count (CBC)"; WebMD; 7 pgs.; located at http://www.webmd.com/a-to-z-guides/complete-blood-count-cbc; by Caroline Rea, last updated Sep. 12, 2008.

Crawford et al.; "Peptide aptamers: Tools for biology and drug discovery"; Briefings in Functional Genomics and Proteomics; Apr. 2003; pp. 72-79; vol. 2, No. 1; Henry Stewart Publications.

Cristofanilli et al.; "Circulating Tumor Cells, Disease Progression, and Survival in Metastatic Breast Cancer"; The New England Journal of Medicine; Aug. 19, 2004; pp. 781-791; vol. 351, No. 8; Massachusetts Medical Society.

Davies, Michael J.; "Singlet oxygen-mediated damage to proteins and its consequences"; Biochemical and Biophysical Research Communications; 2003; pp. 761-770; vol. 305; Elsevier Science (USA).

Dehio, Christoph; "Infection-associated type IV secretion systems of *Bartonella* and their diverse roles in host cell interaction"; Cellular Microbiology; 2008; pp. 1591-1598; vol. 10, No. 8; Blackwell Publishing Ltd.

Dempster et al.; "Using Granulometries in Processing Images of Malarial Blood"; IEEE Xplore; 2001; pp. V-291-V-294; IEEE.

Desimone et al.; "Bactericidal Effect of 0.95-mW Helium-Neon and 5-mW Indium-Gallium-Aluminum-Phosphate Laser Irradiation at Exposure Times of 30, 60, and 120 Seconds on Photosensitized *Staphylococcus aureus* and *Pseudomonas aeruginosa* In Vitro"; Physical Therapy; Sep. 1999; pp. 839-846; vol. 79, No. 9; American Physical Therapy Association.

Doornbos et al.; "White Blood Cell Differentiation Using a Solid State Flow Cytometer"; Cytometry; 1993; pp. 589-594; vol. 14; Wiley-Liss, Inc.

Durick et al.; "Cellular biosensors for drug discovery"; Biosensors & Bioelectronics; 2001; pp. 587-592; vol. 16; Elsevier Science B.V.

Fan et al.; "Sensitive optical biosensors for unlabeled targets: A review"; Analytica Chimica Acta; 2008; pp. 8-26; vol. 620; Elsevier B.V.

Fei-Fei et al.; "One-Shot Learning of Object Categories"; IEEE Transactions on Pattern Analysis and Machine Intelligence; Apr. 2006; pp. 594-611; vol. 28, No. 4; IEEE Computer Society.

Fizazi et al.; "High detection rate of circulating tumor cells in blood of patients with prostate cancer using telomerase activity"; Annals of Oncology; 2007; pp. 518-521; vol. 18, No. 3; European Society for Medical Oncology.

Flatmark et al.; "Immunomagnetic Detection of Micrometastatic Cells in Bone Marrow of Colorectal Cancer Patients"; Clinical Cancer Research; Feb. 2002; pp. 444-449; vol. 8.

Francisco et al.; "Production and fluorescence-activated cell sorting of *Escherichia coli* expressing a functional antibody fragment on the external surface"; Proc. Natl. Acad. Sci. USA; Nov. 1993; pp. 10444-10448; vol. 90.

Gao et al.; "A Micro Sensing Probe for Detecting Individual Biological Cells"; Proceedings of the 25th Annual International Conference of the IEEE EMBS; Cancun, Mexico; Sep. 17-21, 2003; pp. 3348-3351.

Gibson et al.; "Ten-year experience of carbon dioxide laser ablation as treatment for cutaneous recurrence of malignant melanoma"; British Journal of Surgery; 2004; pp. 893-895; vol. 91; John Wiley & Sons Ltd.

Green et al.; "Disinfection of selected *Aspergillus* spp. using ultraviolet germicidal irradiation"; Can. J. Microbiol; 2004; pp. 221-224; vol. 50; NRC Canada.

Grönqvist et al; "Bactericidal Effect of Pulsed 1,064 nm Nd:YAG Laser Light on *Staphylococcus epidermidis* Is of Photothermal Origin: An In Vitro Study"; Lasers in Surgery and Medicine; 2000; pp. 336-340; vol. 27; Wiley-Liss, Inc.

Guffey et al.; "Effects of Combined 405-nm and 880-nm Light on *Staphylococcus aureus* and *Pseudomonas aeruginosa* In Vitro"; Photomedicine and Laser Surgery; 2006; pp. 680-683; vol. 24, No. 6; Mary Ann Liebert, Inc.

Hamblin et al.; "Rapid Control of Wound Infections by Targeted Photodynamic Therapy Monitored by In Vivo Bioluminescence Imaging"; Photochemistry and Photobiology; 2002; pp. 51-57; vol. 75, No. 1.

Hancock et al.; "Megawatt, Pulsed Ultraviolet Photon Sources for Microbial Inactivation"; IEEE Transactions on Plasma Science; Oct. 2004; pp. 2026-2031; vol. 32, No. 5; IEEE.

Hansen et al.; "Transbronchial laser ablation of benign and malignant tumors"; Minimally Invasive Therapy; 2006; pp. 4-8; vol. 15, No. 1; Taylor & Francis.

Heath et al.; "Antibody-targeted liposomes: Increase in specific toxicity of methotrexate-γ-aspartate"; Proc. Natl. Acad. Sci. USA; Mar. 1983; pp. 1377-1381; vol. 80.

He et al.; "In vivo quantitation of rare circulating tumor cells by multiphoton intravital flow cytometry"; PNAS; Jul. 10, 2007; pp. 11760-11765; vol. 104, No. 28; The National Academy of Sciences of the USA.

Ho et al.; "Isolation of anti-CD22 Fv with high affinity by Fv display on human cells"; PNAS; Jun. 20, 2006; pp. 9637-9642; vol. 103, No. 25.

Horata et al.; "Sequence variation of PfEMPI-DBLα in association with rosette formation in *Plasmodium falciparum* isolates causing severe and uncomplicated malaria"; Malaria Journal; 2009; pp. 1-11; vol. 8, No. 184; BioMed Central Ltd.

Horne et al.; "Which White Blood Cell Subtypes Predict Increased Cardiovascular Risk?"; Journal of the American College of Cardiology; 2005; pp. 1638-1643; vol. 45, No. 10; Elsevier Inc.

Hu et al.; "Preparation of a biochip on porous silicon and application for label-free detection of small molecule-protein interactions"; Rapid Communications in Mass Spectrometry; 2007; pp. 1277-1281; vol. 21; John Wiley & Sons, Ltd.

Jaiswal et al.; "Long-term multiple color imaging of live cells using quantum dot bioconjugates"; Nature Biotechnology; Jan. 2003; pp. 47-51; vol. 21; Nature Publishing Group.

Jawhara et al.; "Monitoring of bactericidal action of laser by in vivo imaging of bioluminescent *E. coli* in a cutaneous wound infection"; Lasers Med Sci; 2006; pp. 153-159; vol. 21; Springer-Verlag London Limited.

Jayasena, Sumedha D.; "Aptamers: An Emerging Class of Molecules That Rival Antibodies in Diagnostics"; Clinical Chemistry; 1999; pp. 1628-1650; vol. 45, No. 9; American Association for Clinical Chemistry.

Jin et al.; "Immobilization of plasmid DNA on an anti-DNA antibody modified coronary stent for intravascular site-specific gene therapy"; The Journal of Gene Medicine; 2008; pp. 421-429; vol. 10; John Wiley & Sons, Ltd.

Jori et al.; "Photodynamic Therapy in the Treatment of Microbial Infections: Basic Principles and Perspective Applications"; Lasers in Surgery and Medicine; 2006; pp. 468-481; vol. 38; Wiley-Liss, Inc.

Karrer et al.; "Photodynamic Inactivation of Staphylococci with 5-Aminolaevulinic Acid or Photofrin"; Lasers Med Sci; 1999; pp. 54-61; vol. 14; Springer-Verlag London Limited.

Kennedy et al.; "High intensity focused ultrasound: surgery of the future?"; The British Journal of Radiology; Sep. 2003; pp. 590-599; vol. 76; The British Institute of Radiology.

Kim et al.; "Real-Time Detection of Microbial Contamination"; IEEE Engineering in Medicine and Biology Magazine; Jan./Feb. 2004; pp. 122-129; IEEE.

Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.

Koenig et al.; "Laser-Induced Autofluorescence for Medical Diagnosis"; Journal of Fluorescence; 1994; pp. 17-40; vol. 4, No. 1; Plenum Publishing Corporation.

Koo et al.; "Development of a Streptavidin-Conjugated Single-Chain Antibody That Binds *Bacillus cereus* Spores"; Applied and Environmental Microbiology; Jul. 1998; pp. 2497-2502; vol. 64, No. 7; American Society for Microbiology.

Kupper et al.; "Generation of human antibody fragments against *Streptococcus mutans* using a phage display chain shuffling approach"; BMC Biotechnology; 2005; pp. 1-12; vol. 5, No. 4; BioMed Central Ltd.

Lee et al.; "Laser-Generated Stress Waves and Their Effects on the Cell Membrane"; IEEE Journal of Selected Topics in Quantum Electronics; Jul./Aug. 1999; pp. 997-1003; vol. 5, No. 4; IEEE.

Lee et al.; "Performance of an Immobilized Trypsin System for Improving Oxidative Stability of Milk"; Journal of Dairy Science; 1974; pp. 473-476; vol. 58, No. 4.

Lee et al.; "A strategy for predicting the chemosensitivity of human cancers and its application to drug discovery"; PNAS; Aug. 7, 2007; pp. 13086-13091; vol. 104, No. 32; The National Academy of Sciences of the USA.

Li et al.; "A Patient-Specific *in silico* Model of Inflammation and Healing Tested in Acute Vocal Fold Injury"; PLoS One; Jul. 2008; pp. 1-11; vol. 3, No. 7.

Ma et al.; "Potent Antitumor Activitiy of an Auristation-Conjugated, Fully Human Monoclonal Antibody to Prostate-Specific Membrane Antigen"; Clin Cancer Res; Apr. 15, 2006; pp. 2591-2596; vol. 12, No. 8; American Association for Cancer Research.

Maisch, Tim; "Anti-microbial photodynamic therapy: useful in the future?"; Lasers Med Sci; 2007; pp. 83-91; vol. 22; Springer-Verlag London Limited.

Maloney et al.; "Implantable Microchips for Controlled Drug Delivery"; Proceedings of the 26th Annual International Conference of the IEEE EMBS; San Francisco, CA USA; Sep. 1-5, 2004; pp. 2668-2669; IEEE.

Martin et al.; "Learning to Detect Natural Image Boundaries Using Local Brightness, Color, and Texture Cues"; IEEE Transactions on Pattern Analysis and Machine Intelligence; May 2004; pp. 530-549; vol. 26, No. 5; IEEE Computer Society.

Mateus et al.; "Adherence of *Candida albicans* to Silicone Induces Immediate Enhanced Tolerance to Fluconazole"; Antimicrobial Agents and Chemotherapy; Sep. 2004; pp. 3358-3366; vol. 48, No. 9; American Society for Microbiology.

Mendelow et al.; "Automated malaria detection by depolarization of laser light"; British Journal of Haematology; 1999; pp. 499-503; vol. 104; Blackwell Science Ltd.

Miller et al.; "Cancer Cells Ablation with Irreversible Electroporation"; Technology in Cancer Research & Treatment; Dec. 2005; pp. 1-7; vol. 4, No. 6; Adenine Press.

Miyata et al.; Tumor marker-responsive behavior of gels prepared by biomolecular imprinting; PNAS; Jan. 31, 2006; pp. 1190-1193; vol. 103, No. 5; The National Academy of Sciences of the USA.

Mohamed et al.; "Development of a Rare Cell Fractionation Device: Application for Cancer Detection"; IEEE Transactions on Nanobioscience; Dec. 2004; pp. 251-256; vol. 3, No. 4; IEEE.

Moore et al.; "The Comparative Size and Structure of Tumor Cells and Clumps in the Blood, Bone Marrow, and Tumor Imprints"; Cancer; Jan.-Feb. 1960; pp. 111-117; vol. 13, No. 1.

National Cancer Institute FactSheet; Lasers in Cancer Treatment: Questions and Answers; Aug. 10, 2004, pp. 1-4.

Nitin et al.; "Peptide-linked molecular beacons for efficient delivery and rapid mRNA detection in living cells"; Nucleic Acids Research; 2004; pp. 1-8; vol. 32, No. 6; Oxford University Press.

Nitzan et al.; "Endogenous Porphyrin Production in Bacteria by δ-Aminolaevulinic Acid and Subsequent Bacterial Photoeradication"; Lasers Med Sci; 1999; pp. 269-277; vol. 14; Springer-Verlag London Limited.

Norberto et al.; "Laser photoablation of colorectal adenomas"; Surg Endosc; 2005; pp. 1045-1048; vol. 19; Springer Science+Business Media, Inc.

Noronha et al.; "Hyperactivated B cells in human inflammatory bowel disease"; Journal of Leukocyte Biology; Oct. 2009; pp. 1-10; vol. 86; Society for Leukocyte Biology.

Nussbaum et al.; "Effects of 810 nm Laser Irradiation on In Vitro Growth of Bacteria: Comparison of Continuous Wave and Frequency Modulated Light"; Lasers in Surgery and Medicine; 2002; pp. 343-351; vol. 31; Wiley-Liss, Inc.

Nyitrai et al.; "Preparing Stents with Masking & Etching Technology"; 26th International Spring Seminar on Electronics Technology; May 8-11, 2003; Stará Lesná, Slovak Republic; pp. 321-324; IEEE.

Oberreuter et al.; "Identification of coryneform bacteria and related taxa by Fourier-transform infrared (FT-IR) spectroscopy"; International Journal of Systematic and Evolutionary Microbiology; 2002; pp. 91-100; vol. 52; IUMS.

Olson et al.; "Classification of cultured mammalian cells by shape analysis and pattern recognition"; Proc. Natl. Acad. Sci. USA; Mar. 1980; pp. 1516-1520; vol. 77, No. 3.

Ozaki et al.; "Cytokine and Cytokine Receptor Pleiotropy and Redundancy"; The Journal of Biological Chemistry; Aug. 16, 2002; pp. 29355-29358; vol. 277, No. 33.

Peppas et al.; "Polymers and Gels as Molecular Recognition Agents"; Pharmaceutical Research; May 2002; pp. 578-587; vol. 19, No. 5; Plenum Publishing Corporation.

Proske et al.; "Aptamers-basic research, drug development, and clinical applications"; Appl Microbiol Biotechnol; 2005; pp. 367-374; vol. 69; Springer-Verlag 2005.

Raghavan et al.; "BIAcore: a microchip-based system for analyzing the formation of macromolecular complexes"; Structure; Apr. 15, 1995; pp. 331-333; vol. 3; Current Biology Ltd.

Ribaut et al.; "Concentration and purification by magnetic separation of the erythrocytic stages of all human *Plasmodium* species"; Malaria Journal; 2008; pp. 1-5; vol. 7, No. 45; BioMed Central Ltd.

Ross, Gillian; "Accelerated partial breast irradiation: technology feasible but who will benefit?"; Breast Cancer Research; May 2005; pp. 110-112; vol. 7, No. 3; BioMed Central Ltd.

Roufosse, Florence; "Hypereosinophilic syndrome variants: diagnostic and therapeutic considerations"; haematologica; 2009; pp. 1188-1193; vol. 94, No. 9.

Sage et al.; "A Rapid and Nondestructive Method for Microbiological Testing in Pharmaceutical Manufacturing"; American Biotechnology Laboratory; Nov./Dec. 2006; pp. 1-5.

Samia et al.; "Quantum Dot-based Energy Transfer: Perspectives and Potential for Applications in Photodynamic Therapy"; Photochemistry and Photobiology; 2006; pp. 617-625; vol. 82; American Society for Photobiology.

Schuster et al.; "Circulating Tumor Cells as Prognostic Factor for Distant Metastases and Survival in Patients with Primary Uveal Melanoma"; Clin Cancer Res; Feb. 15, 2007; pp. 1171-1178; vol. 13, No. 4; American Association for Cancer Research.

Serebrovskaya et al.; "Targeting cancer cells by using an antireceptor antibody-photosensitizer fusion protein"; PNAS; Jun. 9, 2009; pp. 9221-9225; vol. 106, No. 23.

Shangguan et al.; "Aptamers evolved from live cells as effective molecular probes for cancer study"; PNAS; Aug. 8, 2006; pp. 11838-11843; vol. 103, No. 32; The National Academy of Sciences of the USA.

Spear et al.; "Isolation, characterization, and recovery of small peptide phage display epitopes selected against viable malignant glioma cells"; Cancer Gene Therapy; 2001; pp. 506-511; vol. 8, No. 7; Nature Publishing Group.

Terstappen et al.; "Four-Parameter White Blood Cell Differential Counting Based on Light Scattering Measurements"; Cytometry; 1988; pp. 39-43; vol. 9, Alan R. Liss, Inc.

Tsen et al.; "Inactivation of viruses by coherent excitations with a low power visible femtosecond laser"; Virology Journal; 2007; pp. 1-6; vol. 4, No. 50; BioMed Central Ltd.

Tseng et al.; "Inactivation of Viruses on Surfaces by Ultraviolet Germicidal Irradiation"; Journal of Occupational and Environmental Hygiene; Jun. 2007; pp. 400-405; vol. 4; No. 6; Joeh, LLC.

Ulrich et al.; "In Vitro Selection of RNA Aptamers That Bind to Cell Adhesion Receptors of *Trypanosoma cruzi* and Inhibit Cell Invasion"; The Journal of Biological Chemistry; Jun. 7, 2002; pp. 20756-20762; vol. 277, No. 23; The American Society for Biochemistry and Molecular Biology, Inc.

Vashist, Sandeep Kumar; "A Review of Microcantilevers for Sensing Applications"; Journal of Nanotechnology Online; Jun. 2007; pp. 1-15; vol. 3.

Vodovotz et al.; "Mathematical models of the acute inflammatory response"; Current Opinion in Critical Care; 2004; pp. 383-390; vol. 10; Lippincott Williams & Wilkins.

Vodovotz et al.; "Translational Systems Biology of Inflammation"; PLoS Computational Biology; Apr. 2008; pp. 1-6; vol. 4, No. 4.

Weatherall et al.; "Malaria and the Red Cell"; Hematology; 2002; pp. 35-57; American Society of Hematology.

Wissing et al.; "Illumination of the Malaria Parasite *Plasmodium falciparum* Alters Intracellular pH"; The Journal of Biological Chemistry; Oct. 4, 2002; pp. 37747-37755; vol. 277, No. 40; The American Society for Biochemistry and Molecular Biology, Inc.

Yang et al.; "On-Chip Electrochemical Impedance Spectroscopy for Biosensor Arrays"; IEEE Sensors; 2006; EXCO, Daegu, Korea; Oct. 22-25, 2006; pp. 93-96; IEEE.

Yang et al.; "Engineering Target-Responsive Hydrogels Based on Aptamer—Target Interactions"; J. Am. Chem. Soc.; 2008; pp. 6320-6321; vol. 130; No. 20; American Chemical Society.

Ye et al.; "Molecularly imprinted polymers as antibody and receptor mimics for assays, sensors and drug discovery"; Anal. Bioanal Chem; 2004; pp. 1887-1897; vol. 378; Springer-Verlag.

Zenker et al.; "From Inverse Problems in Mathematical Physiology to Quantitative Differential Diagnoses"; PLoS Computational Biology; Nov. 2007; pp. 2072-2086; vol. 3, No. 11.

Zharov et al.; "In vivo high-speed imaging of individual cells in fast blood flow"; Journal of Biomedical Optics; Sep./Oct. 2006; pp. 054034-1-054034-4; vol. 11, No. 5; SPIE.

Zharov et al.; "In Vivo Photothermal Flow Cytometry: Imaging and Detection of Individual Cells in Blood and Lymph Flow"; Journal of Cellular Biochemistry; 2006; pp. 916-932; vol. 97; Wiley-Liss, Inc.

Zheng et al.; "Design and Fabrication of a Micro Coulter Counter With Thin Film Electrodes"; Proceedings of 2006 International Conference on Microtechnologies in Medicine and Biology; Oknawa, Japan; May 9-12, 2006; IEEE.

Zhou et al.; Predicting short-term disease progression among HIV-infected patients in Asia and the Pacific region: preliminary results from the TREAT Asia HIV Observational Database (TAHOD); HIV Medicine; 2005; pp. 216-223; vol. 6; British HIV Association.

Arndt et al.; "Microwave Radiation-Therapeutic Application for Cure of Subcutaneous Bacterial Infections"; Space Life Science; 2005; 2 pgs.; NASA Biennial Research and Technology Report. National Aeronautics and Space Administration, Houston, TX.

Bartels et al.; "Use of diode laser energy (808 nm) for selective photothermolysis of contaminated wounds"; Proc. SPIE; 1995; pp. 602-606; vol. 2395; located at http://dx.doi.org/10.1117/12.209149.

Renneisen et al ; "Inhibition of Expression of Human Immunodeficiency Virus-1 in Vitro by Antibody-targeted Liposomes Containing Antisense RNA to the env Region"; The Journal of Biological Biochemistry; Sep. 25, 1990; pp. 16337-16342; vol. 265, No. 27; The American Society for Biochemistry and Molecular Biology, Inc.

Schneider et al.; "Automated Image Processing System for Shape Recognition of Single Red Blood Cells Based on Out-of-Focus Images"; Biorheology, Mar. 1995; pp. 237-238; vol. 32, No. 2; Elsevier.

Yeo et al.; "Bactericidal effects of high-power Nd:YAG laser radiation on *Staphylococcus aureus*"; Pure Appl. Opt.; Received for publication Jan. 9, 1998; pp. 643-655; vol. 7; IOP Publishing Ltd.

Yokota et al.; "Micro-Machined Stent-Type Flow Sensor for Evaluation of Nasal Respiration"; Micro Electro Mechanical Systems; Jan. 25-29, 2009; MEMS 2009; IEEE 22$^{nd}$ International Conference; pp. 495-498; IEEE.

\* cited by examiner

FIGURE 1
FIGURE 1A
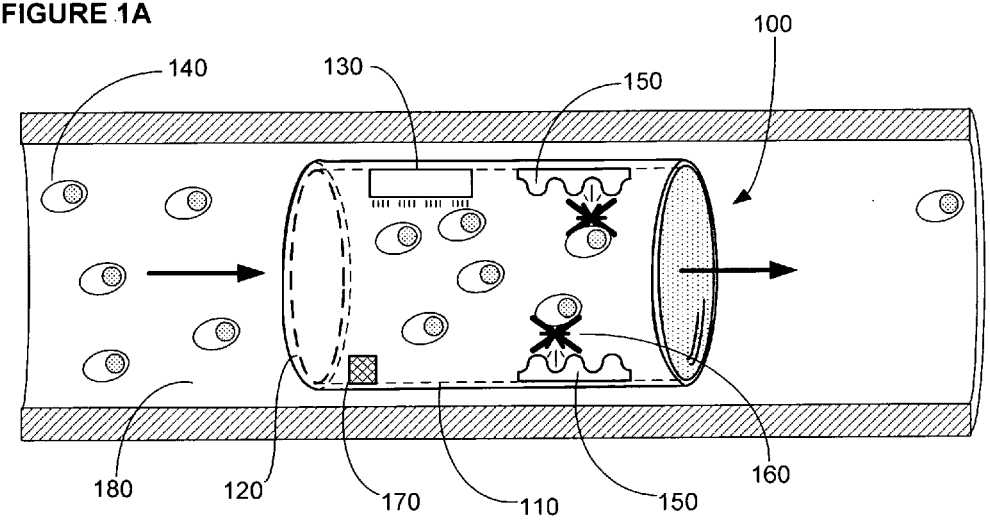
FIGURE 1B
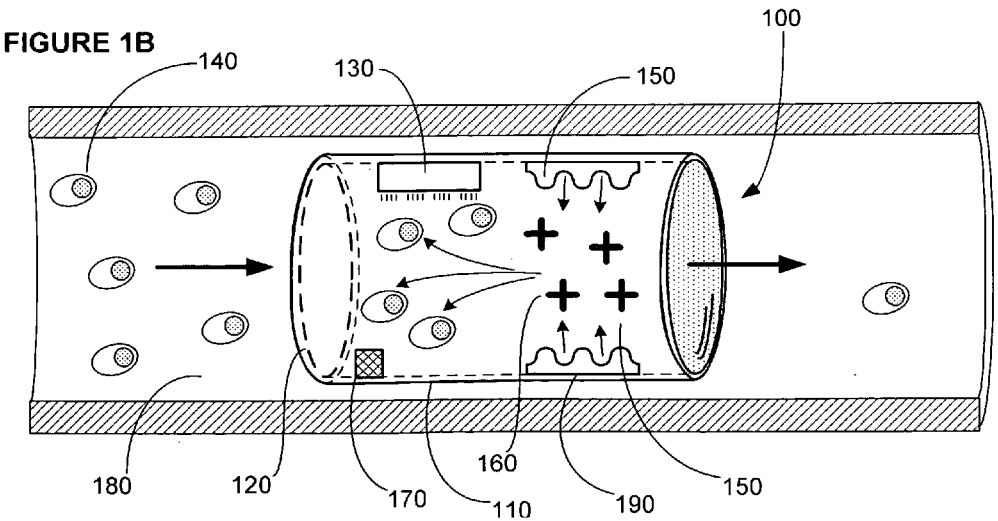

$x_1, x_2, x_3, x_4\ldots$ = concentrations of target cell $X$ $y_1, y_2, y_3, y_4\ldots$ = concentrations of target cell $Y$ $\sigma_1, \sigma_2, \sigma_3 \ldots$ = standard deviation $$f = \frac{(x_1-y_1)^2}{(\sigma_1)^2} + \frac{(x_2-y_2)^2}{(\sigma_2)^2} + \frac{(x_3-y_3)^2}{(\sigma_3)^2} + \cdots$$

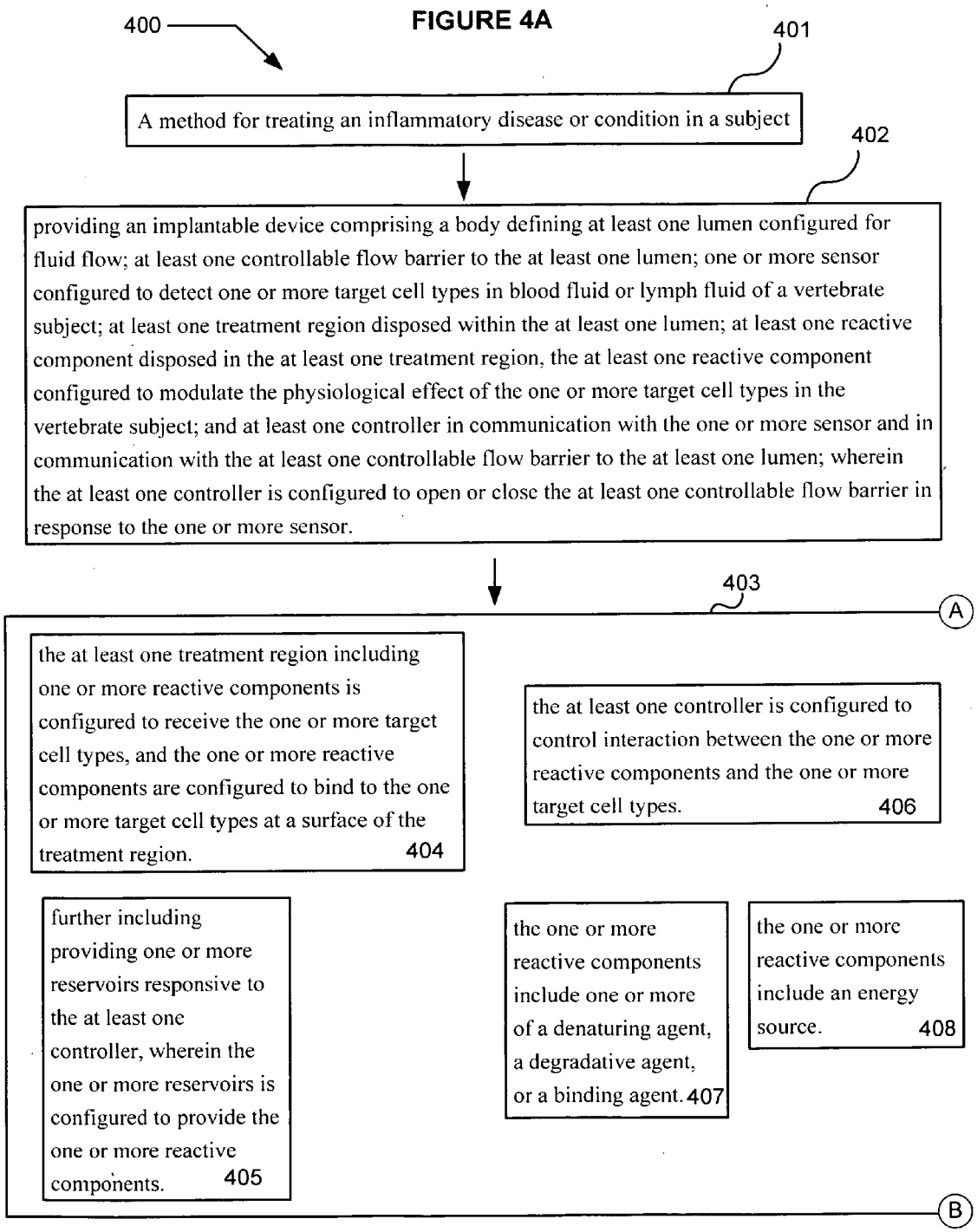

| | | |
|---|---|---|
| the one or more sensor is configured to detect the one or more target cell types within the at least one lumen. 409 | the one or more sensor and the at least one controller are configured to control levels of the detected one or more target cell types to limit a deviation from the target level. 412 | the one or more sensor is configured to target the device to a site having an elevated level of the target cell types. 413 |
| the one or more sensor is configured to detect the one or more target cell types in the at least one treatment region 410 | | the one or more sensor includes a biosensor, chemical sensor, physical sensor, or optical sensor. 414 |
| the one or more sensor is configured to detect the one or more target cell types after the one or more target cell types has passed through the at least one lumen or the at least one treatment region 411 | | |

Ⓑ

DEVICE FOR ACTIVELY REMOVING A TARGET CELL FROM BLOOD OR LYMPH OF A VERTEBRATE SUBJECT

RELATED APPLICATIONS

For purposes of the USPTO extra-statutory requirements, the present application constitutes a continuation of U.S. patent application Ser. No. 12/660,928, entitled DEVICE FOR ACTIVELY REMOVING A TARGET CELL FROM BLOOD OR LYMPH OF A VERTEBRATE SUBJECT, naming Roderick A. Hyde, Muriel Y. Ishikawa, Edward K. Y. Jung, Robert Langer, Eric C. Leuthardt, Nathan P. Myhrvold, Elizabeth A. Sweeney and Lowell L. Wood, Jr. as inventors, filed 5 Mar. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/660,926, entitled DEVICE FOR PASSIVELY REMOVING A TARGET COMPONENT FROM BLOOD OR LYMPH OF A VERTEBRATE SUBJECT, naming RODERICK A. HYDE, MURIEL Y. ISHIKAWA, EDWARD K. Y. JUNG, ROBERT LANGER, ERIC C. LEUTHARDT, NATHAN P. MYHRVOLD, ELIZABETH A. SWEENEY, AND LOWELL L. WOOD, JR. as inventors, filed 5 Mar. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,400, entitled DEVICE, SYSTEM, AND METHOD FOR CONTROLLABLY REDUCING INFLAMMATORY MEDIATORS IN A SUBJECT, naming RODERICK A. HYDE, MURIEL Y. ISHIKAWA, EDWARD K. Y. JUNG, ROBERT LANGER, ERIC C. LEUTHARDT, NATHAN P. MYHRVOLD, ELIZABETH A. SWEENEY, AND LOWELL L. WOOD, JR. as inventors, filed 25 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,399, entitled DEVICE, SYSTEM, AND METHOD FOR CONTROLLABLY REDUCING INFLAMMATORY MEDIATORS IN A SUBJECT, naming RODERICK A. HYDE, MURIEL Y. ISHIKAWA, EDWARD K. Y. JUNG, ROBERT LANGER, ERIC C. LEUTHARDT, NATHAN P. MYHRVOLD, ELIZABETH A. SWEENEY, AND LOWELL L. WOOD, JR. as inventors, filed 25 Feb. 2009, which is currently co-pending, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

Devices, systems, and methods are described herein for controlling the level of one or more target cell types in the blood fluid and/or lymph fluid of a vertebrate subject. The one or more target cell types include, but are not limited to, circulating cells, circulating emboli, blood cells, cancer cells, autoimmune-related cells, B cells, T cells, parasites, bacteria, fungi, infected cells, or virus-infected cells. The device or system described herein can be used in a method for treating a disease or condition in the subject. Examples of diseases, symptoms, conditions, or infections include, but are not limited to, acute and chronic inflammatory diseases, cardiovascular diseases, metabolic diseases, gastrointestinal diseases, neoplastic disease or condition, infectious disease or condition, bacterial infections, viral infections, parasitic infections, inflammation, and fungal infections.

An implantable device is described that includes a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate a physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The at least one treatment region including the one or more reactive components can be configured to receive the one or more target cell types, and the one or more reactive components are configured to bind to the one or more target cell types at a surface of the treatment region. The one or more reactive components can include one or more of a cell-disrupting agent, a binding agent, or an energy source. The cell-disrupting agent can include a denaturing agent or a degradative agent. The one or more binding agents can include, but is not limited to, one or more of an adhesion molecule, antibody, binding mimetic, polymer, lectin, integrin, or selectin. The one or more binding agents can include, but is not limited to, one or more of antibodies, receptors, or cognates configured to bind to at least one of the one or more target cell types. The one or more binding agents can include, but is not limited to, one or more of lectin, binding protein, catalytic antibody, catalytic aptamer, protease conjugate, or photoactivatable conjugate. The one or more binding agents can include one or more energy absorbers designed to absorb energy from the energy source. The one or more reactive components can include, but is not limited to, a cytotoxic agent, a cytostatic agent, a programmed cell death-inducing agent, a chemotherapeutic agent, or an antibody-toxin agent. The one or more reactive components can be configured to alter, arrest, or destroy the one or more target cell types. The one or more reactive components can be configured to produce necrosis or programmed cell death in the one or more target cell types. The at least one treatment region can be configured to be placed relative to a tumor or an organ in the vertebrate subject.

The one or more target cell types can include, but is not limited to, one or more of circulating cells or circulating emboli. The one or more target cell types can include, but is not limited to, cancer cells, autoimmune-related cells, B cells, T cells, parasites, bacteria, fungi, infected cells, or virus-infected cells. In an aspect, the one or more target cell types can refer to multiple target cell types or all cells of a single target cell type.

The at least one lumen can be configured for fluid flow including the one or more target cell types. The one or more sensor can be configured to detect the one or more target cell types within the at least one lumen. The one or more sensor can be configured to detect the one or more target cell types in the at least one treatment region. The one or more sensor can be configured to detect the one or more target cell types after the one or more target cell types has passed through the at least one lumen or the at least one treatment region. The at least one controller can be configured to return flow from the at least one lumen to a blood vessel or a lymph vessel. The at least one lumen can be configured for extended residence time of the blood fluid or the lymph fluid. In an aspect, the one or more sensor can be external to the at least one lumen. In an aspect, the one or more sensor is internal to the at least one lumen. The sensor can be configured to report to an outside source or to a computing device. In an aspect, the fluid can include, but is not limited to, blood or lymph. The at least one controller can include a processor. The one or more sensor can be configured to function in, or proximal to, one or more of a blood vessel or a lymph vessel of the vertebrate subject.

The device as described herein can further include providing a transmitter to report to the one or more sensor. The at least one controller can be further configured to control interaction between the one or more reactive components and the one or more target cell types. The device can further include providing one or more reservoirs responsive to the controller, wherein the one or more reservoirs is configured to provide the one or more reactive components, and the one or more reservoirs is configured to function in, or proximal to, one or more of a blood vessel or a lymph vessel of the vertebrate subject. The device can further include providing two or more parallel lumens configured to receive the one or more target cell types. In an aspect, a diameter of each of the two or more lumens can be approximately less than two cell diameters. In an aspect, a diameter of each of the two or more lumens can be approximately less than 10 μm. The at least one controllable flow barrier can be configured to be at least partially open.

The at least one controller can be configured to open or close the at least one controllable flow barrier in response to the one or more sensor to achieve a target level of the one or more target cell types in the vertebrate subject. The target level can include a desired concentration of the one or more target cell types in the one or more of the blood fluid or lymph fluid. The target level can include a desired range of concentrations of the one or more target cell types in the one or more of the blood fluid or lymph fluid. The target level can include a desired ratio of concentrations of two or more target cell types in the one or more of the blood fluid or lymph fluid. The target level can include a desired ratio of levels of two or more target cell types in the one or more of the blood fluid or lymph fluid. The one or more sensor and the at least one controller can be configured to control levels of the detected one or more target cell types to limit a deviation from the target level. The deviation can be determined by a weighted least squares fit. The at least one controller can be configured to control release of the one or more reactive components.

The one or more sensor can include, but is not limited to, a biosensor, chemical sensor, physical sensor, or optical sensor. The one or more sensor can include one or more of target recognition elements. The one or more target recognition elements can include, but is not limited to, one or more of an aptamer, antibody, receptor, affibody, mimic, nucleic acid, or synthetic compound. The sensor can include, but is not limited to, one or more of a recognition-based substrate, an aptamer-based substrate, an antibody-based substrate, surface plasmon resonance, genetically modified cells, or genetically modified cells with receptor-linked signaling. The genetically modified cells can include receptor-linked signaling by fluorogen-activating proteins. The sensor can be configured to target the device to a site having an elevated level of the target cell types. The sensor can be configured to report to an outside source or to a computing device, wherein in the sensor is configured to report a level of the one or more target cell types. The sensor can be configured to detect one or more of T-lymphocytes, B-lymphocytes, pre-cancer cells, cancer cells, inflammatory cells, infected cells, bacteria, parasites, fungi, virus-infected cells, platelets, or phagocytes. The sensor can be further configured to detect one or more of body temperature, vital signs, edema, oxygen level, hematocrit, pathogen or toxin level of the subject. The sensor can be further configured to detect one or more of antibodies, anaphylatoxins, cytokines, chemokines, leukotrienes, prostaglandins, complement factors, coagulation factors, or proinflammatory cytokines. The sensor can be further configured to detect one or more of TNF-α, IL-1, IL-1β, IL-6, IL-8, IL-10, IL-12, LPB, IFN-γ, LIF, MIF, MIP-1, MCP-1, C3-a, or C5-a. The sensor can be further configured to detect one or more of viruses, exotoxins, endotoxins, lipoproteins, or lipopolysaccharides. The at least one treatment region can include a matrix configured to present the one or more reactive components.

The one or more binding agents can include one or more target recognition elements. The one or more target recognition elements can include, but is not limited to, one or more of aptamer antibodies, receptors, affibody, mimic, nucleic acid, synthetic compound, or cognates configured to bind to at least one of the one or more target cell types. The one or more binding agent can include, but is not limited to, at least one of lectin, binding protein, catalytic antibody, catalytic aptamer, protease conjugate, or photoactivatable conjugate. The binding agent can include one or more of a specific binding ligand or a hydrophobic surface. The matrix can include, but is not limited to, one or more of beads, cells, vesicles, filters, hydrogel polymers, microparticles, nanoparticles, adsorbent, absorbent, or synthetic polymers. The specific binding ligand or the hydrophobic surface can include, but is not limited to, one or more of nucleic acid aptamers, peptide aptamers, molecular imprinting polymer, antibodies or fragments thereof, high affinity mimetics, synthetic binding molecules, or receptor binding molecules. The matrix can include, but is not limited to, one or more of a lectin, binding protein, receptor, antibody, catalytic antibody, catalytic aptamer, protease conjugate, or photoactivatable conjugate. The energy source can include acoustic energy or electronic energy. In an aspect, the energy source can include ultrasound. In an aspect, the energy source can include high-intensity focused ultrasound. The energy source can include, but is not limited to, at least one of microwave irradiation, gamma irradiation, electromagnetic irradiation, thermal energy, electron beam irradiation, vibrational/frequency irradiation, or atmospheric pressure glow discharge. The vibrational/frequency irradiation can include a set of differing energy inputs specifically directed to the one or more target cell types, wherein the set of differing energy inputs selectively resonates a plurality of resonant structures in the one or target cell types, and wherein the resonance controllably alters or reduces the activity of the one or more target cell types in the one or more of the blood fluid or lymph fluid of the vertebrate subject. In an aspect, the one or more target cell types can be modified with a functional group configured to be responsive to the set of differing energy inputs.

The one or more denaturing agents can include, but is not limited to, at least one of an acid, base, solvent, detergent, cross-linking agent, chaotropic agent, disulfide bond reducer, enzyme, drug, cell, or radical ion. The one or more degradative agents can include, but is not limited to, at least one of an enzyme, coenzyme, enzyme complex, catalytic antibody, proteasome, strong acid, strong base, radical, photoactivatable agent, drug, cell, or radical ion. In an aspect, the catalytic antibody can generate a radical ion.

The treatment region can include a source for producing the one or more reactive components. The treatment region can include one or more reservoirs including the one or more reactive components. The source can include at least one reservoir and at least one producer. The source can include at least one encapsulated cell. The at least one encapsulated cell can produce the one or more reactive components. The at least one encapsulated cell can include at least one genetically-engineered cell. The at least one encapsulated cell can include, but is not limited to, at least one of a mammalian cell, autologous cell, bacterial cell, yeast cell, plant cell, insect cell, artificial cell, or enucleated cell. The at least one encapsulated cell can include, but is not limited to, one or more of a myeloid cell, lymphocyte, or precursor thereof. The at least one encapsulated cell can include, but is not limited to, one or more of a T-lymphocyte, B-lymphocyte, macrophage, dendritic cell, monocyte, neutrophil, or NK cell. The source can include, but is not limited to, a protein, lipid micelle, liposome, synthetic polymer, or a combination thereof. The source can include a catalytic antibody. The catalytic antibody can include a radical ion generator.

The device can be intracorporeal. The device can be configured to be implanted. The device can include, but is not limited to, a stent, bypass implant, nanostructure or microstructure. The device can be configured to be implanted relative to an organ or tissue in the vertebrate subject. The device can be configured to be mobile relative to an organ or tissue in the vertebrate subject.

A method for treating an inflammatory condition or an inflammatory disease in a vertebrate subject is described that includes providing an implantable device comprising a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The at least one treatment region including the one or more reactive components can be configured to receive the one or more target cell types, and the one or more reactive components are configured to bind to the one or more target cell types at a surface of the treatment region. The one or more reactive components can include one or more of a cell-disrupting agent, a binding agent, or an energy source. The cell-disrupting agent can include a denaturing agent or a degradative agent. The one or more binding agents can include, but is not limited to, one or more of an adhesion molecule, antibody, binding mimetic, polymer, lectin, integrin, or selectin. The one or more binding agents can include, but is not limited to, one or more of antibodies, receptors, or cognates configured to bind to at least one of the one or more target cell types. The one or more binding agents can include, but is not limited to, one or more of lectin, binding protein, catalytic antibody, catalytic aptamer, protease conjugate, or photoactivatable conjugate. The one or more binding agents can include one or more energy absorbers designed to absorb energy from the energy source. The one or more reactive components can include, but is not limited to, a cytotoxic agent, a cytostatic agent, a programmed cell death-inducing agent, a chemotherapeutic agent, or an antibody-toxin agent. The one or more reactive components can be configured to alter, arrest, or destroy the one or more target cell types. The one or more reactive components can be configured to produce necrosis or programmed cell death in the one or more target cell types. The at least one treatment region can be configured to be placed relative to a tumor or an organ in the vertebrate subject.

The at least one lumen can be configured for fluid flow including the one or more target cell types. The one or more sensor can be configured to detect the one or more target cell types within the at least one lumen. The one or more sensor can be configured to detect the one or more target cell types in the at least one treatment region. The one or more sensor can be configured to detect the one or more target cell types after the one or more target cell types has passed through the at least one lumen or the at least one treatment region. The at least one controller can be configured to return flow from the at least one lumen to a blood vessel or a lymph vessel. The at least one lumen can be configured for extended residence time of the blood fluid or the lymph fluid. In an aspect, the one or more sensor can be external to the at least one lumen. In an aspect, the one or more sensor is internal to the at least one lumen. The sensor can be configured to report to an outside source or to a computing device. In an aspect, the fluid can include, but is not limited to, blood or lymph. The at least one controller can include a processor. The one or more sensor can be configured to function in, or proximal to, one or more of a blood vessel or a lymph vessel of the vertebrate subject.

The method as described herein can further include providing a transmitter to report to the one or more sensor. The at least one controller can be further configured to control interaction between the one or more reactive components and the one or more target cell types. The method can further include providing one or more reservoirs responsive to the controller, wherein the one or more reservoirs is configured to provide the one or more reactive components, and the one or more reservoirs is configured to function in, or proximal to, one or more of a blood vessel or a lymph vessel of the vertebrate subject. The method can further include providing two or more parallel lumens configured to receive the one or more target cell types. In an aspect, a diameter of each of the two or more lumens can be approximately less than two cell diameters. In an aspect, a diameter of each of the two or more lumens can be approximately less than 10 μm. The at least one controllable flow barrier can be configured to be at least partially open.

The at least one controller can be configured to open or close the at least one controllable flow barrier in response to the one or more sensor to achieve a target level of the one or more target cell types in the vertebrate subject. The target level can include a desired concentration of the one or more target cell types in the one or more of the blood fluid or lymph fluid. The target level can include a desired range of concentrations of the one or more target cell types in the one or more of the blood fluid or lymph fluid. The target level can include a desired ratio of concentrations of two or more target cell types in the one or more of the blood fluid or lymph fluid. The target level can include a desired ratio of levels of two or more target cell types in the one or more of the blood fluid or lymph fluid. The one or more sensor and the at least one controller can be configured to control levels of the detected one or more target cell types to limit a deviation from the target level. The deviation can be determined by a weighted least squares fit. The at least one controller can be configured to control release of the one or more reactive components.

The one or more sensor can include, but is not limited to, a biosensor, chemical sensor, physical sensor, or optical sensor. The one or more sensor can include one or more of target recognition elements. The one or more target recognition elements can include, but is not limited to, one or more of an aptamer, antibody, receptor, affibody, mimic, nucleic acid, or synthetic compound. The sensor can include, but is not limited to, one or more of a recognition-based substrate, an aptamer-based substrate, an antibody-based substrate, surface plasmon resonance, genetically modified cells, or genetically modified cells with receptor-linked signaling. The genetically modified cells can include receptor-linked signaling by fluorogen-activating proteins. The sensor can be configured to target the device to a site having an elevated level of the target cell types. The sensor can be configured to report to an outside source or to a computing device, wherein the sensor is configured to report a level of the one or more target cell types. The sensor can be configured to detect one or more of T-lymphocytes, B-lymphocytes, pre-cancer cells, cancer cells, inflammatory cells, infected cells, bacteria, parasites, fungi, virus-infected cells, platelets, or phagocytes. The sensor can be further configured to detect one or more of body temperature, vital signs, edema, oxygen level, hematocrit, pathogen or toxin level of the subject. The sensor can be further configured to detect one or more of antibodies, anaphylatoxins, cytokines, chemokines, leukotrienes, prostaglandins, complement factors, coagulation factors, or proinflammatory cytokines. The sensor can be further configured to detect one or more of TNF-α, IL-1, IL-1β, IL-6, IL-8, IL-10, IL-12, LPB, IFN-γ, LIF, MIF, MIP-1, MCP-1, C3-a, or C5-a. The sensor can be further configured to detect one or more of viruses, exotoxins, endotoxins, lipoproteins, or lipopolysaccharides. The at least one treatment region can include a matrix configured to present the one or more reactive components.

The one or more binding agents can include one or more target recognition elements. The one or more target recognition elements can include, but is not limited to, one or more of aptamer antibodies, receptors, affibody, mimic, nucleic acid, synthetic compound, or cognates configured to bind to at least one of the one or more target cell types. The one or more binding agent can include, but is not limited to, at least one of lectin, binding protein, catalytic antibody, catalytic aptamer, protease conjugate, or photoactivatable conjugate. The binding agent can include one or more of a specific binding ligand or a hydrophobic surface. The matrix can include, but is not limited to, one or more of beads, cells, vesicles, filters, hydrogel polymers, microparticles, nanoparticles, adsorbent, absorbent, or synthetic polymers. The specific binding ligand or the hydrophobic surface can include, but is not limited to, one or more of nucleic acid aptamers, peptide aptamers, molecular imprinting polymer, antibodies or fragments thereof, high affinity mimetics, synthetic binding molecules, or receptor binding molecules. The matrix can include, but is not limited to, one or more of a lectin, binding protein, receptor, antibody, catalytic antibody, catalytic aptamer, protease conjugate, or photoactivatable conjugate. The energy source can include acoustic energy or electronic energy. In an aspect, the energy source can include ultrasound. In an aspect, the energy source can include high-intensity focused ultrasound. The energy source can include, but is not limited to, at least one of microwave irradiation, gamma irradiation, electromagnetic irradiation, thermal energy, electron beam irradiation, vibrational/frequency irradiation, or atmospheric pressure glow discharge. The vibrational/frequency irradiation can include a set of differing energy inputs specifically directed to the one or more target cell types, wherein the set of differing energy inputs selectively resonates a plurality of resonant structures in the one or target cell types, and wherein the resonance controllably alters or reduces the activity of the one or more target cell types in the one or more of the blood fluid or lymph fluid of the vertebrate subject. In an aspect, the one or more target cell types can be modified with a functional group configured to be responsive to the set of differing energy inputs.

The one or more denaturing agents can include, but is not limited to, at least one of an acid, base, solvent, detergent, cross-linking agent, chaotropic agent, disulfide bond reducer, enzyme, drug, cell, or radical ion. The one or more degradative agents can include, but is not limited to, at least one of an enzyme, coenzyme, enzyme complex, catalytic antibody, proteasome, strong acid, strong base, radical, photoactivatable agent, drug, cell, or radical ion. In an aspect, the catalytic antibody can generate a radical ion.

The treatment region can include a source for producing the one or more reactive components. The treatment region can include one or more reservoirs including the one or more reactive components. The source can include at least one reservoir and at least one producer. The source can include at least one encapsulated cell. The at least one encapsulated cell can produce the one or more reactive components. The at least one encapsulated cell can include at least one genetically-engineered cell. The at least one encapsulated cell can include, but is not limited to, at least one of a mammalian cell, autologous cell, bacterial cell, yeast cell, plant cell, insect cell, artificial cell, or enucleated cell. The at least one encapsulated cell can include, but is not limited to, one or more of a myeloid cell, lymphocyte, or precursor thereof. The at least one encapsulated cell can include, but is not limited to, one or more of a T-lymphocyte, B-lymphocyte, macrophage, dendritic cell, monocyte, neutrophil, or NK cell. The source can include, but is not limited to, a protein, lipid micelle, liposome, synthetic polymer, or a combination thereof. The source can include a catalytic antibody. The catalytic antibody can include a radical ion generator. The one or more target cell types can include, but is not limited to, one or more of circulating cells or circulating emboli. The one or more target cell types can include, but is not limited to, cancer cells, autoimmune-related cells, B cells, T cells, parasites, bacteria, fungi, or infected cells.

A method for modulating an inflammatory condition or an inflammatory disease in a vertebrate subject is described that includes providing an implantable device comprising a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The at least one treatment region including one or more reactive components can be configured to receive the one or more target cell types, and the one or more reactive components can be configured to bind to the one or more target cell types at a surface of the at least one treatment region. The one or more reactive components can include, but is not limited to, one or more of a cell-disrupting agent, a binding agent, or an energy source.

A method for treating an infectious disease or an infectious condition in a vertebrate subject is described that includes providing an implantable device comprising: a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The at least one treatment region including one or more reactive components can be configured to receive the one or more target cell types, and the one or more reactive components can be configured to bind to the one or more target cell types at a surface of the at least one treatment region. The one or more reactive components can include, but is not limited to, one or more of a cell-disrupting agent, a binding agent, or an energy source.

A method for modulating an infectious disease or an infectious condition in a vertebrate subject is described that includes providing an implantable device comprising: a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The at least one treatment region including one or more reactive components can be configured to receive the one or more target cell types, and the one or more reactive components can be configured to bind to the one or more target cell types at a surface of the at least one treatment region. The one or more reactive components can include, but is not limited to, one or more of a cell-disrupting agent, a binding agent, or an energy source.

A method for treating a neoplastic disease or a neoplastic condition in a vertebrate subject is described that includes providing an implantable device comprising: a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The at least one treatment region including one or more reactive components can be configured to receive the one or more target cell types, and the one or more reactive components can be configured to bind to the one or more target cell types at a surface of the at least one treatment region. The one or more reactive components can include, but is not limited to, one or more of a cell-disrupting agent, a binding agent, or an energy source.

A method for modulating a neoplastic disease or a neoplastic condition in a vertebrate subject is described that includes providing an implantable device comprising: a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The at least one treatment region including one or more reactive components can be configured to receive the one or more target cell types, and the one or more reactive components can be configured to bind to the one or more target cell types at a surface of the at least one treatment region. The one or more reactive components can include, but is not limited to, one or more of a cell-disrupting agent, a binding agent, or an energy source.

A system is described that includes an implantable device comprising a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The at least one treatment region including one or more reactive components can be configured to receive the one or more target cell types, and the one or more reactive components can be configured to bind to the one or more target cell types at a surface of the at least one treatment region. The one or more reactive components can include, but is not limited to, one or more of a cell-disrupting agent, a binding agent, or an energy source.

An implantable device is described that includes a system including a signal-bearing medium including one or more instructions for treatment of a vertebrate subject through a device including one or more instructions for receiving data including data from at least one controllable flow barrier to the at least one lumen; one or more instructions for receiving data including data from one or more sensor configured to detect one or more target cell types in blood fluid or lymph fluid of a vertebrate subject; one or more instructions for receiving data including data from at least one treatment region disposed within the at least one lumen; one or more instructions for receiving data including data from at least one reactive component disposed in the at least one treatment region, the at least one reactive component configured to modulate the physiological effect of the one or more target cell types in the vertebrate subject; and one or more instructions for receiving data including data from at least one controller in communication with the one or more sensor and in communication with the at least one controllable flow barrier to the at least one lumen; wherein the at least one controller is configured to open or close the at least one controllable flow barrier in response to the one or more sensor.

A system is described that includes at least one computer program included on a computer-readable recordable-type medium for use with at least one computer system wherein the computer program includes, one or more instructions for treatment of a vertebrate subject through a device including one or more instructions for receiving data including data from at least one controllable flow barrier to the at least one lumen; one or more instructions for receiving data including data from one or more sensor configured to detect one or more target cell types in blood fluid or lymph fluid of a vertebrate subject; one or more instructions for receiving data including data from at least one treatment region disposed within the at least one lumen; one or more instructions for receiving data including data from at least one reactive component disposed in the at least one treatment region, the at least one reactive component configured to modulate the physiological effect of the one or more target cell types in the vertebrate subject; and one or more instructions for receiving data including data from at least one controller in communication with the one or more sensor and in communication with the at least one controllable flow barrier to the at least one lumen; wherein the at least one controller is configured to open or close the at least one controllable flow barrier in response to the one or more sensor.

The foregoing summary is illustrative only and is not intended to be in any way limiting. In addition to the illustrative aspects, embodiments, and features described in the summary, further aspects, embodiments, and features will become apparent by reference to the drawings and the following detailed description.

BRIEF DESCRIPTION OF THE FIGURES

FIGS. 1A and 1B depict a diagrammatic view of an aspect of an embodiment of a device.

FIGS. 4A and 4B depict a logic flowchart of a method for treating a disease or condition in a vertebrate subject.

DETAILED DESCRIPTION

Figure 2:
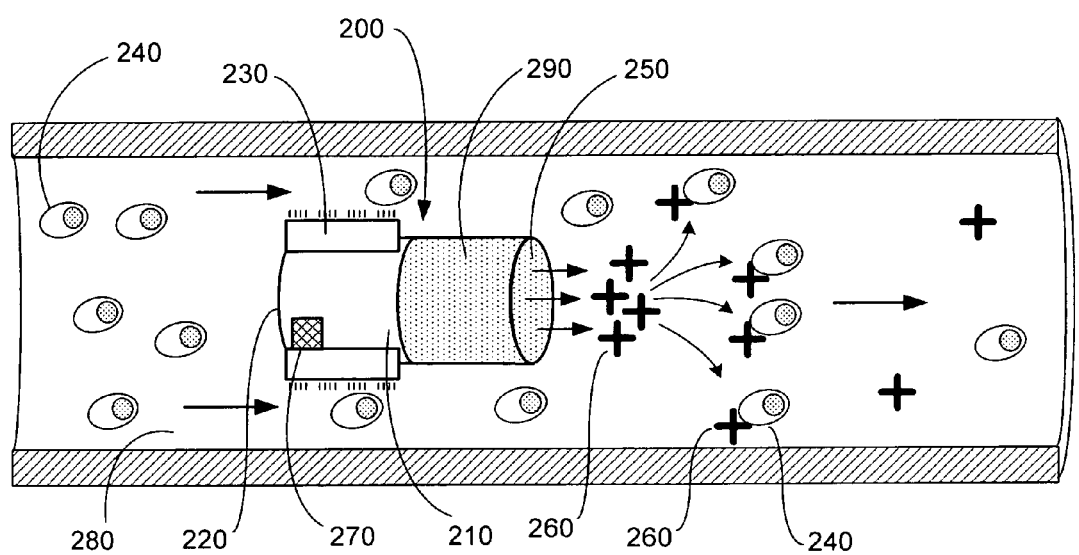
FIG. 2 depicts a diagrammatic view of an aspect of an embodiment of a device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

This document uses formal outline headings for clarity of presentation. However, it is to be understood that the outline headings are for presentation purposes, and that different types of subject matter may be discussed throughout the application (e.g., method(s) may be described under composition heading(s) and/or kit headings, and/or descriptions of single topics may span two or more topic headings). Hence, the use of the formal outline headings is not intended to be in any way limiting.

Devices, systems, and methods are described herein for controlling the level of one or more target cell types in the blood fluid and/or lymph fluid of a vertebrate subject. The device or system described herein can be used in a method for treating a disease or condition in the subject. Examples of diseases, symptoms, conditions, or infections include, but are not limited to, acute and chronic inflammatory diseases, cardiovascular diseases, metabolic diseases, gastrointestinal diseases, neoplastic disease or condition, infectious disease or condition, bacterial infections, viral infections, parasitic infections, inflammation, and fungal infections.

An implantable device is described herein for controlling the level of one or more target cell types in the blood and/or lymph of vertebrate a subject that includes a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The treatment region can include one or more reactive components is configured to receive the one or more target cell types, and the one or more reactive components are configured to bind to the one or more target cell types at a surface of the treatment region.

The one or more target cell types can include, but is not limited to, one or more of circulating cells or circulating emboli. The one or more target cell types can include, but is not limited to, blood cells, cancer cells, autoimmune-related cells, B cells, T cells, parasites, bacteria, fungi, infected cells, or virus-infected cells. In an aspect, the one or more target cell types can refer to multiple target cell types or all cells of a single target cell type.

To modulate a physiological effect of the one or more target cell types, the at least one reactive component can interact directly with the one or more target cell types or indirectly through an intermediate cell type or intermediate cellular component, e.g., hormones, signaling components, soluble cell receptor, membrane-bound cell receptor, soluble ligand, or bound ligand. The at least one reactive component can include an activity in the presence or absence the one or more target cell types that is configured to modulate the physiological effect of the one or more target cell types.

In some aspects, the controller can be configured to control interaction between the one or more reactive components and the one or more target cell types. The device can further include one or more reservoirs responsive to the controller, wherein the one or more reservoirs is configured to provide the one or more reactive components, and the one or more reservoirs is configured to function in, or proximal to, one or more of a blood vessel or a lymph vessel of the vertebrate subject.

The one or more reactive components can include, but are not limited to, one or more of a cell-disrupting agent, a binding agent, or an energy source. The one or more reactive components can further include, but are not limited to, a cytotoxic agent, a cytostatic agent, a programmed cell death-inducing agent, a chemotherapeutic agent, an antibody-toxin agent, or a combination thereof. The one or more binding agents on a matrix adapted to the treatment region can be configured to sequester at least one of the one or more target cell types from the one or more of blood fluid or lymph fluid. One or more target cell types can be sequestered by the binding agent prior to treatment with one or more reactive components including, but not limited to, one or more of a cell-disrupting agent, a binding agent, an energy source, a cytotoxic agent, a cytostatic agent, a programmed cell death-inducing agent, a chemotherapeutic agent, an antibody-toxin agent, or a combination thereof. In an aspect, the one or more sensor can be configured to function in, or proximal to, one or more of a blood vessel or a lymph vessel of the vertebrate subject.

In an aspect, the target level can include a desired concentration of the one or more target cell types in the blood fluid or lymph fluid of the vertebrate subject. The target level can include a desired range of concentrations of the one or more target cell types in the blood fluid or lymph fluid. The target level can include a desired ratio of concentrations of two or more target cell types in the blood fluid or lymph fluid. The sensor and the controller can be configured to control levels of the one or more target cell types to substantially attain the target level. The sensor and the controller can be configured to control levels of the target cell types to limit a deviation from the target level. The deviation can be determined by a weighted least squares fit calculation run by an onboard or an off-board processor.

A method for preventing or modulating a disease or condition in a vertebrate subject includes providing an implantable device comprising a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The disease or condition can include, but is not limited to, an inflammatory disease or inflammatory condition, an infectious disease or infectious condition, or a neoplastic disease or neoplastic condition.

A system is described herein that includes an implantable device comprising a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor.

The device as described herein can include at least one reactive component disposed in the at least one treatment region, wherein the at least one reactive component is configured to modulate the physiological effect of the one or more target cell types in the vertebrate subject which refers to decreasing an activity of the one or more of target cell types by cell disruption or inactivation utilizing one or more of a cell-disrupting agent, a binding agent, or an energy source. The one or more reactive components can further include for example, but is not limited to, a cytotoxic agent, a cytostatic agent, a programmed cell death-inducing agent, a chemotherapeutic agent, or an antibody-toxin agent. The device can be used in a method for treating or modulating a disease or condition in the vertebrate subject. The device can include one or more sensors configured to function in or proximal to one or more blood vessel or lymph vessel of the vertebrate subject. The device including the one or more sensors can be configured to detect one or more target cell types in the blood fluid or lymph fluid of the vertebrate subject and configured to control levels of the one or more target cell types to a target level. The one or more sensors can include, for example, a biosensor, a chemical sensor, a physical sensor, an optical sensor, or a combination thereof. The one or more sensors can further include one or more of an aptamer, an antibody, a receptor, a recognition-based substrate, an aptamer-based substrate, an antibody-based substrate, surface plasmon resonance, genetically modified cells, or genetically modified cells with receptor-linked signaling. The device can further include one or more treatment regions configured to receive the blood fluid or lymph fluid of the vertebrate subject through a flow route. The treatment region can include one or more reactive components configured to receive the one or more target cell types, and the one or more reactive components are configured to bind to the one or more target cell types at a surface of the treatment region. The one or more treatment regions can include one or more specific binding agents for binding one or more specific target cell types. The one or more specific binding agents can be attached to one or more substrates in the one or more treatment regions. The one or more substrates can be one or more surfaces of the one or more treatment regions. The one or more substrates can include one or more matrix components retained in the one or more treatment regions. The one or more treatment regions can include one or more reactive components configured to modulate a physiological effect of one or more target cell types found in the blood fluid or lymph fluid of the vertebrate subject that flow through the flow route. The device can further include at least one controller in communication with the one or more sensor and in communication with the at least one controllable flow barrier to the at least one lumen; wherein the at least one controller is configured to open or close the at least one controllable flow barrier in response to the one or more sensor. The controller can be configured to control interaction between the one or more reactive components and the one or more target cell types. The controller can further control release and/or activation of one or more reactive components. The device can further include one or more reservoirs responsive to the controller, wherein the one or more reservoirs can be configured to provide the one or more reactive components. The one or more reservoirs can be configured to function in, or proximal to, one or more of a blood vessel or a lymph vessel of the vertebrate subject.

In an aspect, a method is provided for treating or modulating a disease or condition, including, but not limited to, an inflammatory disease or condition, an infectious disease or condition, or a neoplastic disease or condition in a vertebrate subject. In an aspect, the disease or condition, can be modulated, alleviated, treated, prevented, reduced or eliminated by the device configured to modulate a physiological effect of one or more target cell types in the blood fluid or lymph fluid. The disease or condition can include, but is not limited to, cardiovascular diseases (e.g., ischemic heart disease, inflammatory heart disease), metabolic diseases (e.g., diabetes), gastrointestinal diseases (e.g., colitis, Crohn's disease), bacterial infections (e.g., *Staphylococcus* bacteremia, anthrax), viral infections (e.g., AIDS, hepatitis, hemorrhagic fever), parasitic infections (e.g., malaria, sleeping sickness, Chagas disease), metastatic cancer (e.g., lung, breast, skin, colon, kidney, prostate, pancreas, and cervix); blood cancers (e.g., leukemia, lymphoma, Hodgkin's disease, myeloma). Additional examples include a number of inflammatory diseases including but not limited to systemic inflammatory response syndrome, sepsis, septic shock, multiple organ dysfunction syndrome, ischemia reperfusion, hyperreactive airway disease, (e.g., asthma, chronic obstructive pulmonary disease, rhinitis, sinusitis), allergic reaction, anaphylaxis, autoimmune disease, infectious disease, pulmonary failure, allograft rejection, graft versus host disease (GVHD), chronic inflammatory disease, psoriatic arthritis, rheumatoid arthritis.

With reference to the figures, and with reference now to FIGS. 1, 2, 3 and 4, depicted is an aspect of a device, system, or method that can serve as an illustrative environment of and/or for subject matter technologies, for example, an implantable device is described that includes a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. The specific devices and methods described herein are intended as merely illustrative of their more general counterparts.

Referring to FIGS. 1A and 1B, depicted is a partial diagrammatic view of an illustrative embodiment. In FIG. 1A, an implantable device 100 includes a body defining at least one lumen 110 configured for fluid flow; at least one controllable flow barrier 120 to the at least one lumen; one or more sensor 130 configured to detect one or more target cell types 140 in blood fluid or lymph fluid 180 of a vertebrate subject; at least one treatment region 150 disposed within the at least one lumen 110; at least one reactive component 160 disposed in the at least one treatment region 150, the one or more reactive component 160 configured to modulate the physiological effect of the one or more target cell types 140 in the vertebrate subject; and at least one controller 170 in communication with the one or more sensor 130 and in communication with the at least one controllable flow barrier 120 to the at least one lumen 110; wherein the at least one controller 170 is configured to open or close the at least one controllable flow barrier 120 in response to the one or more sensor 130. The one or more reactive components 160 are configured to bind to the one or more target cell types 140 at a surface of the treatment region 150.

In FIG. 1B, an implantable device 100 includes a body defining at least one lumen 110 configured for fluid flow; at least one controllable flow barrier 120 to the at least one lumen; one or more sensor 130 configured to detect one or more target cell types 140 in blood fluid or lymph fluid 180 of a vertebrate subject; at least one treatment region 150 disposed within the at least one lumen 110; at least one reactive component 160 disposed in the at least one treatment region 150, the one or more reactive component 160 configured to modulate the physiological effect of the one or more target cell types 140 in the vertebrate subject; and at least one controller 170 in communication with the one or more sensor 130 and in communication with the at least one controllable flow barrier 120 to the at least one lumen 110; wherein the at least one controller 170 is configured to open or close the at least one controllable flow barrier 120 in response to the one or more sensor 130. The at least one controller 170 can be configured to control interaction between the one or more reactive components 160 and the one or more target cell types 140. The device 100 can further include one or more reservoirs 190 responsive to the at least one controller 170, wherein the one or more reservoirs 190 is configured to provide the one or more reactive components 160, which can diffuse to interact with the one or more target cell types 140 in the vertebrate subject. The one or more reservoirs 190 is configured to function in, or proximal to, one or more of a blood vessel or a lymph vessel of the vertebrate subject.

In FIG. 2, an implantable device 200 includes a body defining at least one lumen 210 configured for fluid flow; at least one controllable flow barrier 220 to the at least one lumen 210; one or more sensor 230 configured to detect one or more target cell types 240 in blood fluid or lymph fluid 280 of a vertebrate subject; at least one treatment region 250 disposed within the at least one lumen 210; at least one reactive component 260 disposed in the at least one treatment region 250, the one or more reactive component 260 configured to modulate the physiological effect of the one or more target cell types 240 in the vertebrate subject; and at least one controller 270 in communication with the one or more sensor 230 and in communication with the at least one controllable flow barrier 220 to the at least one lumen 210; wherein the at least one controller 270 is configured to open or close the at least one controllable flow barrier 220 in response to the one or more sensor 230. The at least one controller 270 can be configured to control interaction between the one or more reactive components 260 and the one or more target cell types 240. The device 200 can further include one or more reservoirs 290 responsive to the at least one controller 270, wherein the one or more reservoirs 290 is configured to provide the one or more reactive components 260, which can diffuse to interact with the one or more target cell types 240 in the vertebrate subject. The one or more reservoirs 290 is configured to function in, or proximal to, one or more of a blood vessel or a lymph vessel of the vertebrate subject.

Figure 3:
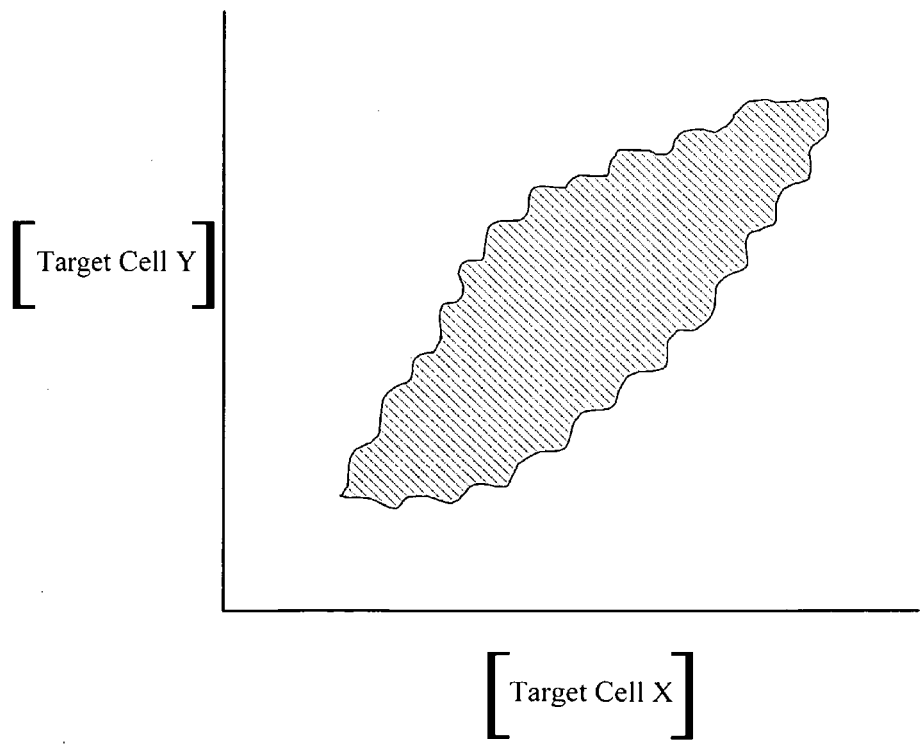
FIG. 3 depicts a diagrammatic view of an aspect of an embodiment of a device.

Referring to FIG. 3, depicted is a partial diagrammatic view of an illustrative embodiment of calculations of a target value in a device including a sensor configured to detect one or more target cell types in peripheral blood of a subject and configured to control levels of the one or more target cell types to a target value in blood fluid or lymph fluid of a vertebrate subject. In an aspect, the target value can include a desired concentration of the one or more target cell types in the peripheral blood, or the target value can include a desired range of concentrations of the one or more target cell types in the peripheral blood. In an aspect, the target value can include a desired ratio of concentrations of two or more target cell types in the peripheral blood. In an aspect, the target value can be used to determine relative levels of the target cell types. The desired ratio of concentrations can be determined by any method or means, including for example, by a least squares fit of the concentrations of the two or more target cell types. For example, the desired ratio of concentrations can be determined by a least squares fit of the concentrations of the two or more target cell types at concentrations $x_1$, $x_2$, $x_3$, and $x_4$ for a first inflammatory mediator, X, and at concentrations $y_1$, $y_2$, $y_3$, and $y_4$ for a second inflammatory mediator, Y. The least squares can fit to a line or to a two or three dimensional space indicating the preferred ratio of the two or more target cell types.

Referring to FIGS. 4A and 4B, depicted is a logic flowchart of a method for treating 401 an inflammatory disease or inflammatory condition in a subject. The method 400 includes providing an implantable device 402 comprising a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor. In an aspect, the treatment region 404 can include one or more reactive components configured to receive the one or more target cell types, and the one or more reactive components can be configured to bind to the one or more target cell types at a surface of the treatment region. The method can further include providing 405 one or more reservoirs responsive to the controller, wherein the one or more reservoirs is configured to provide the one or more reactive components. The controller 406 can be configured to control interaction between the one or more reactive components and the one or more target cell types. The one or more reactive components 407 can include one or more of a denaturing agent, a degradative agent, or a binding agent. The one or more reactive components 408 can include an energy source. The one or more sensor 409 can be configured to detect the one or more target cell types within the at least one lumen. The one or more sensor 410 can be configured to detect the one or more target cell types in the at least one treatment region. The one or more sensor 411 can be configured to detect the one or more target cell types after the one or more target cell types has passed through the at least one lumen or the at least one treatment region. The one or more sensor and the at least one controller 412 can be configured to control levels of the detected one or more target cell types to limit a deviation from the target level. The one or more sensor 413 can be configured to target the device to a site having an elevated level of the target cell types. The one or more sensor 414 can include a biosensor, chemical sensor, physical sensor, or optical sensor.

Target cell types. A device is described herein that can include one or more reactive components configured to modulate a physiological effect of one or more target cell types in the blood fluid or lymph fluid of the vertebrate subject. The one or more reactive components can be configured to alter, arrest, or destroy the one or more target cell types. The one or more reactive components can be configured to produce necrosis or programmed cell death in the one or more target cell types. The target cell types can be one or more blood cells (e.g., platelets, red blood cells, neutrophils, lymphocytes, monocytes, eosinophils, basophils), pathogens (e.g., virus, bacteria, fungus, parasite), or cancer cells (e.g., metastatic cancer cells, blood cancer cells).

The one or more target cell types can include one or more blood cells associated with a pathological state in which the normal circulating levels of one or more class of blood cells is elevated. For example, elevated levels of red blood cells are associated with exposure to carbon monoxide, long-term lung disease, kidney disease, some cancers, certain forms of heart disease, liver disease. Elevated levels of platelets are associated with bleeding, iron deficiency, cancer, or bone marrow pathologies. Elevated levels of neutrophils and eosinophils are associated with infection, malignancy and autoimmune diseases. In an aspect, the target cell types are blood cells that are modified or altered as a result of a disease or condition. For example, hyperactivated B-lymphocytes in patients with inflammatory bowel disease exhibit increased surface expression of toll-like receptor 2 (TLR2) relative to B-lymphocytes from normal individuals. See, e.g., Noronha, et al., *J. Leukoc. Biol.* 86: Epub ahead of print; Rea, WebMD, Complete Blood Count (CBC) at www.webmd.com/a-to-z-guides/complete-blood-count-cbc. Last updated Sep. 12, 2008; accessed Oct. 5, 2009; each of which is incorporated herein by reference.

The one or more target cell types can include one or more pathogen-infected cells circulating in the blood fluid or lymph fluid of the vertebrate subject. Examples of blood borne pathogens include, but are not limited to, viruses, e.g., human immunodeficiency virus (HIV), and the hepatitis B, hepatitis C, and hepatitis D viruses; bacteria, e.g., *Staphylococcus, Streptococcus, Pseudomonas, Haemophilus, Escherichia coli*; fungi, e.g., *Candida albicans, Candida glabrata, Aspergillus, T. glabrata, Candida tropicalis, C. krusei*, and *C. parapsilosis*; and parasites, e.g., *Trypanosoma cruzi, Trypanosoma brucei, Leishmania, Plasmodium, Babesia microti, Toxoplasma gondii*. Other bacterial pathogens that might be found in the blood fluid or lymph fluid at some point during a bacterial infection include, but are not limited to, *Bartonella, Coxiella burnetii, Chlamydia, Salmonella, Shigella, Yersinia, Legionella, Neisseria, Mycobacterium tuberculosis, Listeria, Corynebacterium diphtheria, Campylobacter, Enterobacter*. Other viral pathogens or pathogen-infected cells that might be found in the blood fluid or lymph fluid at some point during a viral infection include, but are not limited to, cells infected with cytomegalovirus, influenza, human T-lymphotrophic virus, Epstein-Barr virus, roseolovirus, herpes lymphotropic virus, Karposi's sarcoma-associated herpesvirus, herpes simplex virus, Ebola virus, Marburg virus.

In an aspect, the one or more target cell types can include one or more circulating blood cells infected with a pathogen including, but not limited, to bacteria, virus, or parasite. In an aspect, the one or more target cell types can be circulating blood cells infected with bacteria such as, for example, infection of red blood cells with *B. bacilliformis* or *Bartonella* spp. See, e.g., Dehio *Cell. Microbiol.* 10:1591-1598, 2008; Chomel et al., *Vet. Res.* 40: 29, 2009, each of which is incorporated herein by reference. In an aspect, the one or more target cell types are one or more cells infected with HIV, primarily $CD4^+$ T lymphocytes but also including macrophages and dendritic cells. In an aspect, the one or more target cell types are red blood cells infected with the malaria parasite *Plasmodium falciparum*. Red blood cells infected with *P. falciparum* can be distinguished from normal red blood cells by visual inspection, changes in granularities and changes in surface protein expression including expression on the red blood cell surface of the parasite derived protein *P. falciparum* erythrocyte membrane protein (PfEMP1). See, e.g., Dempster & Di Ruperto, *Circuits and Systems*, ISCAS 2001; The 2001 IEEE International Symposium 5: 291-294, 2001; Weatherall, et al., *Hematology Am. Soc. Hematol. Educ. Program* 35-57, 2002; Horata, et al., *Malaria J.* 8: 184, 2009, each of which is incorporated herein by reference.

The one or more target cell types can include one or more cancer cell circulating in the blood fluid or lymph fluid of the vertebrate subject. In an aspect, the cancer cells can be circulating tumor cells that have metastasized from solid tumors located elsewhere in the body. Examples of solid tumors from which metastatic cells can arise include, but are not limited to, carcinomas (e.g., adrenal, breast, cervical, colon, endometrial, lung, ovarian, pancreatic, prostate, stomach, testicular, thyroid, melanoma, head & neck) and sarcomas (e.g., brain, Ewing's sarcoma, Karposi's sarcoma, osteosarcoma, retimulum cell, spinal cord). Circulating tumor cells are indicative of metastasis and may suggest a need for changes in the treatment regime. For example, the detection of circulating tumor cells in melanoma patients who are clinically "disease-free" indicates disease recurrence, tumor cell spreading, and a high potential for distant metastasis, and enables identification of high-risk melanoma patients. See, e.g., Schuster, et al. *Clin. Cancer Res.* 13:1171-1178, 2007, which is incorporated herein by reference. The appearance of circulating tumor cells can also provide an indication of the long term prognosis for the patient. For example, breast cancer patients with levels of circulating tumor cells equal to or higher than five cells per 7.5 milliliters of blood have a shorter median progression-free survival (2.7 months vs. 7.0 months) and shorter overall survival (10.1 months versus greater than 18.0 months) as compared with breast cancer patients with less than five cells per 7.5 milliliters of blood. See, Cristofanilli et al. *N. Engl. J. Med.* 351:781-791, 2004, which is incorporated herein by reference.

In an aspect, the cancer cells can include associated with blood cancers. Examples of blood cancers include, but are not limited to, lymphoma, various types of leukemia, and multiple myeloma. Lymphoma is a cancer of lymphocytes which usually begins in a lymph node but may originate from the stomach, intestines, skin or any other organ. The two main types of lymphoma are Hodgkin's disease and non-Hodgkin's lymphoma. In Hodgkin's disease, the abnormal cells are called the Reed-Sternberg cells, characterized as large binucleated malignant cells that is an abnormal derivative of a B lymphocyte. The distinctive appearance of Reed-Sternberg cells can be seen in a biopsy specimen of lymph node tissue when examined under a microscope. This type of cancer can spread throughout the lymphatic system, affecting any organ or lymph tissue in the body. Adult non-Hodgkin's lymphoma is classified by the size, type and distribution of cancer cells in the lymph nodes. The three types are low grade (slower growing), intermediate grade, and high grade (aggressive). Low-grade lymphomas include small-lymphocytic lymphoma, follicular small-cleaved-cell lymphoma, and follicular mixed-cell lymphoma. Intermediate-grade lymphomas include follicular large-cell lymphoma, diffuse small-cleaved-cell lymphoma, diffuse mixed lymphoma, and diffuse large-cell lymphoma. High-grade lymphomas include immunoblastic lymphoma, lymphoblastic lymphoma, and small noncleaved (Burkitt's and non-Burkitt's) lymphoma. Childhood non-Hodgkin's lymphomas include lymphoblastic lymphoma, large-cell lymphoma, and small-noncleaved-cell lymphoma (including Burkitt's and non-Burkitt's lymphomas). Multiple myeloma is cancer of the bone marrow caused by the uncontrolled growth of plasma cells, a form of white blood cells. Normally, plasma cells make antibodies (e.g., immunoglobulins) to fight infections. In multiple myeloma, however, plasma cells multiply uncontrollably and make too much of a single type of immunoglobulin. The level of other types of immunoglobulin drops dangerously low, leaving the patient open to infections. The cancerous plasma cells collect in the bones and bone marrow and sometimes form tumors that destroy the bone tissue, causing the bones to become weak and possibly break.

Controlling Levels of One or More Target Cell Types to a Target Level. A device is described herein that can include one or more sensors configured to detect one or more target cell types in blood fluid or lymph fluid of the vertebrate subject and in combination with a controller in communication with the sensor is configured to control levels of the one or more target cell types to a target level in the vertebrate subject. The target level can be a desired concentration of one or more target cell types in the blood fluid or lymph fluid, or the target level can be a desired range of concentrations of one or more target cell types in the blood fluid or lymph fluid. Alternatively, the target level can be a desired ratio of concentrations of two or more target cell types in the blood fluid or lymph fluid. The desired ratio can be determined by a least squares fit of the concentrations of the two or more target cell types. The target level of a target cell can be a desired concentration and/or concentration range and/or ratio of concentrations that is a specific value or range of values such as, for example, a value or range of values observed in a normal subject. Alternatively, the target level of a target cell can be a desired concentration and/or concentration range and/or ratio of concentrations that is at least 20%, at least 40%, at least 60%, at least 80%, or at least 100% below or above the current level of the target cell in the blood fluid or lymph fluid of the vertebrate subject.

The target level of one or more target cell types can include a desired concentration and/or concentration range that is below that observed in the blood fluid or lymph fluid of the vertebrate subject experiencing a disease or condition in the vertebrate subject. Elevated levels of red blood cells are associated with exposure to carbon monoxide, long-term lung disease, kidney disease, some cancers, certain forms of heart disease, liver disease. Elevated levels of platelets are associated with bleeding, iron deficiency, some diseases like cancer, or bone marrow problems. Elevated levels of neutrophils, eosinophils, and/or lymphocytes are associated with infection, malignancy and autoimmune diseases. The desired concentration and/or concentration range can be the concentration and/or concentration range observed in a normal individual. For example, the normal range of white blood cells in men and nonpregnant women ranges from 4.5 to $11 \times 10^9$ cells per liter while in pregnant women, the white blood cell counts range from 5.9 to $25.7 \times 10^9$ cells per liter depending upon whether the subject is in the first, second or third trimester or postpartum. Similarly, normal red blood cell counts range from 4.7 to $6.1 \times 10^{12}$ cells per liter in men, 4.2 to $5.4 \times 10^{12}$ cells per liter in women, 4.0 to $5.5 \times 10^{12}$ cells per liter in children and 4.8 to $7.1 \times 10^{12}$ cells per liter in newborns. Normal platelet counts range from 150 to $450 \times 10^9$ cells per liter for children and 150 to $400 \times 10^9$ cells per liter for adults. See, e.g., Rea, WebMD. Complete Blood Count (CBC). at www.webmd.com/a-to-z-guides/complete-blood-count-cbc. Last updated Sep. 12, 2008; accessed Oct. 5, 2009; incorporated herein by reference.

The target level of one or more target cell types can include a percentage range of cells in the blood fluid or lymph fluid of the vertebrate subject. For example, of the total white blood cells in a normal subject, neutrophils range from 50% to 62%, band neutrophils range from 3% to 6%, lymphocytes range from 25% to 40%, monocytes range from 3% to 7%, eosinophils range from 0% to 3%, and basophils range from 0% to 1%.

In some pathological states such as cancer or infectious disease, the ideal target level of one or more target cell types can be zero. In the instance where a target level of zero is not attainable, the target level can be a value that reduces the symptoms and/or the disease progression. In malaria-infected individuals, for example, the degree of parasitemia is correlated with the severity of the disease. Parasites per microliter of blood are used to assess parasitemia. At a level of 100 parasites per microliter (0.002% parasitemia), the subject may just be showing symptoms. At a level of 10,000 parasites per microliter (0.2% parasitemia) immune patient will begin to exhibit symptoms. At a levels of 100,000 to 250,000 parasites per microliter (2-5%) severe malaria, increased mortality. At a level of 500,000 parasites per microliter (10%), blood transfusion should be considered, high mortality. Reducing the parasitemia, even if not to zero, may reduce symptoms.

The target level can include a desired ratio of concentrations of two or more target cell types in the blood fluid or lymph fluid as determined by a least squares fit of the concentration values of the two or more target cell types. In this instance, the levels of one or more target cell types can be altered to modulate the overall ratio of two or more target cell types. For example, the relative levels of neutrophils and leukocyte is reportedly indicative of cardiovascular risk such that increased neutrophils and/or decreased leukocytes are associated with diabetes, coronary artery disease, unstable angina, and increased risk of myocardial infarction. See, e.g., Horne, et al., *J. Am. Coll. Cardiol.* 45: 1638-1643, 2005, which is incorporated herein by reference.

Device Functioning in or Proximal to Blood Vessel and/or Lymph Vessel of a Vertebrate Subject. A device is described that can include at least one reactive component disposed in the at least one treatment region configured to modulate a physiological effect of one or more target cell types associated with a disease or condition and can further include one or more sensors for sensing one or more target cell types in the blood fluid or lymph fluid of a subject and a controller in communication with the one or more sensors for controllably diverting all or part of the blood fluid or lymph fluid through the flow route into the one or more treatment regions. The one or more treatment regions of the device include one or more reactive components to modulate a physiological effect of one or more target cell types. The device includes the controller that receives sensed data, controls diversion of blood fluid or lymph fluid flow, and controls the release of the one or more reactive components for modulating a physiological effect of one or more target cell types.

The device for modulating a physiological effect of one or more target cell types associated with a disease or condition, in whole or in part, can be configured for use in, or proximal to, one or more blood vessels and/or lymph vessels of a vertebrate subject. In an aspect, the device, in whole or in part, is an intra-vessel sized device (e.g., sufficiently small enough to be placed in a blood vessel and/or a lymph vessel while not necessarily obstructing flow). The device can be inserted into a blood vessel or lymph vessel. Configurations for the device include, but are not limited to, a substantially tubular structure, with one or more lumens in fluid communication with the blood vessel or lymph vessel of a subject. In an aspect, the device can take the form of a short cylinder, an annulus, a cylinder, and/or a spiral. See, e.g., U.S. Patent Applications 2007/0066929 and 2008/0058785; Bezrouk et al, Scripta Medica (BRNO) 78(4):219-226, 2005, each of which is incorporated herein by reference. In an aspect, the device has a cylindrical and hollow configuration, with a single central opening, optionally allowing the exterior of the cylindrical structure to contact and engage the wall of the vessel, and the interior of the structure (within the single central opening) to form a fluid-contacting portion of the device. For example, the device can be configured as a specialized stent fixed within a specific artery or vein. See, e.g., U.S. Pat. Nos. 5,411,551, 7,326,240; U.S. Patent Applications 2007/0294150, 2008/0281400; Yokota, et al., 22nd IEEE International Conference MicroElectro Mechanical Systems, Sorrento, Italy, January 25-29. IEEE pp. 495-499, 2009, each of which is incorporated herein by reference.

In an aspect, the device, in whole or in part, can be configured to be approximately hemi-spherical or hemi-ellipsoid, allowing a portion of its cross-section to contact and/or engage the internal wall of a blood or lymph vessel without significantly and/or substantially obstructing the movement of fluid within the vessel. The device can include one or more wall-engaging components including, but are not limited to, rotating wheels, projections (e.g. arms), springs, hooks (e.g. claws), suction cups, and/or tissue adhesives that are configured to engage wall portions.

In an aspect, the device can be configured in a pill- or capsule-shape, and configured to move through a central portion of a blood vessel or lymph vessel of the vertebrate subject. The device can engage a wall of the blood vessel or lymph vessel using one or more engaging components and/or freely travel through the blood and/or lymph systems. See, e.g., U.S. Patent Application 2007/0156211 A1, which is incorporated herein by reference. The device can be targeted to a site of disease (e.g., inflammation, infectious disease, or neoplastic disease) in the subject. In an aspect, the device including one or more sensors can detect elevated levels of one or more target cell types in the blood or lymphatic system of the subject and can target and form a stationary location at, or near, a site of disease or condition in the blood or lymph circulation of the vertebrate subject. In an aspect, the implantable device can be incorporated into a shunt, for example, an arteriovenous shunt inserted between an artery and a vein.

In an aspect, the device, in whole or in part, can be positioned proximal to a blood vessel or lymph vessel. "Proximal to" can refer to a space or area near to a blood vessel or lymph vessel. Locations that are proximal to a vessel can include, for example, locations external to the vessel wall where there is space for implanting one or more devices in whole or in part, and optionally to facilitate external access to the devices in whole or in part. In an aspect, "proximal to" can include distances such as, but not limited to, approximately 0.1, 1.0, 10, and/or 100 μm and/or approximately 0.1, 1.0, 10, and/or 100 mm, and can optionally include larger and/or smaller distances depending on, for example, the availability of space and the size of the device and/or the vessel.

In an aspect, the device can be configured as a self-contained unit that can include all functionalities necessary for operation of the device. In an aspect, the system is configured as one or more components, e.g., one or more sensors, controllers, treatment regions, reactive components, flow routes, reservoirs, data-collecting devices, or power sources, in one or more locations separate from one another, wherein one or more of the components can include one or more essential and/or non-essential functionalities. For example, one component of the system can be placed within a blood vessel, and another component of the system placed proximal to the blood vessel optionally in a location more accessible from the exterior of the subject, or where there is additional space. A remote portion can be configured to provide for monitoring of the vessel portion of the system, data collection, or data analysis, and/or remote-control of one or more other functions of the system such as sensing target cell types, controlling flow through a flow route, and releasing a reactive component. The remote portion can be at a separate location within the body of the subject, or outside the body of the subject. Data and/or power signals can be transmitted between the one or more components of the device using electromagnetic signals, or electrical or optical links.

The dimensions and mechanical properties (e.g., rigidity) of the device can be configured for compatibility with the location of use in order to provide for reliable positioning and/or to provide for movement of the device while preventing damage to the vessel, the vessel lumen, and/or internal location and its surrounding structure. The choice of structural component size and configuration appropriate for a particular blood vessel or lymph vessel location can be selected by a person of skill in the art, optionally a medical professional. Structural components of the device can be constructed using a variety of manufacturing methods, from a variety of biocompatible materials. Appropriate materials include metals, ceramics, polymers, and composite materials having suitable biocompatibility, sterilizability, mechanical, and physical properties. Examples of materials and selection criteria are described, for example, in *The Biomedical Engineering Handbook* (Second Edition, Volume I, J. D. Bronzino, Ed., Copyright 2000, CRC Press LLC, pp. IV-1-43-22), which is incorporated herein by reference. Manufacturing techniques can include, but are not limited to, injection molding, extrusion, die-cutting, rapid-prototyping, and will depend on the choice of material and device size and configuration. Sensing and energy-emitting portions of the devices as well as associated control circuitry can be fabricated on the structural elements using various microfabrication and/or MEMS techniques or can be constructed separately and subsequently assembled to the structural elements, as one or more distinct components. See, e.g., U.S. Patent Applications 2005/0221529, 2005/0121411, 2005/0126916, 2007/0066939, 2007/0225633 and Nyitrai, et al. "Preparing Stents with Masking & Etching Technology" $26^{th}$ International Spring Seminar on Electronics Technology pp. 321-324, IEEE, 2003, each of which is incorporated herein by reference.

In additional to biocompatible materials described and incorporated herein above, flexible material having adjustable diameter, taper, and length properties can be used as part of the structural material. For example, some materials can change from a longer, narrower configuration, to a shorter, wider configuration, or can taper over their length, e.g., shape-memory polymers that can move from one shape to another in response to a stimulus such as heat. Structural elements that can exhibit this type of expansion/contraction property can include self-expanding material, resilient material, and/or mesh structures formed of various metals, e.g., ionic polymer-metal composites (IPMC), or plastics, and some polymeric materials, e.g., hydrogels, nitinol, or polyester. See, e.g. Bellin et al., *Proc. Natl. Acad. Sci. USA*. 103: 18043-18047, 2006; and Shahinpoor et al., *Smart Mater. Struct.* 14:197-214, 2005, each of which are incorporated herein by reference.

Sensors for Measuring Target Cell Types in blood Fluid or Lymph Fluid of a Vertebrate Subject. A device is described that includes one or more sensors configured to function in, or proximal to, one or more of a blood vessel or lymph vessel of the vertebrate subject. The one or more sensors can be configured to detect one or more target cell types in one or more of blood fluid or lymph fluid of the vertebrate subject. The one or more sensors can be configured for qualitatively and/or quantitatively measuring the one or more target cell types in the blood fluid or lymph fluid of a vertebrate subject. The one or more sensors can include, but are not limited to, a biosensor, a chemical sensor, a physical sensor, an optical sensor, or a combination thereof. The one or more sensors can include one or more recognition elements that recognize one or more target cell types, e.g., one or more of an aptamer, an antibody, a receptor, a recognition-based substrate, an aptamer-based substrate, an antibody-based substrate, surface plasmon resonance, genetically modified cells, or genetically modified cells with receptor-linked signaling. The interaction of one or more target cell types with one or more sensors results in one or more detectable signals. Preferably the one or more sensors measure in real-time the levels of one or more target cell types in the blood fluid or lymph fluid of the vertebrate subject.

The one or more sensors can sense or detect one or more target cell types that include, but not limited to, blood cells (e.g., red blood cells, platelets, lymphocytes, monocytes, neutrophils, eosinophils, basophils), virus-infected cells (e.g., cells infected with human immunodeficiency virus (HIV), hepatitis B, hepatitis C, or hepatitis D), bacteria (e.g., *Staphylococcus, Streptococcus, Pseudomonas, Haemophilus, Listeria, Escherichia coli*), fungi, (e.g., *Candida albicans, Candida glabrata, Aspergillus, T. glabrata, Candida tropicalis, C. krusei*, and *C. parapsilosis*) parasites (e.g., *Trypanosoma cruzi, Trypanosoma brucei, Leishmania, Plasmodium, Babe-*

*sia microti, Toxoplasma gondii*) and cancer cells (e.g., metastatic tumor cells, hematopoietic cancer cells).

The one or more recognition elements that can recognize one or more target cell types in the blood can include, but are not limited to, antibodies, antibody fragments, peptides, oligonucleotides, DNA, RNA, aptamers, protein nucleic acids proteins, receptors, receptor ligands, lectins, viruses, enzymes, receptors, bacteria, cells, cell fragments, inorganic molecules, organic molecules, or combinations thereof. The one or more recognition elements can be associated with one or more substrate integrated into the one or more sensors.

The one or more recognition elements can be configured to recognize one or more biomolecules on the surface of the one or more target cell types. In an aspect, the one or more recognition elements can be configured to recognize one or more receptor types on the surface of target cell types. Examples of receptors include, but are not limited to, acetylcholine receptors, adenosine receptors, adrenoceptors, GABA receptors, angiotensin receptors, cannabinoid receptors, cholecystokinin receptors, dopamine receptors, glucagon receptors, glucocorticoid receptors, glutamate receptors, histamine receptors, mineralocorticoid receptors, olfactory receptors, opioid receptors, purinergic receptors, secretin receptors, serotonin receptors, somatostatin receptors, steroid hormone receptors, calcium-sensing receptor, hormone receptors, erythropoietin receptor, and natriuretic peptide receptors. Other examples include type I cytokine receptors (e.g., type 1 interleukin receptors, erythropoietin receptor, GM-CSF receptor, G-CSF receptor, growth hormone receptor, oncostatin M receptor, leukemia inhibitory factor receptor); type II cytokine receptors (e.g., type II interleukin receptors, interferon-α/β receptors, interferon-γ receptor); members of the immunoglobulin superfamily (e.g., interleukin-1 receptor, CSF1, c-kit receptor, interleukin-18 receptor); tumor necrosis factor (TNF) receptor family (e.g., TNF receptor 1 (TNF-R1), TNF receptor 2 (TNF-R2), CD27, CD40, and lymphotoxin β receptor); chemokine receptors including serpentine CCR and CXCR receptors (e.g., CCR1 and CXCR4, and interleukin-8 receptor); TGF β receptors. See Ozaki and Leonard, *J. Biol. Chem.* 277:29355-29358, 2002, which is incorporated herein by reference.

In an aspect, the one or more recognition elements can be configured to recognize other biomolecules on the surface of blood cells including but not limited to various CD (cluster of designation/cluster of differentiation) markers, intergrins, ion channels, ATPases, cell adhesion molecules, integral membrane glycoproteins, immunoglobulins, transporters. The one or more recognition elements can be configured to recognize components of cell surface biomolecules including amino acid sequence and oligosaccharide modifications.

In an aspect, the recognition element can be configured to recognize a biomolecule associated with a tumor cell. Examples of tumor associated components can include, but are not limited to, BLyS receptor, carcinoembryonic antigen (CA-125), CD25, CD34, CD33 and CD123 (acute myeloid leukemia), CD20 (chronic lymphocytic leukemia), CD19 and CD22 (acute lymphoblastic leukemia), CD30, CD40, CD70, CD133, 57 kD cytokeratin, epithelial specific antigen, epithelial cell adhesion molecule (EpCAM), extracellular matrix glycoprotein tenascin, Fas/CD95, folate receptor, gastrin-releasing peptide-like receptors, hepatocyte specific antigen, human gastric mucin, human milk fat globule, lymphatic endothelial cell marker, matrix metalloproteinase 9, melan A, melanoma marker, mesothelin, mucin glycoproteins (e.g., MUC1, MUC2, MUC4, MUC5AC, MUC6), prostate specific antigen, prostatic acid phosphatase, PTEN, renal cell carcinoma marker, RGD-peptide binding integrins, sialyl Lewis A, six-transmembrane epithelial antigen of the prostate (STEAP), TNF receptor, TRAIL receptor, tyrosinase, villin. Other tumor associated antigens include, but are not limited to, alpha fetoprotein, apolipoprotein D, clusterin, chromogranin A, myeloperoxidase, MyoD1 myoglobin placental alkaline phosphatase c-fos, homeobox genes.

In an aspect, a detectable label including tumor cell-associated recognition elements can be used. Many are available from a commercial source. For example, lectins concanavalin A and wheat germ agglutinin are available conjugated to Alexa fluors, Marina Blue, AMCA, Oregon Green, tetramethylrhodamine, Texas Red, fluorescein (from, Invitrogen, Carlsbad, Calif.). Other lectins conjugated to fluorescent dyes are available including *Phaseolus vulgaris* lectin (PHA-L), *Arachis hypogaea* lectin (PNA), *Helix pomatia* agglutinin (HPA), Soybean agglutinin (SBA), and lectins from *Griffonia simplicifolia* (from, Invitrogen, Carlsbad, Calif.). Magnetic beads with an antibody to the human epithelial antigen, EpCAM (epithelial cell adhesion molecule) are commercially available (from, e.g., Dynal Biotech, Brown Deer, Wis.). EpCAM can be used to selectively bind circulating tumor cells of epithelial origin in the blood fluid or lymph fluid of a vertebrate subject. Anti-CA-125 (anti-carcinoembryonic antigen) antibodies can be used to selectively bind circulating tumor cells of ovarian cancer origin in the blood fluid or lymph fluid of a mammalian subject. Anti-CA125 antibodies can be conjugated to rhodamine-X (Invitrogen, Eugene, Oreg.). Anti-FR (anti-folate receptor) antibodies and folate-FITC, folate-Tc99m can be used to selectively bind circulating tumor cells that overexpress folate receptors, e.g., ovarian cancer cells, and circulating tumor cells in the blood fluid or lymph fluid of a mammalian subject. Endocyte, Inc., West Lafayette, Ind. See, e.g., He, et al., *Proc. Natl. Acad. Sci. USA* 104: 11760-11765, 2007, which is incorporated herein by reference.

In an aspect, the recognition element can be configured to recognize a biomolecule associated with the surface of a pathogen in which the pathogen is a bacteria, a virus, a fungus, or a parasite. The biomolecule can be one or more components of the bacterial outer membrane, cell wall, and/or cytoplasmic membrane, for example. Examples of target components associated with the bacterial outer membrane of Gram-negative bacteria include, but are not limited to, lipopolysaccharide and OMP (outer membrane protein) porins, the latter of which are exemplified by OmpC, OmpF and PhoP of *E. coli*. Examples of target components associated with the bacterial cell wall of both Gram-positive and Gram-negative bacterial include, but are not limited to, peptidoglycans polymers composed of an alternating sequence of N-acetylglucoamine and N-acetyl-muraminic acid and crosslinked by amino acids and amino acid derivatives. Examples of target components associated with the bacterial cytoplasmic membrane include, but are not limited to, the MPA1-C (also called polysaccharide copolymerase, PCP2a) family of proteins, the MPA2 family of proteins, and the ABC bacteriocin exporter accessory protein (BEA) family of proteins. Other examples of target components associated with bacteria include, but are not limited to, transporters, e.g., sugar porter (major facilitator superfamily), amino-acid/polyamine/organocation (APC) superfamily, cation diffusion facilitator, resistance-nodulation-division type transporter, SecDF, calcium:cation antiporter, inorganic phosphate transporter, monovalent cation:proton antiporter-1, monovalent cation:proton antiporter-2, potassium transporter, nucleobase:cation symporter-2, formate-nitrite transporter, divalent anion:sodium symporter, ammonium transporter, and multi-antimicrobial extrusion; channels, e.g., major intrinsic protein, chloride channel, and metal ion transporter; and primary active transporters, e.g., P-type ATPase, arsenite-antimonite efflux, Type II secretory pathway (SecY), and sodium-transporting carboxylic acid decarboxylase. A number of other potential target components associated with bacteria have been described in Chung, et al., *J. Bacteriology* 183:1012-1021, 2001, which is incorporated herein by reference.

In an aspect, the recognition element can be configured to recognize a biomolecule associated with a pathogen-infected blood cell. In some instances, the recognition element can be a biomolecule expressed on the surface of the cell that is derived from the pathogen. For example, red blood cells infected with *P. falciparum* can be distinguished from normal red blood cells by changes in surface protein expression including expression on the red blood cell surface of the parasite derived protein *P. falciparum* erythrocyte membrane protein (PfEMP1). See, e.g., Horata, et al., *Malaria J.* 8:184, 2009, which is incorporated herein by reference.

The device including one or more sensors configured to detect one or more target cell types can incorporate one or more recognition elements and one or more measurable fluorescent-signal producing elements. In an aspect, the one or more target cell types in the blood fluid or lymph fluid of the vertebrate subject is captured by a recognition element and further reacted with one or more fluorescent-producing second elements. The fluorescence associated with the captured target cell can be measured using fluorescence spectroscopy. Alternatively, the fluorescence signal can be detected using at least one charged-coupled device (CCD) and/or at least one complimentary metal-oxide semiconductor (CMOS).

In an aspect, the one or more sensors can use Förster or fluorescence resonance energy transfer (FRET) to sense one or more target cell types in the blood fluid or lymph fluid of the vertebrate subject. FRET is a distance-dependent interaction between the electronic excited states of two dye molecules in which excitation is transferred from a donor molecule to an acceptor molecule without emission of a photon. In an aspect, interaction of a donor molecule with an acceptor molecule results in a shift in the emission wavelength associated with excitation of the acceptor molecule. In an aspect, interaction of a donor molecule with an acceptor molecule in results in quenching of the donor emission. The one or more recognition elements associated with the one or more sensors can include at least one donor molecule and at least one acceptor molecule. Binding of one or more target cell types to the recognition element results in a conformation change in the recognition element, leading to changes in the distance between the donor and acceptor molecules and changes in measurable fluorescence. The recognition element can be a cell, an antibody, an aptamer, a receptor or any other molecule that changes conformation or signaling in response to binding a target.

A variety of donor and acceptor fluorophore pairs can be considered for FRET associated with the recognition element including, but not limited to, fluorescein and tetramethylrhodamine; IAEDANS and fluorescein; fluorescein and fluorescein; and BODIPY FL and BODIPY FL. A number of Alexa Fluor (AF) fluorophores (Molecular Probes-Invitrogen, Carlsbad, Calif., USA) can be paired with other AF fluorophores for use in FRET. Some examples include, but are not limited, to AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

The cyanine dyes Cy3, Cy5, Cy5.5 and Cy7, which emit in the red and far red wavelength range (>550 nm), offer a number of advantages for FRET-based detection systems. Their emission range is such that background fluorescence is often reduced and relatively large distances (>100 Å) can be measured as a result of the high extinction coefficients and good quantum yields. For example, Cy3, which emits maximally at 570 nm and Cy5, which emits at 670 nm, can be used as a donor-acceptor pair. When the Cy3 and Cy5 are not proximal to one another, excitation at 540 nm results only in the emission of light by Cy3 at 590 nm. In contrast, when Cy3 and Cy5 are brought into proximity by a conformation change in an aptamer, antibody, receptor, affibody, mimic, nucleic acid, or synthetic compound, for example, excitation at 540 nm results in an emission at 680 nm. Semiconductor quantum dots (QDs) with various excitation/emission wavelength properties can also be used to generate a fluorescence based sensor.

Quenching dyes can be used as part of the binder element to quench the fluorescence of visible light-excited fluorophores. Examples include, but are not limited, to DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs can be considered for FRET associated with the recognition element including, but not limited to, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

The device including one or more sensors configured to detect one or more target cell types can use the technique of surface plasmon resonance (for planar surfaces) or localized surface plasmon resonance (for nanoparticles). Surface plasmon resonance involves detecting changes in the refractive index on a sensor surface in response to changes in molecules bound on the sensor surface. In an aspect, the surface of the sensor is a glass support or other solid support coated with a thin film of metal, for example, gold. In an aspect, the sensor surface can include a matrix to which is immobilized one or more recognition elements that recognize one or more target cell types. The recognition elements can be antibodies or fragments thereof, oligonucleotide or peptide based aptamers, receptors or ligands, artificial binding substrates formed by molecular imprinting, or any other examples of molecules and/or substrates that bind cells. As blood or blood components from the subject passes by the sensor surface, a target cell interacts with recognition elements on the sensor surface. The sensor is illuminated by monochromatic light. Resonance occurs at a specific angle of incident light. The resonance angle depends on the refractive index in the vicinity of the surface, which is dependent upon the concentration of molecules on the surface. An example of instrumentation that uses surface plasmon resonance is the BIACORE® surface plasmon resonance system (Biacore, Inc. —GE Healthcare, Piscataway, N.J.) which includes a sensor microchip, a laser light source emitting polarized light, an automated fluid handling system, and a diode array position sensitive detector. See, e.g., Raghavan & Bjorkman *Structure* 3:331-333, 1995, which is incorporated herein by reference.

The one or more sensors configured to detect one or more target cell types can be one or more label-free optical biosensors that incorporate other optical methodologies, e.g., interferometers, waveguides, fiber gratings, ring resonators, and photonic crystals. See, e.g., Fan, et al., *Anal. Chim. Acta* 620:8-26, 2008, which is incorporated herein by reference.

The device including one or more sensors configured to detect one or more target cell types can include one or more microcantilevers. A microcantilever can act as a biological sensor by detecting changes in cantilever bending or vibrational frequency in response to binding of one or more target cell types to the surface of the sensor. In an aspect, the sensor can be bound to a microcantilever or a microbead as in an immunoaffinity binding array. In an aspect, a biochip can be formed that uses microcantilever bi-material formed from gold and silicon, as sensing elements. See, e.g. Vashist, *J. Nanotech Online* 3:DO: 10.2240/azojono0115, 2007, which is incorporated herein by reference. The gold component of the microcantilever can be coated with one or more recognition elements which upon binding one or more target cell types causes the microcantilever to deflect. Aptamers or antibodies specific for one or more target cell types can be used to coat microcantilevers. See, e.g., U.S. Pat. No. 7,097,662, which is incorporated herein by reference. The one or more sensor can incorporate one or more methods for microcantilever deflection detection including, but not limited to, piezoresistive deflection detection, optical deflection detection, capacitive deflection detection, interferometry deflection detection, optical diffraction grating deflection detection, and charge coupled device detection. In an aspect, the one or more microcantilever can be a nanocantilever with nanoscale components. The one or more microcantilevers and/or nanocantilevers can be arranged into arrays for detection of one or more target cell types. Both microcantilevers and nanocantilevers can find utility in microelectomechnical systems (MEMS) and/or nanoelectomechanical systems (NEMS).

The device including one or more sensors configured to detect one or more target cell types can include a field effect transistor (FET) based biosensor. In an aspect, a change in electrical signal is used to detect interaction of one or more analytes with one or more components of the sensor. See, e.g., U.S. Pat. No. 7,303,875, which is incorporated herein by reference.

The device including one or more sensors configured to detect one or more target cell types can incorporate electrochemical impedance spectroscopy. Electrochemical impedance spectroscopy can be used to measure impedance across a natural and/or artificial lipid bilayer. The sensor can incorporate an artificial bilayer that is tethered to the surface of a solid electrode. One or more receptor can be embedded into the lipid bilayer. The one or more receptors can be ion channels that open and close in response to binding of a specific analyte. The open and closed states can be quantitatively measured as changes in impedance across the lipid bilayer. See, e.g., Yang, et al., IEEE SENSORS 2006, EXCO, Daegu, Korea/Oct. 22-25, 2006, which is incorporated herein by reference.

The one or more sensors configured to detect one or more target cell types can include cells having one or more binding elements which when bound to one or more target cell types induce a measurable or detectable change in the cells. The cells having one or more binding elements can emit a fluorescent signal in response to interacting with one or target cell types. For example, a bioluminescent bioreporter integrated circuit can be used in which binding of a ligand to a cell induces expression of reporter polypeptide linked to a luminescent response. See, e.g., U.S. Pat. No. 6,673,596, [Durick & Negulescu *Biosens. Bioelectron.* 16:587-592, 2001] each of which is incorporated herein by reference. Alternatively, the one or more cell can emit an electrical signal in response to interacting with one or more target cell types. In an aspect, an implantable biosensor can be used which is composed of genetically modified cells that responded to target binding by emitting a measurable electrical signal. See U.S. Patent Application 2006/0234369 A1; which is incorporated herein by reference.

The device can further include one or more sensors configured to detect one or more target cell types wherein the one or more sensors are configured to detect one or more physiological parameters in the vertebrate subject. Examples of physiological parameters include, but are not limited to, body temperature, respiration rate, pulse, blood pressure, edema, oxygen saturation, pathogen levels, or toxin levels.

In an aspect, the device can include one or more sensor that optically images the one or more target cell types. The one or more target cell types can be detected using any of a number of imaging or optical methods including but not limited to light scattering, electrical impedance, infrared spectroscopy, acoustic imaging, thermal imaging, photothermal imaging, dark field, visible light absorption and refraction, and autofluorescence. See, e.g., U.S. Patent Application 2009/0093728; Doornbos et al. *Cytometry* 14:589-594, 1993; Gao et al. Proceedings of the 25$^{th}$ Annual International Conference of the IEEE EMBS, Cancun, Mexico, Sep. 17-21, 2003; Oberreuter et al. *Int. J. Syst. Evol. Microbiol.* 52:91-100, 2002; Baddour et al. Ultrasonics Symposium IEEE 2:1639-1644, 2002; Zharov et al. *J. Cell. Biochem.* 97:916-932, 2006; Zharov et al. *J. Biomed. Opt.* 11:054034-1-4, 2006; Koenig et al. *J. Fluoresc.* 4:17-40, 1994; which are each incorporated herein by reference. As an example, red blood cells infected with the parasite *Plasmodium falciparum* can be differentiated from other cells in the blood fluid or lymph fluid using differential light scatter at 10 degrees (complexity) and polarized light scatter at 90 degrees (lobularity) based on the pigmentation of the parasite. See, e.g., Mendelow et al. *Br. J. Haematology* 104:499-503, 1999, which is incorporated herein by reference.

In an aspect, forward light scattering of the one or more target cell types can provide an indication of cell size while side light scattering of the one or more target cell types can provide an indication of cellular granularity, membrane complexity, and number of organelles. Lymphocytes, monocytes, granulocytes, red blood cells can be differentiated from one another under conditions of flow using forward and side light scattering under conditions of flow. See, e.g., Terstappen et al. *Cytometry* 9:39-43, 1988; U.S. Pat. No. 7,264,794; each of which is incorporated herein by reference. Differential light scattering can also be used to detect circulating tumor cells based on the size differential relative to other components of the blood. Neutrophils, red bloods cells, and platelets are 10.5-12.5 microns, 7-8 microns, and 3 microns, respectively while the average size of circulating tumor cells range from 18.3 to 20.6 microns in diameter. See, e.g., Moore et al. *Cancer* 13:111-117, 1960; Mohamed et al. *IEEE Transactions on Nanobioscience,* 3:251-256, 2004; each of which is incorporated herein by reference. In some aspect, a pathogen is detected in the blood fluid or lymph fluid based on size analysis and scattering. For example, *Trypanosoma brucei gambiense*, a blood borne protozoan associated with African sleeping sickness, has a unique elongated cellular shape 25-40 microns in length with a flagellum and very distinct from the predominantly spherical shape of normal cellular components of the blood. Blood cells infected with the parasite *Plasmodium falciparum* can be differentiated from other cells in the vasculature using differential light scatter at 10 degrees (complexity) and polarized light scatter at 90 degrees (lobularity) based on the pigmentation of the parasite (Mendelow et al. (1999) Br. J. Haematology 104:499-503).

In an aspect, the device including one or more sensors can detect the one or more target cell types based on electrical impedance. Cellular components of the blood can be differentiated based on volume using electrical impedance as commonly practiced using a Coulter counter. A MEMS resembling a miniaturized Coulter counter can be incorporated into the device described herein and can be constructed using thin platinum electrodes with a sensing zone of, for example, 20-100 microns (see, e.g., Zheng et al. (2006) Proceedings of 2006 International Conference on Microtechnologies in Medicine and Biology, IEEE, Okinawa, Japan, 9-12 May, 2006; Gao et al. (2003) Proceedings of the 25$^{th}$ Annual International Conference of the IEEE EMBS, Cancun, Mexico, Sep. 17-21, 2003).

In an aspect, the device including one or more sensors can detect the one or more target cell types based on autofluorescence. A pathogen or pathogens can be detected in the vasculature via autofluorescence induced by electromagnetic energy. Naturally-occurring autofluorescence in bacteria is derived from biomolecules containing fluorophores, such as porphyrins, amino acids tryptophan, tyrosine, and phenylalanine, and the coenzymes NADP, NADPH, and flavins. See, e.g., Koenig et al. *J. Fluoresc.* 4:17-40, 1994; Kim et al. *IEEE/EMB Magazine* January/February 122-129, 2004, each of which is incorporated herein by reference. Bacteria can be detected using fluorescence lifetimes measured at 280-540 nm after excitation at 250-450 nm. See, e.g., Bouchard et al. *J. Biomed. Opt.* 11:014011, 2006, which is incorporated herein by reference. For example, *Streptococcus pneumoniae*, can be detected using fluorescence spectroscopy at excitation wavelengths of 250 and 550 nm and emission wavelengths of 265 and 700 nm. See, e.g., Ammor *J. Fluoresc.* 17:455-459, 2007, which is incorporated herein by reference. Autofluorescence can also be used to detect members of the fungi family. *Candida albicans* and *Aspergillus niger* autofluoresce at wavelengths ranging from 515 nm to 560 nm when irradiated with electromagnetic energy at wavelengths of 465-495 nm. See, e.g., Mateus et al. *Antimicrob. Agents and Chemother.* 48:3358-3336, 2004; Sage et al. *American Biotechnology Laboratory* 24:20-23, 2006, each of which is incorporated herein by reference. Autofluorescence associated with the food vacuole of the malaria parasite *Plasmodium* spp. can used to detect infected red blood cells with in the blood stream See, e.g., Wissing et al. *J. Biol. Chem.* 277:37747-37755, 2002, which is incorporated herein by reference.

In an aspect, the one or more sensors configured to detect one or more target cell types present in the blood fluid or lymph fluid of a vertebrate subject can recognize the one or more target cell types based on a spectral analysis. Alternatively or additionally, the one or more target cell types can be recognized based on pattern and image recognition analysis. Various methods have been described for image and shape analysis of cells and subcellular components of cells. See, e.g., U.S. Pat. Nos. 5,107,422; 5,790,691; 6,956,961 B2; 7,151,847 B2; U.S. Patent Applications 2005/0251347 A1; 2006/0039593 A1; Fei-Fei et al. *IEEE Transactions on Pattern Analysis and Machine Intelligence* 28:594-611, 2006; Martin et al. *IEEE Transactions on Pattern Analysis and Machine Intelligence* 26:530-549, 2004; Olson et al. *Proc.* *Natl. Acad. Sci. USA* 77:1516-1520, 1980; Schneider, et al *Biorheology* 32:237-238, 1995; which are each incorporated herein by reference. For example, a "Texture Analyzing System" can be used to distinguish various target cell types in the blood fluid or lymph fluid of the vertebrate subject based on the granularity of the target cell types. See, e.g., Bins et al. *Cytometry* 1:321-324, 1981, which is incorporated herein by reference. The imaged components of the target cell types are measured with a gray scale with 33 intervals ranging from black (level 0) to white (level 99) and a histogram is generated. Mature white blood cells (neutrophils, eosinophils, basophils and lymphocytes) have a dense nuclear structure and therefore low counts. In contrast, monocytes have a looser, less dense nuclear structure and high counts. The cytoplasm of eosinophils and neutrophils is very granular and is reflected in the combination of high positive and low negative counts. Smaller values are seen in the cytoplasm of lymphocytes, monocytes and basophils. Similarly, granulometries can be used to identify red blood cells infected with the malarial parasite. See, e.g., Dempster & DiRuberto *Circuits and Systems,* 2001. ISCAS 2001. The 2001 IEEE International Symposium on May 6-9, 2001, 5:291-294, which is incorporated herein by reference.

Device Including a Controller In Communication With and Responsive to a Sensor. A device is described that can further include a controller in communication with one or more sensors and configured to be informed by the one or more sensors. The controller can be configured to control flow of the one or more of blood fluid or lymph fluid through at least one lumen in response to the one or more sensors. The one or more sensors is operably coupled to the controller, either wirelessly or by circuit, and can transmit data to the controller regarding the detection and/or levels (relative or absolute) of one or more target cell types in the blood fluid or lymph fluid of the vertebrate subject. The controller can be integrated into the device. Alternatively, the controller can be a separate component of the device that receives and transmits data and/or commands either wirelessly or through wires. For example, an implanted device can send data regarding the sensed levels of one or more target cell types to an external controller through a wireless signal.

The device including the sensor and the controller can compare the input data regarding the one or more target cell types in the blood of the vertebrate subject with stored data. The controller itself can include the stored data, or the data can be stored off site and coupled either wirelessly or by circuit to the sensor and the controller. Alternatively or additionally, the controller can have access to one or more remote databases that include the stored data. The stored data can be data regarding the normal level of one or more target cell types in normal or healthy subjects without a disease, condition, or infection. The stored data can further include data regarding the baseline level of one or more target cell types in a subject prior to onset of a disease or condition. The stored data can further include data regarding the level of one or more target cell types in a subject at one or more previous time points. The controller assesses the most recently obtained input data with the stored data and is configured to controllably initiate steps to modulate a physiological effect of one or more target cell types in the blood fluid or lymph fluid of the vertebrate subject.

In response to input data, the device including the sensor and the controller can cause the device to controllably divert all or part of the blood of a subject into one or more treatment regions. Access to one or more treatment regions can be controlled by at least one flow-modulating element. A flow-modulating element can be a gate, a valve, a louver, a splitter or flow divider, a filter, a baffle, a channel restriction, a retractable iris, or other structure that controllably limits or permits access of the blood flow to a treatment region. The controller is operably coupled, either wirelessly or by circuit, to at least one flow-modulating element. The controller can send a signal to the at least one flow-modulating element indicating whether or not all or part of the flow of blood should be diverted into a treatment region.

The device including the sensor and the controller can further controllably initiate release or activation of one or more reactive components designed to modulate a physiological effect of the one or more target cell types. The one or more reactive component is one or more of a cell-disrupting agent, a binding agent, an energy source, a cytotoxic agent, a cytostatic agent, a programmed cell death-inducing agent, a chemotherapeutic agent, an antibody-toxin agent, or a combination thereof. The one or more reactive components can be controllably released or activated by the controller in the one or more treatment regions of the device. In an aspect, the controller can release one or more reactive component into the blood fluid or lymph fluid of the vertebrate subject to modulate the activity and/or expression of the one or more target cell types. Alternatively or additionally, the controller can send data regarding the levels of one or more target cell types in the blood fluid or lymph fluid to the subject, to one or more third party individuals such as a physician or other caregiver, to a computing device, or to a combination thereof. The subject and/or caregiver or computing device can choose to initiate steps to modulate a physiological effect of one or more target cell types, to release reactive components into the circulation, into the treatment region, or a combination thereof.

The device including the controller can also include a processor or non-volatile memory structure including one or more algorithms residing on the memory that provide computational models of a disease or condition. For example, a computational model of a disease or condition can include information regarding a variety of interrelated cellular pathways involved in the disease process. The computational model can further inform decisions made by the controller. Examples of computational models related to inflammatory disease, cancer and pathogen infection have been described. See, e.g., U.S. Pat. No. 7,415,359 B2; U.S. Patent Applications 2007/0083333 A1, 2008/0201122 A1; Vodovotz, et al., *Curr. Opin. Crit. Care.* 10:383-390, 2004; Zenker, et al., *PLoS Comput. Biol.* 3(11):e204, 2007; Li, et al., *PLoS ONE* 3(7):e2789, 2008; Vodovotz, et al., *PLoS Comput. Biol.* 4:e1000014, 2008; An, *Theoretical Biology Medical Modeling* 5:11, 2008; Lee, et al., *Proc. Natl. Acad. Sci. USA.* 104: 13086-13091, 2007, Zhou, et al., *HIV Medicine.* 6:216-223, 2005, each of which is incorporated herein by reference.

Device Including One or More Reactive Components. A device is described herein that includes one or more sensors configured to detect one or more target cell types in one or more of blood fluid or lymph fluid of the vertebrate subject, at least one controller, and at least one reactive component disposed in the at least one treatment region, the at least one reactive component configured to modulate a physiological effect of the one or more target cell types in the vertebrate subject. The at least one reactive component configured to modulate a physiological effect of the one or more target cell types can be responsive to the controller, wherein the controller can be configured to open or close the at least one controllable flow barrier in response to the one or more sensor and configured to control interaction between one or more reactive components and the one or more target cell types. The controller can be configured to adjust the at least one reactive component disposed in the at least one treatment region to achieve a target level of the detected one or more target cell types in the one or more of blood fluid or lymph fluid of the vertebrate subject. A reactive component can include, but is not limited to, a cell-disrupting agent, a binding agent, an energy source, a cytotoxic agent, a cytostatic agent, a programmed cell death-inducing agent, a chemotherapeutic agent, an antibody-toxin agent, or a combination thereof. A reactive component can further include a modulator that modulates the activity of one or more target cell types. The one or more reactive components can be incorporated into or released within one or more treatment regions associated with the device. Alternatively, the one or more reactive components can be diffusible components released from a reservoir of the device into the blood fluid or lymph fluid of the vertebrate subject.

Binding Agents as Reactive Components to Remove One or More Target Cell Types from the Blood Fluid or Lymph Fluid of the Vertebrate Subject. The device can further include one or more reactive components that can include binding agents designed to remove one or more target cell types from the blood fluid or lymph fluid of the vertebrate subject. The one or more binding agents can be used alone to selectively or non-selectively sequester one or more target cell types. Alternatively, the one or more binding agents can be used to capture one or more target cell types in combination with treatment including one or more additional reactive components, e.g., a second binding agent, a cell-disrupting agent, an energy source, a cytotoxic agent, a cytostatic agent, a programmed cell death-inducing agent, a chemotherapeutic agent, an antibody-toxin agent, or a combination thereof. Following binding of the one or more target cell types to the one or more binding agents in a treatment region, one or more additional reactive components can be provided to modulate a physiological effect of the one or more target cell types.

The one or more reactive components including the one or more binding agents can be configured to non-selectively bind one or more target cell types. For example, the binding agents can constitute all or part of one or more components of extracellular matrix, e.g., fibronectin, vitronectin, collagen, and laminin. Cells expressing integrins and other cell surface components will non-selectively bind to the extracellular matrix components. Alternatively, the binding agents can constitute all or part of one or more components of basal lamina, e.g., collagen, heparan sulfate proteoglycan, laminin, integrins, dystroglycans. Cells expressing cell adhesion molecules and other cell surface components will non-selectively bind to the one or more components of basal lamina. In an aspect, the binding agent can be one or more of a commercially available cell adhesion product (e.g., BD MATRIGEL™ from, BD Biosciences, San Jose, Calif.). In an aspect, the one or more binding agent can be a surface substrate that non-selectively binds target cell types, examples of which include, but are not limited to, glass and plastic.

The one or more reactive components including the one or more binding agents can be configured to selectively bind one or more target cell types. A selective binding agent of one or more target cell types can include, but is not limited to, antibodies, antibody fragments, peptides, oligonucleotides, DNA, RNA, aptamers, protein nucleic acids proteins, receptors, receptor ligands, lectins, viruses, enzymes, receptors, bacteria, cells, cell fragments, inorganic molecules, organic molecules, an artificial binding substrate formed by molecular imprinting, or other examples of biomolecules and/or substrates that bind cells.

The one or more reactive components including the one or more binding agents can include one or more antibodies that bind one or more target cell types. Antibodies or fragments thereof for use as one or more binding agents of target cell types can include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, chimeric antibodies, non-human antibodies, fully human antibodies, among others. Single chain or multiple chain antigen-recognition sites can be used. Multiple chain antigen-recognition sites can be fused or unfused. Antibodies or fragments thereof can be generated using standard methods. See, e.g., Harlow & Lane, *Antibodies: A Laboratory Manual*, Cold Spring Harbor Laboratory Press; $1^{st}$ edition 1988, which is incorporated herein by reference. Alternatively, an antibody or fragment thereof directed against one or more inflammatory mediators can be generated, for example, using phage display technology. See, e.g., Kupper, et al. *BMC Biotechnology* 5:4, 2005, which is incorporated herein by reference. An antibody, a fragment thereof, or an artificial antibody, e.g., Affibody® artificial antibodies (Affibody AB, Bromma, Sweden) can be prepared using in silico design. See, e.g., Knappik et al., *J. Mol. Biol.* 296: 57-86, 2000, which is incorporated herein by reference. In an aspect, antibodies directed against one or more inflammatory mediators may be available from a commercial source (from, e.g., Novus Biological, Littleton, Colo.; Sigma-Aldrich, St. Louis, Mo.; United States Biological, Swampscott, Mass.).

The one or more reactive components including the one or more binding agents can include one or more aptamers that bind one or more target cell types. The aptamer can be an oligonucleotide RNA- or DNA-based aptamer. Aptamers are artificial oligonucleotides (DNA or RNA) which can bind to a wide variety of entities (e.g., metal ions, small organic molecules, proteins, and cells) with high selectivity, specificity, and affinity. Aptamers can be isolated from a large library of $10^{14}$ to $10^{15}$ random oligonucleotide sequences using an iterative in vitro selection procedure often termed "systematic evolution of ligands by exponential enrichment" (SELEX). See, e.g., Cao, et al., *Current Proteomics* 2:31-40, 2005; Proske, et al., *Appl. Microbiol. Biotechnol.* 69:367-374, 2005; Jayasena *Clin. Chem.* 45:1628-1650, 1999, each of which is incorporated herein by reference. In general, SELEX can be used to generate aptamers against a variety of cell types including but not limited to cancer cells, bacteria, and parasites. See, e.g., Shangguan, et al., *Proc. Natl. Acad. Sci. USA.* 103:11838-11843; Chen, et al., *Biochem. Biophys. Res. Commun.* 357:743-748, 2007; Ulrich, et al., *J. Biol. Chem.* 277: 20756-20762, 2002, each of which is incorporated herein by reference.

In an aspect, the one or more reactive components including the one or more binding agents can include one or more aptamers that are peptide based aptamers. Peptide aptamers are artificial proteins in which inserted peptides are expressed as part of the primary sequence of a structurally stable protein. See, e.g., Crawford, et al., *Brief Funct. Genomic Proteomic* 2:72-79, 2003, which is incorporated herein by reference. Peptide aptamers can be generated by screening a target cell against yeast two-hybrid libraries, yeast expression libraries, bacterial expression libraries and/or retroviral libraries. Peptide aptamers can have binding affinities comparable to antibodies.

The one or more reactive components including the one or more binding agents include one or more peptide receptor ligands that bind receptors associated with one or more target cell types. Examples of peptide receptor ligands include, but are not limited to, neuropeptides (e.g., enkephalins, neuropeptide Y, somatostatin, corticotropin-releasing hormone, gonadotropin-releasing hormone, adrenocorticotropic hormone, melanocyte-stimulating hormones, bradykinins, tachykinins, cholecystokinin, vasoactive intestinal peptide (VIP), substance P, neurotensin, vasopressin, and calcitonin); cytokines (e.g., interleukins (e.g., IL-1 through IL-35), erythropoietin, thrombopoietin, interferon (IFN), granulocyte monocyte colony-stimulating factor (GM-CSF), tumor necrosis factor (TNF), and others); chemokines, (e.g., RANTES, TARC, MIP-1, MCP, and others); growth factors (e.g., platelet derived growth factor (PDGF), transforming growth factor beta (TGFβ), nerve growth factor (NGF), epidermal growth factor (EGF), insulin-like growth factor (IGF), basic fibroblast growth factor (bFGF)); other peptide hormones including atrial natriuretic factor, insulin, glucagon, angiotensin, prolactin, oxyocin, and others.

In an aspect, the one or more reactive components including the one or more binding agents can include one or more novel peptides. Novel peptides that bind selective targets can be generated using phage display methodologies. See, e.g., Spear, et al., *Cancer Gene Ther.* 8:506-511, 2001, which is incorporated herein by reference. In this aspect, the phage express novel peptides on the surface as fusion proteins in association with a phage major or minor coat protein and can be screened for binding interaction with one or more target cell types.

The one or more reactive components including the one or more binding agents can include one or more artificial binding substrates for one or more target cell types formed by the process of molecular imprinting. In the process of molecular imprinting, a template is combined with functional monomers which upon cross-linking form a polymer matrix that surrounds the template. See Alexander, et al., *J. Mol. Recognit.* 19:106-180, 2006, which is incorporated herein by reference. Removal of the template leaves a stable cavity in the polymer matrix that is complementary in size and shape to the template. In an aspect, functional monomers of acrylamide and ethylene glycol dimethacrylate can be mixed with a target cell and/or an isolated cell surface component of a target cell in the presence of a photoinitiator and ultraviolet irradiation used to cross-link the monomers. The resulting polymer can be crushed or ground into smaller pieces and washed to remove the target cell and/or the isolated cell surface component of the target cell, leaving a particulate matrix material capable of binding one or more target cell types. Examples of other functional monomers, cross-linkers and initiators can be used to generate an artificial binding substrate are provided. See, e.g., U.S. Pat. No. 7,319,038; Alexander, et al., *J. Mol. Recognit.* 19:106-180, 2006, each of which is incorporated herein by reference. In an aspect, hydrogels can be used for molecular imprinting. See, e.g., Byrne et al., "Molecular imprinting within hydrogels", *Advanced Drug Delivery Reviews*, 54: 149-161, 2002, which is incorporated herein by reference. Other examples of synthetic binders are provided. See, e.g., U.S. Pat. Nos. 6,255,461; 5,804,563; 6,797,522; 6,670,427; and 5,831,012; and U.S. Patent Application 20040018508; and Ye and Haupt, *Anal Bioanal Chem.* 378: 1887-1897, 2004; Peppas and Huang, *Pharm Res.* 19: 578-587 2002, each of which is incorporated herein by reference.

Reactive Components Can Include Cell-Disrupting Agents that Modulate the Physiological Effect of One or More Target Cell Types. The device including one or more reactive components configured to modulate a physiological effect of the one or more target cell types can include one or more cell-disrupting agents. Examples of cell-disrupting agents include, but are not limited to, alcohols and other organic solvents such as methanol, ethanol, isopropanol, and acetone; cross-linking aldehydes such as formaldehyde and gluteraldehyde; oxidizing agents such as sodium hypochlorite, calcium hypochlorite, chloramine, chlorine dioxide, hydrogen peroxide, iodine, ozone, acidic electrolyzed water, peracetic acid, performic acid, potassium permanganate, potassium peroxymonosulfate; acids such as acetic acid, trichloroacetic acid (TCA), sulfosalicyclic acid, picric acid; phenolics such as phenol, O-phenylphenol, chloroxylenol, hexachlorophene, thymol; chaotropic agents such as urea, guanidinium chloride, and lithium perchlorate; and disulfide bond reducers such as 2-mercaptoethanol, dithiothreitol; and quaternary ammonium compounds. For example, organic solvents such as methanol, ethanol or acetone can disrupt a cell by solubilizing the lipids in the plasma membrane and allowing the soluble contents of the cell to be released. In an aspect, the one or more cell-disrupting agents are incorporated into or released within one or more treatment regions of the device. In an aspect, the one or more cell-disrupting agents are released by the device as diffusible agents into the blood fluid or lymph fluid.

The one or more cell-disrupting agents configured to modulate a physiological effect of the one or more target cell types can act by breaking peptide bonds within the primary amino acid sequence of proteins and peptides associated with one or more target cell types. In an aspect, the device including one or more cell-disrupting agents can include one or more proteases. Examples of proteases include, but are not limited to, serine proteases, e.g., as trypsin, chymotrypsin, elastase, dipeptidyl peptidase IV, and subtilisin; cysteine proteases, e.g., papain, cathepsins, caspases, calpains; aspartic acid proteases, e.g., pepsin, renin, and HIV-proteases; metalloproteases, e.g. carboxypeptidases, aminopeptidases, and matrix metalloproteases, e.g. MMP1 through MMP28. In one aspect, the one or more proteases are free in solution. In an aspect, the one or more proteases are bound to a substrate. For example, the protease trypsin can be bound to glass beads. See, e.g., Lee, et al., *J. Dairy Sci.,* 58: 473-476, 1974, which is incorporated herein by reference. Alternatively, trypsin and/or other proteases can be bound to an agarose matrix. Sources of immobilized proteases including trypsin and pepsin are available from commercial sources (Pierce Chemicals, Rockford, Ill.; Applied Biosystems, Foster City, Calif.).

The device including one or more reactive components that include one or more cell-disrupting agents can include one or more reactive oxygen species. Examples of reactive oxygen species include, but are not limited to, singlet molecular oxygen, superoxide ion, hydrogen peroxide, hypochlorite ion, hydroxyl radical. Reactive oxygen species can react directly with proteins associated with the one or more target cell types, targeting peptide bonds or amino acid side chains, for example, reacting with the one or more target cell types bound by an affinity binding component to a surface of the treatment region. See, e.g., Davies, *Biochem. Biophys. Res. Commun.* 305:761-770, 2003, which is incorporated herein by reference. In an aspect, the device including one or more cell-disruptive agents can include reactive oxygen species that are singlet oxygen species. Singlet oxygen can cause damage to both the side-chains and backbone of amino acids, peptides, and proteins. See, e.g., Davies, *Biochem. Biophys. Res. Commun.* 305:761-770, 2003, which is incorporated herein by reference. Singlet oxygen species can react with tryptophan, tyrosine, histidine, methionine and/or cysteine and cystine residues within a polypeptide and can cause increased susceptibility to proteolytic enzymes, an increased extent/susceptibility to unfolding, changes in conformation, an increase in hydrophobicity, and changes in binding of co-factor and metal ions. In particular, the interaction of tyrosine with singlet oxygen species can lead to fragmentation or cleavage of the polypeptide. See, e.g., Davies, *Biochem. Biophys. Res. Commun.* 305:761-770, 2003, which is incorporated herein by reference.

The device including one or more reactive components that include one or more cell-disrupting agents can include one or more singlet oxygen species generated by a photo sensitizer, a chemical which upon exposure to a given wavelength of light emits singlet oxygen species. Examples of photosensitizers include, but are not limited to, porphyrin derivatives such as Photofin, which is excited by red light at 630 nm; chlorins and bacteriochlorins such as bonellin (maximum absorbance 625 nm), mono-L-aspartyl chlorine e6 (max abs 654), m-tetrahydroxyphenyl chlorine (mTHPC, max absorbance 652 nm), and tin etiopurpurin (SnET2, maximum absorbance 660 nm); benzoporphyrin derivatives such as veteroporfin (also labeled BPD-MA, maximum absorbance 690 nm), 5-aminolaevulinic acid (ALA, porphoryin precursor to PpIX (maximum absorbance 635 nm)); texaphyrins such as lutetium texaphyrin (Lu-Tex, maximum absorbance 732), Phthalocyanines and naphthalocyanines (maximum absorbance 670-780 nm); and cationic photosensitizers such as rhodamine 123 and methylene blue. See, e.g., Prasad (2003) *Introduction to Biophotonics*, John Wiley & Sons, Inc. Hoboken, N.J. Tunable quantum dots (QDs), especially those absorbing in the wavelength range of 600 to 800 nm, also emit singlet oxygen species in response to light provided by the device. The tunable quantum dots can be useful as photosensitizers. See, e.g., Samia, et al. (2006) *Photochem. Photobiol.* 82:617-625, which is incorporated herein by reference.

Reactive Components Can Include One or more Reactive Components Including One or More of Cytotoxic, Cytostatic, Apoptotic, and/or Chemotherapeutic Agents That Modulate the Physiological Effect One or More Target Cell Types. The device including one or more reactive component can include one or more of a cytotoxic, a cytostatic, a programmed cell death-inducing, and/or a chemotherapeutic agent. Reactive components that are cytotoxic, cytostatic, apoptotic, and/or chemotherapeutic agents are contemplated that either directly or indirectly inactivate or kill one or more target cell types. Examples of cytotoxic, cytostatic, apoptotic, and/or chemotherapeutic agents include, but are not limited to, vinca alkaloids (e.g., vinblastine, vincristine, vinflunine, vindesine, vinorelbine); taxanes (e.g., docetaxel, larotaxel, ortataxel, paclitaxel, tesetaxel); epothilones (e.g., ixabepilone); dihydrofolate reductase inhiitors (e.g., aminopterin, methotrexate, pemetrexed); thymidylate synthase inhibitors (e.g., raltitrexed); adenosine deaminase inhibitor (e.g., pentostatin); halogenated/ribonucleotide reductase inhibitors (e.g., cladribine, clofarabine, fludarabine); thiopurine (e.g., thioguanine, mercaptopurine); thymidylate synthase inhibitors (e.g., fluorouracil, capecitabine, tegafur, carmofur, floxuridine); DNA polymerase inhibitors (e.g., cytarabine); ribonucleotide reductase inhibitor (e.g., gemcitabine, hydroxyurea); hypomethylating agent (e.g., azacitidine, decitabine); camptotheca (e.g., camptothecin, topotecan, irinotecan, rubitecan, belotecan); podophyllum (e.g., etoposie, teniposide); anthracyclines (e.g., aclarubicin, daunorubicin, doxorubicin, epirubicin, idarubicin, amrubicin, pirarubicin, valrubicin, zorubicin); anthracenediones (e.g., mitoxantrone, pixantrone); nitrogen mustards (e.g., mechlorethamine, cyclophosphamide, chlorambucil, bendamustine, uramustine, estramustine); nitrosureas (e.g., carmustine, lomustine, fotemustine, nimustine, ranimustine, streptozocin); aziridines (e.g., carboquone, thioTEPA, triziquone, triethylenemelamine); platinum (e.g., carboplatin, cisplatin, nedaplatin, oxaliplatin, triplatin, tetranitrate, satraplatin); hydrazines (e.g., procarbazine); triazenes (e.g., dacarbazine, temozolomide, altretamine, mitobronitol); streptomyces (actinomycin, bleomycin, mitomycin, plicamycin); aminolevulinic acid/methyl aminolevulinate; efaproxiral; porphyrin derivatives (porfimer sodium, talaporfin, temoporfin, verteporfin); farnesyltransferase inhibitors, cyclin-dependent kinase inhibitors, proteasome inhibitors, phosphodiesterase inhibitors, IMP dehydrogenase inhibitors, lipooxygenase inhibitors, PARP inhibitors, endothelin receptor antagonists (e.g., atrasentan); retinoid X receptor (e.g., bexarotine); sex steroid (e.g., testolactone); amsacrine, trabectedin, alitretinoin, tretinoin, arsenic trioxide, celecoxib, demecolcine, elesclomol, elsamitrucin, etoglucid, lonidamine, lucanthone, mitoguazone, mitotane, oblimersen, temsirolimus, vorinostat. The cytotoxic agent can further be a biological agent, e.g., a peptide, a protein, an enzyme, a receptor and/or an antibody. Examples of biological agents currently used to treat cancer include, but are not limited to, cytokines such as interferon-α, interferon-γ, and interleukin-2, an enzyme such as asparaginase, and monoclonal antibodies such as alemtuzumab, bevacizumab, cetuximab, gemtuzumab, rituximab, and trastuzumab.

The device including one or more reactive components that are cytotoxic, cytostatic, apoptotic, and/or chemotherapeutic agents can include one or more of an antibacterial drug. Examples of antibacterial drugs include, but are not limited to, beta-lactam compounds (e.g., penicillin, methicillin, nafcillin, oxacillin, cloxacillin, dicloxacilin, ampicillin, ticarcillin, amoxicillin, carbenicillin, and piperacillin); cephalosporins and cephamycins (e.g., cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxine, ceftriaxone, cefixime, cefpodoxime, proxetil, cefdinir, cefditoren, pivoxil, ceftibuten, moxalactam, and cefepime); other beta-lactam drugs (e.g., aztreonam, clavulanic acid, sulbactam, tazobactam, ertapenem, imipenem, and meropenem); other cell wall membrane active agents (e.g., vancomycin, teicoplanin, daptomycin, fosfomycin, bacitracin, and cycloserine); tetracyclines (e.g., tetracycline, chlortetracycline, oxytetracycline, demeclocycline, methacycline, doxycycline, minocycline, and tigecycline); macrolides (e.g., erythromycin, clarithromycin, azithromycin, and telithromycin); aminoglycosides (e.g., streptomycin, neomycin, kanamycin, amikacin, gentamicin, tobramycin, sisomicin, and netilmicin); sulfonamides (e.g., sulfacytine, sulfisoxazole, silfamethizole, sulfadiazine, sulfamethoxazole, sulfapyridine, and sulfadoxine); fluoroquinolones (e.g., ciprofloxacin, gatifloxacin, gemifloxacin, levofloxacin, lomefloxacin, moxifloxacin, norfloxacin, and ofloxacin); antimycobacteria drugs (e.g., isoniazid, rifampin, rifabutin, rifapentine, pyrazinamide, ethambutol, ethionamide, capreomycin, clofazimine, and dapsone); and miscellaneous antimicrobials (e.g., colistimethate sodium, methenamine hippurate, methenamine mandelate, metronidazole, mupirocin, nitrofurantoin, polymyxin B, clindamycin, choramphenicol, quinupristin-dalfopristin, linezolid, spectrinomycin, trimethoprim, pyrimethamine, and trimethoprim-sulfamethoxazole).

The device including one or more reactive components that include cytotoxic, cytostatic, apoptotic, and/or chemotherapeutic agents can include one or more of an antifungal agent. Examples of antifungal agents include, but are not limited to, anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

The device including one or more reactive components that are cytotoxic, cytostatic, apoptotic, and/or chemotherapeutic agents can include one or more of an anti-parasite agent. Examples of anti-parasite agents include, but are not limited to, antimalaria drugs (e.g., chloroquine, amodiaquine, quinine, quinidine, mefloquine, primaquine, sulfadoxine-pyrimethamine, atovaquone-proguanil, chlorproguanil-dapsone, proguanil, doxycycline, halofantrine, lumefantrine, and artemisinins); treatments for amebiasis (e.g., metronidazole, iodoquinol, paromomycin, diloxanide furoate, pentamidine, sodium stibogluconate, emetine, and dehydroemetine); and other anti-parasite agents (e.g., pentamidine, nitazoxanide, suramin, melarsoprol, eflornithine, nifurtimox, clindamycin, albendazole, and tinidazole).

The device including one or more reactive components that are cytotoxic, cytostatic, apoptotic, and/or chemotherapeutic agents can include one or more of an antiviral agent. Examples of antiviral agents include, but are not limited to, nucleoside analogs used to treat herpes simplex virus (HSV) and varicella-zoster virus (VZV) (e.g., valacyclovir, famciclovir, penciclovir, and trifluridine); nucleoside analogs used to treat cytomegalovirus (CMV) (e.g., ganciclovir, valganciclovir, and cidofovir); nucleoside and nonnucleoside reverse transcriptase inhibitors used to treat HIV (e.g., abacavir, didanosine, emtricitabine, lamivudine, stavudine, tenofovir, zalcitabine, zidovudine, delavirdine, efavirenz, and nevirapine); protease inhibitors used to treat HIV (e.g., atazanavir, darunavir, fosamprenavir, indinavir, lopinavir, nelfmavir, ritonavir, saquinavir, and tipranavir); and drugs used to treat hepatitis (e.g., interferon alfa, adefovir dipivoxil, entecavir, and ribavirin).

The device can include one or more reservoirs responsive to the controller, wherein the one or more reservoirs is configured to provide the one or more reactive components, e.g., one or more cytotoxic, cytostatic, apoptotic, and/or chemotherapeutic agents, and to function in, or proximal to, the one or more blood vessel or lymph vessel of the vertebrate subject. The device including one or more reservoirs can be configured to controllably release one or more cytotoxic, cytostatic, apoptotic, and/or chemotherapeutic agents into the treatment region and/or into the blood fluid or lymph fluid of the vertebrate subject. Each reservoir can contain one or more cytotoxic, cytostatic, apoptotic, or chemotherapeutic agents. Release of a cytotoxic, cytostatic, apoptotic, and/or chemotherapeutic agents from a reservoir into one or more treatment regions and/or into the blood fluid or lymph fluid is controlled by the controller component of the device. In an aspect, the one or more cytotoxic, cytostatic, apoptotic, and/or chemotherapeutic agents can be housed in multiple reservoirs associated with the device. For example, the device can include one or more microchips each with multiple reservoirs controllably sealed to enable controlled release of one or more one or more cytotoxic, cytostatic, apoptotic, and/or chemotherapeutic agents. See, e.g., U.S. Pat. No. 7,413,846; Maloney & Santini, Proceedings 26$^{th}$ Annual International Conference IEEE EMBS, San Francisco, Calif., USA, Sep. 1-5, 2004, each of which is incorporated herein by reference.

Reactive components that are cytotoxic, cytostatic, apoptotic, and/or chemotherapeutic agents can be any of a number of chemical types including but not limited to a small molecule, an aptamer, or an inhibitory RNA, DNA, or other nucleic acid. In an aspect, the one or more cytotoxic, cytostatic, apoptotic, and/or chemotherapeutic agents can be a recombinant protein or peptide. The recombinant protein or peptide can be generated exogenously and incorporated into one or more treatment regions of the device. In an aspect, the recombinant protein or peptide can be generated by one or more cells incorporated into the device. The one or more cells can be genetically modified to synthesize and secrete the one or more cytotoxic, cytostatic, and/or apoptotic agents. Cells that can be used for this purpose include, but are not limited to, mammalian cells, enucleated cells (e.g., erythrocytes), plants cells, bacteria, or yeast. DNA sequences corresponding to one or more modulators are cloned into an appropriate cell type using standard procedures with appropriate expression vectors and transfection protocols. The genetically modified cells are encapsulated in one or more compartments of the device and secrete the one or more cytotoxic, cytostatic, apoptotic, and/or chemotherapeutic agents into the blood fluid or lymph fluid of the vertebrate subject. The genetically modified cells are kept separate from the circulation of a subject using a size-limiting biocompatible mesh or membrane filter, for example, that allows passage of the cytotoxic, cytostatic, apoptotic, and/or chemotherapeutic agent, but not the larger cells.

In an aspect, the one or more cytotoxic, cytostatic, apoptotic, and/or chemotherapeutic agents are released from synthetic vesicles or particles. Examples include any of a number of drug delivery vehicles including, but not limited to, phospholipid vesicles (liposomes), nanoparticles, or hydrogels. The release of the one or more cytotoxic, cytostatic, apoptotic, and/or chemotherapeutic agents can be triggered by binding of a specific target to the synthetic vesicle or particle. For example, one or more DNA aptamers can be incorporated into hydrogel and designed to bind one or more specific targets and release the contents of the hydrogel in response to the controller which releases the hydrogel into the blood fluid or lymph fluid of the subject.

Reactive Components Including One or More Energy Sources Can Modulate the Physiological Effect of One or More Target Cell Types. The device can include one or more reactive components that include one or more energy sources configured modulate a physiological effect of one or more target cell types. The one or more energy sources can be directed to blood fluid or lymph fluid within the treatment region or can be directed outside the device to the blood fluid or lymph fluid. The one or more energy sources provide energy types including, but not limited to, electromagnetic radiation, e.g., ultraviolet, infrared, optical, microwave, or millimeter wave; acoustic energy, e.g., ultrasonic acoustic energy; heat; electrical; atmospheric pressure glow discharge; electron beam radiation; or gamma radiation. In an aspect, the energy source itself can modulate a physiological effect of the one or more target cell types. Alternatively, heat generated by the energy source can modulate a physiological effect of one or more target cell types. The application of one or more energy sources to the blood fluid or lymph fluid of the vertebrate subject in the form of electromagnetic, acoustic, and/or electronic energy can induce cellular disruption of a target cell leading to inactivation, programmed cell death or death of the target cell.

The device including the one or more energy sources can provide a set of differing energy inputs specifically directed modulate a physiological effect of the one or more target cell types. The set of differing energy inputs selectively resonates a plurality of resonant structures in the one or more target cell types See, e.g., U.S. Patent Application 2007/0021927 A1, which is incorporated herein by reference. The differing energy inputs are selected to resonate one or more resonant structures among the group of proximate atoms comprising cellular components of the one or more target cell types. Application of a series of differing energy inputs can have a physical effect, such as transferring substantially more energy to a group of proximate atoms relative to other atoms in the surrounding medium, breaking a predetermined bond between two members of the group of proximate atoms, or changing a kinetic parameter of a reaction involving a member of the group of proximate atoms. The one or more resonant structures can be resonated simultaneously, sequentially, and/or in a temporally overlapping fashion. The series of differing energy inputs can be applied simultaneously, sequentially, and/or in a temporally overlapping fashion.

The set of differing energy inputs can be electromagnetic beams, each of which can have one or more characteristics including, but not limited to, a selected set of frequencies, a selected set of phases, a selected set of amplitudes, a selected temporal profile, a selected set of polarizations, or a selected direction. The temporal profile of the set of differing energy inputs can be characterized by a selected beam duration, and/or by a selected change in frequency, modulation frequency, phase, amplitude, polarization, or direction during a selected time interval. At least one electromagnetic beam can be polarized, amplitude modulated, or frequency modulated, and it can be, for example, an infrared beam. A plurality of electromagnetic beams can differ in frequency, modulation frequency, phase, amplitude, polarization, or direction, and/or can intersect at a target location. The method can include scanning at least one electromagnetic beam.

In an aspect, the device can include one or more energy sources that include an electric field, a magnetic field, an electromagnetic field, a mechanical stress, a mechanical strain, a lowered or elevated temperature, a lowered or elevated pressure, a phase change, an adsorbing surface, a catalyst, an energy input, or a combination of any of these. The energy field can result in cellular disruption of target cell types. Mechanical stress, mechanical strain, lowered or elevated pressure, phase change, or adsorbing surface can provide energy to result in cellular disruption of target cell types.

The device including one or more energy sources can emit electrical energy in a focused area within the treatment region to inactivate one or more target cell types. For example, cancer cells in suspension can be at least partially ablated using electrical pulses sufficient to induce irreversible electroporation of the cells. See, e.g., Miller et al. *Technol. Cancer Res. Treat.* 4:699-705, 2005, which is incorporated herein by reference. In an aspect, at least partial inactivation of one or more targets cell can be achieved by exposure to 10-30, 0.3 millisecond pulses at 500 to 2500 V/cm.

The device including one or more energy sources can emit electromagnetic energy sufficient modulate a physiological effect of one or more target cell types. The electromagnetic energy can range over a spectrum of frequencies from gamma ray, x-ray, ultraviolet, visible, near infrared, infrared, microwave, to radiowaves.

The device including one or more energy sources can emit ultraviolet radiation modulate a physiological effect of one or more target cell types. A number of pathogens are inactivated or killed by ultraviolet germicidal irradiation. Ultraviolet light ranges from UVA (400-315 nm; long wave or 'blacklight'), UVB (315-280 nm, medium wave), and UVC (<280 nm, short wave or 'germicidal'). The bacterium Escherichia coli is partially or completely inactivated by exposure to a UV electromagnetic energy source at wavelengths of 100-280 nm. *Escherichia coli* as well as *Salmonella enteritidis* is also inactivated using pulsed broad-spectrum electromagnetic energy with high UV content from, for example, a Xenon lamp. In this instance, targeted bacteria are subjected to 100-

1000 pulses of broad-spectrum light with each pulse lasting, for example, 85 ns and having, for example, a power output of 10 MW. See, e.g., Anderson et al. *IEEE Transactions on Plasma Science* 28:83-88, 2000; Hancock et al. *IEEE Transactions on Plasma Science* 32:2026-2031, 2004, each of which is incorporated herein by reference. Viruses and fungi (e.g., *Aspergillus flavus* and *Aspergillus fumigatus*) are also inactivated by ultraviolet irradiation. See, e.g., Tseng & Li, J. *Occup. Envirn. Hyg.* 4:400-405, 2007; Green et al. *Can. J. Microbiol.* 50:221-224, 2004, each of which is incorporated herein by reference.

The device including one or more energy sources can emit visible light modulate a physiological effect of one or more target cell types. *Staphylococcus aureus* and *Pseudomonas aeruginosa* can be inactivated using a wavelength of 405 nm at doses ranging from 1-20 J/cm$^2$. See, e.g., Guffey et al. *Photomed. Laser Surg.* 24:680-683, 2006, which is incorporated herein by reference. *Pseudomonas aeruginosa* as well as *Escherichia coli* are partially inactivated using a wavelength of 630 nm at 1-20 J/cm$^2$. See, e.g., Nussbaum et al. *J. Clin. Laser Med. Surg.* 20:325-333, 2002, which is incorporated herein by reference. In an aspect, a pathogen such as *Escherichia coli* can be at least partially inactivated or killed using a 810 nm diode laser with doses ranging from 130-260 J/cm$^2$. See, e.g., Jawhara et al. *Lasers Med Sci.* 21:153-159, 2006, which is incorporated herein by reference. In an aspect, visible or near infrared energy (e.g., 465 nm, 600 nm, and 950 nm) can be used to modulate a physiological effect of iron dependent pathogens by altering the function of heme iron prophyrins. See, e.g., U.S. Pat. No. 6,030,653, which is incorporated herein by reference. In an aspect, viruses can be at least partially inactivated using a very low power laser emitting 80 femtosecond pulses at a wavelength of 425 nm and frequency of 80 MHz. See, e.g., Tsen et al. *Virol. J.* 4:50, 2007, which is incorporated herein by reference.

In an aspect, the reactive component can include visible light energy combined with one or more reactive component that include a photosensitive agent configured to modulate a physiological effect of one or more target cell types. See, e.g., Maisch *Lasers Med. Sci.* 22:83-91, 2007; Joni et al. *Lasers Surg. Med.* 38:468-481, 2006, each of which is incorporated herein by reference. The visible light energy combined with the one or more photosensitive agents can be focused to a site of bacterial infection in the vertebrate subject, or can be focused onto the target cell or target component within the target region in the vertebrate subject. For example, *Staphylococcus aureus* and *Pseudomonas aeruginosa* are inactivated using either a 0.95-mW helium-neon laser (632 nm) or a 5-mW indium-gallium-aluminum-phosphate laser (670 nm) with exposure doses ranging from 0.1 to 10.0 J/cm$^2$ in combination with the bacterial sensitizing agent, toluidine blue O. See, e.g., DeSimone et al. *Phys. Ther.* 79:839-846, 1999, which is incorporated herein by reference. Similarly, bacterial inactivation by a laser diode or light-emitting diode at 630 nm to 665 nm is enhanced in combination with methylene blue. See, e.g., Chan et al. *Lasers Surg. Med.* 18:51-55, 2003, which is incorporated herein by reference. A fluorescing dye, e.g., indocyanine green (ICG) can be used in combination with a diode laser emitting at 808 nm to inactive a pathogen or pathogens. See, e.g., Bartels et al. *SPIE* 2395: 602-606, 1995, which is incorporated herein by reference. In an aspect, a target cell, e.g., bacteria, can be inactivated using a polycationic photosensitizer in combination with irradiation with a diode laser at 665 nm at doses ranging up to a total fluence of 160 J/cm$^2$, e.g., in four 40 J/cm$^2$ aliquots, with imaging taking place after each aliquot of light. See, e.g., Hamblin et al. *Photochem. Photobiol.* 75:51-57, 2002, which is incorporated herein by reference. In an aspect, a target cell, e.g., *Staphylococcus aureus* can be at least partially inactivated using energy from an argon-ion pumped dye laser (wavelength of 630 nm with total light dose up to 180 J/cm$^2$, wherein the total light dose can be provided in one or more lower light energy aliquots) in combination with 5-aminolevulinic acid or porphyrin sodium. Effective photokilling of a target cell, e.g., *Staphylococcus aureus* or *Escherichia coli*, by endogenous porphyrins or exogenous porphyrins can be achieved by application of light at 400-450 nm at approximately 50 J/cm$^2$. With 600-700 nm light, a 10-fold higher light dose can provide a similar result for *S. aureus* killing. With dye laser light at 632.8 nm, 50 J/cm$^2$ can provide 3 orders of decrease in the viability of *S. aureus*. With white light, 75 J/cm$^2$ can provide 2-3 orders of decrease of *S. aureus* viability. See, e.g., Karrer et al. *Lasers Med. Sci.* 14:54-61, 1999; Nitzan et al. *Lasers Med. Sci.* 14:269-277, 1999, each of which is incorporated herein by reference.

The device including the one or more energy sources can generate heat to modulate a physiological effect of the one or more target cell types. In an aspect, the physilogical effect of one or more target cell types can be modulated by laser-induced thermal energy. Lasers are commonly used to treat cancers including but not limited to basal cell carcinoma and the very early stages of cervical, penile, vaginal, vulvar, and non-small cell lung cancer. See, e.g., National Cancer Institute *Laser in Cancer Treatment FactSheet*, 2004, which is incorporated herein by reference. In an aspect, the device can include one or more laser-type component capable of emitting electromagnetic energy sufficient to modulate a physiological effect of circulating tumor cells. Examples include, but are not limited to, a carbon dioxide ($CO_2$) laser (10,600 nm, 0.1-0.2 mm penetration depth), a Yttrium-Aluminium-Garnet (YAG) laser with Neodymium (Nd, 1064 nm or 1320 nm, 3-4 mm penetration depth), Erbium (Eb, 2940 nm, with <0.1 mm penetration depth), or Holmium (Ho, 2070 nm), diode laser (600-1600 nm), argon laser (488 nm and 514 nm, 1-1.5 mm penetration depth), or an excimer laser (180-350 nm, cell/tissue disintegration). As an example, melanoma and cervical cancer cells can be ablated with a $CO_2$ laser using a power output ranging from 40 W to 80 W. See, e.g., Gibson, et al. *Br. J. Surg.* 91:893-895, 2004; Bekassy et al. *Lasers. Surg. Med.* 20:461-466, 1997; Norberto et al. *Surg. Endosc.* 19:1045-1048, 2005; Hansen et al. *Minim. Invasive Ther. Allied Technol.* 15:4-8, 2006, each of which is incorporated herein by reference. Laser-induced thermal energy generated by a $CO_2$ or Nd:YAG laser can also be used to at least partially inactivate a pathogen. See, e.g. Bartels et al. *SPIE* 2395:602-606, 1995; Yeo et al. *Pure Appl. Opt.* 7:643-655, 1998; U.S. Pat. No. 6,030,653; Gronqvist et al. *Lasers Surg. Med.* 27:336-340, 2000, each of which is incorporated herein by reference.

The device including the one or more energy sources can emit electromagnetic energy in the form of x-rays to modulate a physiological effect of one or more target cell types. In an aspect, the device can contain a miniature X-ray emitter, such as that described in U. S. Patent Application 2004/0218724 A1. In an aspect, the device can contain radioisotopes, e.g., cobalt 60, cesium 137, or europium 152, that emit strong gamma rays and can be used to ablate cancerous cells. Optionally, the device can contain other intrinsically radioactive isotope such as those that might be used for brachytherapy, including, for example, iodine 125, iodine 131, strontium 89, phosphorous, palladium, or phosphate. In an aspect, the device can include an energy source that is an electron beam-driven x-ray source. For example, breast cancer cells can be ablated using a miniature electron beam-driven x-ray source at doses of 5 to 20 Gy. See, e.g., Ross et al. *Breast Cancer Res.* 7:110-112, 2005, which is incorporated herein by reference. A nanoscale electron beam generator can be devised from a network array structure of carbon nanotubes. See, e.g., U.S. Pat. No. 7,355,334, which is incorporated herein by reference.

The device including the one or more energy sources can generate electromagnetic energy in the form microwave or radiofrequency waves to modulate a physiological effect of one or more target cell types. The microwave range can include ultra-high frequency (UHF) (0.3-3 GHz), super high frequency (SHF) (3-30 GHz), and extremely high frequency (EHF) (30-300 GHz) signals. Microwave radiation at a frequency of 29.8 GHz (Ka-band), for example, can be used to selectively kill bacteria with minimal damage to healthy human cells (Ardnt et al. Microwave radiation—Therapeutic application for cure of subcutaneous bacterial infections. Space Life Sciences, NASA Research and Technology Development. Biennial Research and Technology Report).

The device including the one or more energy sources can use focused ultrasound to generate heat to modulate a physiological effect of one or more target cell types. Ultrasound causes tissue damage through conversion of mechanical energy into heat and through cavitation. Above a threshold of 56 degrees centigrade, for example, rapid thermal toxicity is achieved and cells are irreversibly inactivated or killed. High-intensity focused ultrasound (HIFU) uses short exposures of focused ultrasound that rapidly increases cellular temperature above 80° C. and is used for ablation, for example, of hepatocellular carcinoma, prostate carcinoma, bladder and kidney cancers. See, e.g., Kennedy et al. Br. J. Radiology 76:590-599, 2003, which is incorporated herein by reference.

Optionally, the device can emit a laser-generated stress wave sufficient to disrupt a biological target. For example, stress waves sufficient to disrupt cell membranes can be generated with an ArF (193 nm) or a KrF (248 nm) eximer laser. Peripheral blood mononuclear cells and red blood cells are damaged using, for example, 5 pulses of pressure ranging from 700 to 1000 bar. See, e.g., Lee et al. IEEE Journal of Selected Topics in Quantum Electronics 5:997-1003, 1999, which is incorporated herein by reference.

Two or More Reactive Components Can Be Combined to Modulate the Physiological Effect of One or More Inflammatory Mediators. The device can include two or more reactive components that have been combined to modulate a physiological effect of one or more target cell types. For example, the two or more combined reactive components can be one or more binding agent combined with one or more of a cell-disrupting agent, a binding agent, an energy source, a cytotoxic agent, a cytostatic agent, a programmed cell death-inducing agent, a chemotherapeutic agent, an antibody-toxin agent, or a combination thereof. A binding agent, e.g., oligonucleotide aptamer, can be used to capture one or more target cell types in the treatment region of the device prior to treatment with a cell-disrupting agent, a binding agent, an energy source, a cytotoxic agent, a cytostatic agent, a programmed cell death-inducing agent, a chemotherapeutic agent, an antibody-toxin agent, or a combination thereof.

In an aspect, the device including the two or more reactive components can have the two or more reactive components incorporated into a single biomolecule. For example, the first reactive component can be a binding agent, e.g., an antibody, that can include a second reactive component that is a cellular toxin. In another example, the first reactive component can be an antibody that binds a tumor cell and the second reactive component can be a photosensitizer which is activated upon exposure to electromagnetic energy. See, e.g., Sere-brovskaya, et al., *Proc. Natl. Acad. Sci. USA.* 106:9221-9225, 2009, which is incorporated herein by reference. In another example, the first reactive component can be an antibody directed against a cancer or other cell type and the second reactive component can be one or more auristatins, which are inhibitors of tubulin polymerization. See, e.g., Ma, et al., *Clin. Cancer Res.* 12:2591-2596, 2006, which is incorporated herein by reference.

In an aspect, the device including the two or more reactive components can incorporate the two or more reactive components into a single biomolecule. The single biomolecule can include a first component that is a binding agent, e.g., an aptamer, and a second component that is a cell-disrupting agent, e.g., a protease. For example, one or more proteases can be conjugated or chemically linked to one or more oligonucleotide-based aptamers. The oligonucleotide-based aptamers can be designed to bind one or more inflammatory mediators. Upon binding to the oligonucleotide-based aptamers, the one or more inflammatory mediators are brought into proximity to the one or more proteases resulting in proteolytic degradation of the one or more inflammatory mediators. Examples of proteases have been provided herein and can be linked to oligonucleotide-based aptamers using any of a number of methods for conjugating a polypeptide to an oligonucleotide. In an aspect, a polypeptide protease can be conjugated to an oligonucleotide-based aptamer using a streptavidin-biotin bridge by introducing a biotinylated oligonucleotide into the aptamer sequence and linking it to a biotinylated protease through a streptavidin bridge. Alternatively, the polypeptide protease can be conjugated to the oligonucleotide-based aptamer using a thiol-maleimide linkage in which a carbon with an attached thiol group is placed on the aptamer and reacts with a maleimide group added to the C terminus of the protease. See, e.g., Nitin, et al., *Nucleic Acids Res.* 32:e58, 2004, which is incorporated herein by reference. A number of modified nucleotides are commercially available for use in synthesizing oligonucleotide aptamers with amines or other side chains for cross-linking (TriLink Biotechnologies, San Diego, Calif.; Sigma Aldrich, St. Louis, Mo.).

In an aspect, the two or more reactive components incorporated into a single biomolecule can include the first reactive component which is a binding agent linked to a second reactive component encapsulated in a target-responsive vesicle. For example, the second reactive component, e.g., a cell-disrupting agent, a binding agent, a cytotoxic agent, a cytostatic agent, a programmed cell death-inducing agent, a chemotherapeutic agent, an antibody-toxin agent, or a combination thereof, can be encapsulated in a tunable hydrogel. The binding of one or more target cell types to the first reactive component, e.g., binding agent, releases the second reactive component, e.g., cell-disrupting agent, binding agent, cytotoxic agent, cytostatic agent, apoptotic agent, chemotherapeutic agent, antibody-toxin agent, or a combination thereof from the hydrogel. A target-responsive hydrogel can be generated in which the contents of the hydrogel are selectively released in response to binding a specific target. In an aspect, the hydrogel incorporates one or more binding agents that are antibodies and the contents of the hydrogel are released in response to an antibody-antigen interaction. See, e.g., Miyata, et al., *PNAS* 103:1190-1193, 2006, which is incorporated herein by reference.

In an aspect, the target-responsive hydrogel can incorporate one or more binding agents that are oligonucleotide-based aptamers and release its contents in response to an aptamer-target interaction. See Yang, et al., *J. Am. Chem. Soc.* 130:6320-6321, 2008, which is incorporated herein by reference. In the latter case, two or more distinct aptamers configured to partially overlap during hybridization can be copolymerized into a polyacrylamide hydrogel. At least one of the two or more aptamers further binds to a specific target, e.g., a target cell. When the target cell binds to the aptamer, the number of nucleotide bases available for hybridization between the overlapping aptamers is reduced, causing them to separate. The separation allows the hydrogel to dissolute and to release its contents. A target responsive hydrogel can be generated that incorporates aptamers that specifically recognize one or more target cell types. The hydrogel itself can be loaded with one or more of a cell-disrupting agent, a binding agent, a cytotoxic agent, a cytostatic agent, a programmed cell death-inducing agent, a chemotherapeutic agent, an antibody-toxin agent, or a combination thereof that are configured to modulate a physiological effect of target cell types. The contents of the hydrogel are released upon binding of the one or more target cell types to the aptamers associated with the hydrogel. In an aspect, hydrogels can be used for molecular imprinting. See, e.g., Byrne et al., "Molecular imprinting within hydrogels," *Advanced Drug Delivery Reviews*, 54: 149-161, 2002, which is incorporated herein by reference.

Substrates for One or More Reactive Components. The device including the one or more reactive components can include cell-disrupting agents, a binding agents, cytotoxic agents, cytostatic agents, apoptotic agents, chemotherapeutic agents, antibody-toxin agents, or combinations thereof, can be free in solution within one or more treatment regions of the device. Lower concentration of the reactive components can be used to act locally at the site of the treatment region. Alternatively, the one or more reactive components can be immobilized on a solid substrate within the one or more treatment regions of the device. The solid substrate can be a matrix, e.g., a bead or filter, that is added to one or more treatment regions of the device. Examples of applicable solid substrates include, but are not limited to, beads, particles, membranes, semi-permeable membranes, capillary, or microarrays. The solid substrate can be comprised of an inorganic material, e.g., glass, alumina, silica, silicon, zirconia, graphite, magnetite, semiconductors, or combinations thereof. Alternatively, the solid substrate can be comprised of an organic material, e.g., polysaccharides including agarose, dextran, cellulose, chitosan, and polyacrylamide, polyacrylate, polystyrene, polyvinyl alcohol, or combinations thereof. Alternatively, the one or more specific binding agents or one or more reactive components can be associated with a solid substrate that are cells, e.g., mammalian cells, enucleated erythrocytes, bacteria, or viral particles or vesicles such as liposomes or other micellular vesicles.

In an aspect, the one or more reactive components, either free in solution or bound to a solid substrate, can be contained near the one or more treatment regions of the device either by size exclusion using a filter or mesh near the treatment region, containment within a hydrogel or polymer, or by physical attachment to the treatment region of the device. In a detailed aspect, one or more target cell types present in the blood can bind to the one or more reactive components as the blood passes through the device, and can be sequestered for inactivation. Alternatively, the one or more reactive components, either free in solution or bound to a solid substrate, can be released into the blood stream and allowed to bind one or more target cell types while in circulation. In this aspect, the one or more reactive components can be recaptured by the device wherein the treatment region has an increased affinity for the reactive component bound to the one or more target cell types and is configured to modulate the physiological effect of the one or more target cell types.

The one or more reactive components can be bound to the solid substrate either directly or indirectly. For example, the one or more reactive components can be coupled to the solid substrate by covalent chemical bonds between particular functional groups on the specific binding agent (e.g., primary amines, sulfhydryls, carboxylic acids, hydroxyls, and aldehydes) and reactive groups on the solid substrate. A variety of activating compounds and schemes for directly bonding ligands to solid substrates are known. Examples include, but are not limited to, cyanogen bromide, cyanuric chlorde, epichlorohydrin, divinyl sulphone, p-toluenesulphonyl chloride, 1,1'-carbonyldiimidazole, sodium meta-periodate, 2-fluro-1-methylpyridiniumtoluene-4-sulphonate, glycidoxypropyl-trimethoxysilane and 2,2,2-trifluroethanesulphonyl chloride. For example, cyanogen bromide in base reacts with hydroxyl (OH) groups on agarose solid substrate to form cyanate esters or imidocarbonates. These groups readily react with primary amines under mild conditions resulting in a covalent coupling of the ligand to the agarose solid substrate. Reactive imidocarbonates can also be formed on carbon nanotubes, for example, through reactive carboxyl groups generated by treatment of the nanotubes with oxidizing agents. See, e.g., Bianco, et al., in *Nanomaterials for Medical Diagnosis and Therapy*. pp. 85-142. Nanotechnologies for the Live Sciences Vol. 10 Edited by Challa S. S. R. Kumar, WILEY-VCH Verlag GmbH & Co. KGaA, Weinheim, 2007, which is incorporated herein by reference. Functionalization of silicon chips with carboxyl groups can be subsequently used to immobilize proteins in the presence of N-ethyl-N'-(3-dimethylaminopropyl)carbodiimide hydrochloride (EDC) and N-hydroxysuccinimide ester (NHS). See, e.g., Hu, et al., *Rapid Commun. Mass Spectrom.* 21:1277-1281, 2007, which is incorporated herein by reference.

The one or more reactive components may or may not have linking or spacer groups bound to the C-terminus which, when present, can be used to bind the specific binding agent to the solid substrate indirectly. When present, the linking group can be a polymer or a monomer. A linking group can be a chain of from 1-10 amino acids. Other examples of linking groups include, but are not limited to, polyethylene glycol, polypropylene glycol, polyesters, polypeptides, polyethers, polysaccharides, glycidoxyalkyl, alkoxyalkyl, alkyl, glycidoxypropyl, ethyl, propyl, phenyl and methacryl; and silicon containing linking groups such as diethyl(triethoxysilylpropyl)malonate; 3-mercaptopropyltrimethoxysilane; 3-aminopropyltrimethoxysilane; N-[(3-trimethoxysilyl)propyl]ethylenediaminetriacetic acid; p-(chloromethyl) phenyltrimethoxysilane; vinyltriethoxysilane; 3-bromopropyltriethoxysilane; and 3-glycidoxypropyltrimethoxysilane.

In general, any of a number of homobifunctional, heterofunctional, and/or photoreactive cross linking agents can be used to conjugate one or more reactive components to an appropriately derivatized substrate. Examples of homobifunctional cross linkers include, but are not limited to, primary amine/primary amine linkers such as BSOCES ((bis(2-[succinimidooxy-carbonyloxy]ethyl) sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2'pyridyldithio]-propionamido) butane). Examples of heterofunctional cross linkers include, but are not limited to, primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-gamma-maleimidobutyryl-oxysuccinimide ester), Sulfo GMBS (N-γ-maleimidobutyryloxysulfosuccinimide ester), EMCS (N-(epsilon-maleimidocaproyloxy) succinimide ester), Sulfo EMCS (N-(epsilon-maleimidocaproyloxy) sulfo succinimide), SIAB (N-succinimidyl(4-iodoacetyl)aminobenzoate), SMCC (succinimidyl 4-(N-maleimidomethyl) cyclohexane-1-carboxylate), SMPB (succinimidyl 4-(rho-maleimidophenyl)butyrate), Sulfo SIAB (N-sulfosuccinimidyl(4-iodoacetyl)aminobenzoate), Sulfo SMCC (sulfosuccinimidyl 4-(N-maleimidomethyl) cyclohexane-1-carboxylate), Sulfo SMPB (sulfosuccinimidyl 4-(rho-maleimidophenyl) butyrate), and MAL-PEG-NHS (maleimide PEG N-hydroxysuccinimide ester); sulfhydryl/hydroxyl linkers such as PMPI (N-rho-maleimidophenyl) isocyanate; sulfhydryl/carbohydrate linkers such as EMCH (N-(epsilon-maleimidocaproic acid) hydrazide); and amine/carboxyl linkers such as EDC (1-ethyl-3-(3-dimethylaminopropyl) carbodiimide hydrochloride).

In an aspect, the one or more reactive components can be linked to a solid substrate through non-covalent interactions. Examples of non-covalent interactions include, but are not limited to, protein-protein interactions such as those between avidin/streptavidin and biotin, protein A and immunoglobulins, protein G and immunoglobulins, or secondary antibodies with primary antibodies. For example, the one or more reactive components can be modified with biotin using standard methods and bound to a solid substrate derivatized with streptavidin. Alternatively, one or more reactive components can be modified with streptavidin and bound to a solid substrate derivatized with biotin. A single chain antibody can incorporate streptavidin as part of a fusion protein, to facilitate attachment of the antibody to the solid substrate via a biotin-streptavidin linkage. See, e.g., Koo, et al. *Appl. Environ. Microbiol.* 64:2497-2502, 1998, which is incorporated herein by reference, Solid substrates such as beads or other particulate substrates derivatized with protein A, protein G, streptavidin, avidin, biotin, secondary antibodies are available from commercial sources (from, e.g., Pierce-Thermo Scientific, Rockford, Ill., Sigma-Aldrich, St. Louis, Mo.). In an aspect, the one or more reactive components can bind to the solid substrate through a non-covalent interaction and be further cross-linked to the solid substrate using a cross-linking agent.

In an aspect, the one or more reactive components can be associated with a solid substrate that are cells, e.g., mammalian cells, enucleated erythrocytes, bacteria, or viral particles, or vesicles such as liposomes or other micellular vesicles. Cells and vesicles can be modified with one or more reactive components using many of the same methods as provided herein. One or more reactive components can be bound to cells or vesicles using one or more homobifunctional or heterofunctional cross-linkers through primary amines and carboxyl groups. Alternatively, cells can be modified with one or more reactive components using a biotin-streptavidin bridge. For example, one or more reactive components can be biotinylated and linked to a non-specifically biotinylated cell surface through a streptavidin bridge. An antibody, aptamer, or receptor can be biotinylated using standard procedures. The surface membrane proteins of a cell can be biotinylated using an amine reactive biotinylation reagent such as, for example, EZ-Link Sulfo-NHS-SS-Biotin (sulfosuccinimidyl 2-(biotinamido)-ethyl-1, 3-dithiopropionate; Pierce-Thermo Scientific, Rockford, Ill., USA; see, e.g., Jaiswal, et al. *Nature Biotech.* 21:47-51, 2003; U.S. Pat. No. 6,946,127).

In an aspect, the one or more reactive components can be associated with lipid or micellular vesicles. In an aspect, the one or more reactive components can be antibodies attached to a liposome. Antibodies can be added to liposomes using cross-linking agents and protein A. See, e.g., Renneisen, et al., *J. Biol. Chem.*, 265:16337-16342, 1990, which is incorporated herein by reference. The liposomes are formed from dry lipid in the presence of an aqueous solution, e.g., a buffer of appropriate pH followed by extrusion through a high pressure device fitted with a polycarbonate filter with the desired pore size to form liposomes of a specific size range. The liposomes are modified with N-succinimidyl 3-(2-pyridyldithio) propionate-modified protein A. The one or more antibodies are linked to the liposomes through selective binding to the protein A. Alternatively, thiolated antibodies can be covalently linked to liposomes prepared with 4-(p-maleimidophenyl) butyrylphosphatidyl-ethanolamine. See, e.g., Heath, et al., *PNAS* 80:1377-1381, 1983, which is incorporated herein by reference.

In an aspect, the one or more reactive components can be expressed on the surface of a cell. The one or more reactive components can be naturally expressed on the surface of a cell. Alternatively, the one or more reactive components can be expressed on the surface of a cell using genetic manipulation. For example, cells can be genetically manipulated to express a receptor that binds one or more target cell types. Alternatively, cells can be genetically manipulated to express one or more specific antibodies on the cell surface. Methods have been provided for cell surface expression of single chain Fv antibody fragments (scFv) fused to membrane-associated proteins. See, e.g., Ho, et al., *Proc. Natl. Acad. Sci. USA* 103:9637-9642, 2006; Francisco, et al., *Proc. Natl. Acad. Sci. USA* 90:10444-10448, 1993; U.S. Pat. Appl. No. 2006/0083716, which are incorporated herein by reference. In this aspect, the cDNA sequence encoding all or part of target cell-specific antibody is fused in an expression construct in frame with a membrane-associated protein and expressed in an appropriate cell type.

PROPHETIC EXAMPLES

Example 1

Device Including Sensor for Detecting One or More Target Inflammatory Cells and for Binding and Modulating the Physiological Effect of Inflammatory Cells for Treatment of an Inflammatory Condition or an Inflammatory Disease A device is described for treating an inflammatory condition or inflammatory disease associated with elevated levels of eosinophils in the blood fluid or lymph fluid of a vertebrate subject. The device includes one or more aptamer-based piezoelectric sensors to detect target eosinophils in peripheral blood fluid or lymph fluid of the vertebrate subject and a treatment region that includes anti-IL5 receptor antibodies that will bind to the eosinophil cell surface to sequester the eosinophils in the treatment region. The sequestered eosinophils are exposed to an ultraviolet energy source in the treatment region to reduce the number or activity of eosinophils in the blood fluid or lymph fluid of the subject. The sensor detects the presence of eosinophils by utilizing piezoelectric sensors in the sensor region. The device includes piezoelectric sensors that report to a controller to controls flow of the blood fluid or lymph fluid through a controllable flow barrier into one or more lumens toward the treatment region of the device. The controller acts upon the flow barrier into the lumen to open or close the flow barrier to allow access of the blood fluid or lymph fluid to the treatment region within the lumen. The controller responds to the sensor after the sensor detects elevated levels of eosinophils in the blood fluid or lymph fluid of the subject. The device includes anti-IL5 receptor antibodies for capturing eosinophils at elevated levels in blood fluid or lymph fluid flowing into the lumen and presenting the eosinophils to the treatment region of the device. The controller in communication with the sensor, adjusts access to the anti-IL5 receptor antibodies by controlling flow through the lumen or by controlling the presence of the anti-IL5 receptor antibodies on the surface of the treatment region thus controlling the activity of the anti-IL5 receptor antibodies in order to achieve a target value of the detected eosinophils in the blood fluid or lymph fluid of the vertebrate subject. The device optionally includes a receiver for receiving and processing data regarding the sensed levels of eosinophils and includes a transmitter for transmitting data to an external controller, a computing device, a physician, or a caregiver.

The device is placed in or proximal to one or more blood vessels or lymph vessels of the vertebrate subject. The device is a hollow stent-like structure that is placed into a vessel at or near a site of inflammation using a catheter guide wire. The components of the device, including piezoelectric sensors, controller, binding agents, and reactive components, are affixed to and/or incorporated into one or both surfaces of the stent-like structure. Depending upon the inflammatory state and level of eosinophils in the blood fluid or lymph fluid of the subject, the device is configured such that blood fluid or lymph fluid in the vessel is allowed to flow through the controllable flow barrier into the lumen depending on the signal from the controller either essentially unobstructed or limited by signaling from the controller to the flow barrier to partially or completely limit flow of blood fluid or lymph fluid through the lumen of the device.

The device includes one or more piezoelectric sensors that sense the levels of eosinophils in the blood fluid or lymph fluid of the vertebrate subject. The one or more piezoelectric sensors include aptamers as recognition elements to detect surface components of the eosinophils. The interaction of eosinophils with the aptamer recognition elements triggers the piezoelectric sensor to send a signal to the controller. The one or more piezoelectric sensors are operably coupled to the controller, either wirelessly or by circuit, and can transmit data to the controller regarding the detection and/or levels (relative or absolute) of eosinophils in the blood fluid or lymph fluid of the subject. The controller is an integral component of the device. The controller controls an energy source, e.g., controllable ultraviolet energy source, directed against the bound eosinophils. The controller includes access to stored data, or data that is stored off-site, and is coupled either wirelessly or by circuit to the piezoelectric sensor and the controller. The controller also has access to one or more remote databases that include the stored data. The stored data includes data regarding the normal level of eosinophils in normal or healthy subjects without an inflammatory disease or condition. The stored data includes data regarding the baseline level of eosinophils in a subject prior to onset of the inflammatory disease or condition. The stored data also includes data regarding the level of eosinophils in a subject at one or more previous time points. The controller calculates the levels of eosinophils in the blood fluid or lymph fluid based on the input from the sensors and compares these data with target values, e.g., desired concentrations of eosinophils. For example, the number of eosinophils in a normal human subject ranges from about 45 cells/microliter to about 450 cells/microliter. By contrast, a human subject experiencing hypereosinophilic syndrome (HES) has more than 1500 eosinophils/microliter. See, e.g., Roufosse, *Haematologica* 94:1188-1193, 2009, which is incorporated herein by reference. In some instances, the target value for eosinophils is that observed in a normal subject not experiencing an inflammatory disease or a disease resulting in an inflammatory response. In other instances, the target value for eosinophils represents a reduction of at least 60% relative to the current level of eosinophils in the blood fluid or lymph fluid of the subject. The controller sends a wireless signal to an external controller to alert the subject and/or one or more caregivers as to the levels of eosinophils in the blood fluid or lymph fluid of the subject.

The device includes one or more binding agents for capturing the eosinophils within the treatment region of the device. The binding agent is an antibody directed against the eosinophil cell surface IL-5 receptor. IL-5 receptor is upregulated on activated eosinophils and contributes to an allergic reaction in the vertebrate subject. Antibodies to the IL-5 receptor are available from commercial sources (from, e.g., Sigma-Aldrich, St. Louis, Mo.; or R&D Systems, Inc., Minneapolis, Minn.) or are readily generated using standard methods. See, e.g., Harlow & Lane *Antibodies: A Laboratory Manual*, Cold Spring Harbor Laboratory Press; 1$^{st}$ edition 1988, which is incorporated herein by reference. The antibodies directed against eosinophil cell surface IL-5 receptor are incorporated within the lumen of the stent-like structure of the device at one or more sites to maximize exposure of the antibody binding components to eosinophils in the blood fluid or lymph fluid of the vertebrate subject. Protocols are provided for chemically linking an antibody to a collagen-coated stent using N-succinimidyl-3-(2-pyridyldithiol)-propionate as a cross-linker. See, e.g., Jin, et al., *J. Gene Med.* 8:786-793, 2008, which is incorporated herein by reference.

The device further includes one or more reactive components designed to reduce or eliminate a physiological activity of one or more IL-5 receptor-bound eosinophils, and to reduce the number or activity of eosinophils in the blood fluid or lymph fluid of the subject to achieve the desired target values thus reducing an inflammatory disease in the subject. In an aspect, the reactive component is the specific binding agent capable of directly modulating a physiological effect of the eosinophils in the blood. The binding agent, anti-IL5 receptor antibodies directed against eosinophil cell surface IL-5 receptor, have an intrinsic catalytic activity triggered by a controllable energy source. In response to ultraviolet energy released by the device within the treatment region, the eosinophil cell surface IL-5 receptor binding agent antibodies produce reactive oxygen species that modulate, reduce, or eliminate the biological activity of the eosinophils. The release of ultraviolet energy in the treatment region is triggered by the controller based on the sensed levels of eosinophils in the blood fluid or lymph fluid. In the absence of a triggering event by a controllable ultraviolet energy source, the controller signals that a target level of eosinophils has been reached, and the eosinophils bound to the anti-IL5 receptor antibodies will eventually dissociate and return to the blood fluid or lymph fluid of the subject.

Example 2

Device Including Sensor for Detecting One or More Target Circulating Lung Tumor Cells and for Binding and Modulating the Physiological Effect of Circulating Lung Tumor Cells for Treatment of a Neoplastic Disease or Condition A device is described for treating a neoplastic disease or condition including one or more light-scattering sensors to sense one or more circulating metastatic lung tumor cells in blood fluid or lymph fluid of a subject, and a controller that controls flow of the blood fluid or lymph fluid through a lumen of the device to a treatment region in response to the sensor. The device is placed in or proximal to one or more blood vessels of a subject with metastatic lung cancer and includes a treatment region that receives at least a portion of the blood through a flow route, and the controller to control flow of blood through a controllable flow barrier into the flow route to the treatment region. The treatment region includes a binding agent specific for circulating lung tumor cells and used to sequester the lung tumor cell within the treatment region. The binding agent is an antibody configured to selectively bind an epithelial cell-specific antigen, epithelial cell-cell adhesion molecule (EpCAM), to detect metastatic lung tumor cells. The treatment region further includes one or more reactive components, such as high concentrations of one or more cytotoxic chemotherapeutic agents to cause necrosis or apoptosis of the circulating lung tumor cells in the blood. The one or more reactive components include localized high concentrations of a chemotherapy regimen within the vicinity of the treatment region. The reservoirs within the treatment region release the components of an AT chemotherapy regimen: doxorubicin, either alone or in combination with paclitaxel. The device includes a transmitter configured to transmit the sensed levels of one or more circulating lung tumor cells to an external controller.

The device includes one or more light-scattering sensors that sense the levels of one or more circulating lung tumor cells in the blood of a subject. A light source in the device provides differential light scattering to detect circulating lung tumor cells derived from metastases of solid tumors. In general, a circulating tumor cell is characterized by its large size, immature appearance, increased nuclear to cytoplasmic ratio, abnormally shaped nuclei, and disproportionately large nucleolus or multiple nucleoli. The size differential between a circulating tumor cell and components of the blood may be used to specifically detect the cancerous cells. For example, the average diameter of neutrophils, red bloods cells, and platelets is 10.5-12.5 microns, 7-8 microns, and 3 microns, respectively. In contrast, the average size of circulating tumor cells isolated from subjects with breast, colon, stomach and lung cancers range from 18.3 to 20.6 microns in diameter. Circulating neuroblastoma tumor cells, for example, are greater than 20 microns in diameter. See, e.g., Moore et al. *Cancer* 13:111-117, 1960; Mohamed et al. *IEEE Transactions on Nanobioscience,* 3:251-256, 2004, each of which is incorporated herein by reference. The size of a cell or cells passing by the one or more sensors is determined using forward and side light scattering. The size, as measured in diameter, is compared with known parameters regarding the size of normal blood components.

The controller, in communication with the sensor, adjusts access to the treatment region and the chemotherapeutic agents by controlling flow of blood fluid or lymph fluid through the controllable flow barrier into the one or more lumens of the device or by controlling the presence of the chemotherapeutic agents on the surface of the reaction region thus controlling the activity of the chemotherapeutic agents to achieve a target value of the detected metastatic lung tumor cells in the blood fluid or lymph fluid of the vertebrate subject. The controller calculates the number of metastatic lung tumor cells in the peripheral blood fluid or lymph fluid based on the input from the sensors and compares these data with target values, e.g., reduced concentrations of metastatic lung tumor cells to a target value of zero lung tumor cells in the peripheral blood fluid or lymph fluid. However, in some instances, simply lowering the number of circulating lung tumor cells may improve prognosis. For example, breast cancer patients with levels of circulating tumor cells equal to or higher than five cells per 7.5 milliliters of blood have a shorter median progression-free survival (2.7 months vs. 7.0 months) and shorter overall survival (10.1 months versus greater than 18.0 months) as compared with breast cancer patients with less than five cells per 7.5 milliliters of blood. See, Cristofanilli et al. *N. Engl. J. Med.* 351:781-791, 2004, which is incorporated herein by reference. The target value for circulating lung tumor cells may represent a reduction of at least 60% relative to the current level of circulating lung tumor cells in the peripheral blood of the subject. The device includes a receiver for receiving and processing data regarding the sensed levels of metastatic lung tumor cells and a transmitter for transmitting data to an external controller, a computing device, a physician, or a caregiver.

Detection by the one or more light-scattering sensors of an abnormally large cell signals to the detector the presence of a circulating lung tumor cell and triggers a response from the controller to divert all or part of the blood flow through the controllable flow barrier into one or more treatment regions of the device. The data regarding the current concentration of circulating lung tumor cells can also be compared with data points collected previously in time to assess either disease progression and/or treatment efficacy. The controller sends a wireless signal to an external controller to alert the subject and/or one or more caregivers as to the levels of circulating lung tumor cells in the peripheral blood of the subject.

The controller is an integral component of the device. The controller includes access to stored data, or data that is stored off-site and coupled either wirelessly or by circuit to the sensor. The controller also has access to one or more remote databases that include the stored data. The stored data includes data regarding the historic level of lung tumor cells in the subject with lung cancer. The stored data includes data regarding the baseline level of lung tumor cells in the subject prior to onset of the neoplastic disease. The stored data also includes data regarding the level of lung tumor cells in the subject at one or more time points during progression of lung cancer. The controller calculates the levels of lung tumor cells in the blood fluid or lymph fluid based on the input from the sensors and compares these data with target values, e.g., reduced levels of lung tumor cells. The controller controls flow of the peripheral blood into the treatment region. The treatment region includes one or more binding agents that specifically bind metastatic lung tumor cells. The binding agent is an antibody configured to selectively bind an epithelial cell-specific antigen, epithelial cell-cell adhesion molecule (EpCAM), which is an epithelial cell-specific antigen on a surface of metastatic lung tumor cells. See, e.g., Fizazi, et al., *Ann. Oncol.* 18: 518-521, 2007, which is incorporated herein by reference. Antibodies directed against EpCAM, e.g., Ber-EP4, MOC31, and VU-1D9, are commercially available from, e.g., Abcam Inc., Cambridge, Mass., or are generated using standard methods. See, e.g., Harlow & Lane, *Antibodies: A Laboratory Manual*, Cold Spring Harbor Laboratory Press; $1^{st}$ edition 1988, which is incorporated herein by reference. The anti-EpCAM antibody is used to coat one or more surfaces of the treatment region and is attached to the surface using any of a number of heterofunctional crosslinking agents. A silicon chip-like surface is functionalized with carboxyl groups and subsequently used to immobilize proteins, e.g., antibodies, in the presence of N-ethyl-N'-(3-dimethylaminopropyl)carbodiimide hydrochloride (EDC) and N-hydroxysuccinimide ester (NHS). See, e.g., Hu, et al., *Rapid Commun. Mass Spectrom.* 21: 1277-1281, 2007, which is incorporated herein by reference. Alternatively, the antibody against EpCAM is used to coat one or more particles such as, magnetic beads. See, e.g., Flatmark, et al., *Clin. Canc. Res.* 8: 444-449, 2002, which is incorporated herein by reference. The particles coated with an anti-EpCAM metastatic lung tumor cell specific antibody are retained in the treatment region due to either size exclusion or magnetic properties.

The controller controls flow of the blood in the subject into the one or more treatment regions of the device. The circulating lung tumor cells present in the peripheral blood bind to the anti-EpCAM antibody in the treatment region. Once sequestered in the treatment region, the circulating lung tumor cells are further subjected to one or more reactive components, e.g., cytotoxic chemotherapeutic agents, to induce cell-disruption, apoptosis, and or death of the lung tumor cells. The one or more treatment regions further include one or more reservoirs configured to release localized high concentrations of one or more cytotoxic agent. The reservoirs within the treatment region can release the components of an AT chemotherapy regimen: chemotherapeutic agent doxorubicin (Adriamycin®) either alone or in combination with paclitaxel (Taxol®), resulting in apoptosis or necrosis of the lung tumor cells. The controller in the device maintains blood flow through the controllable flow barrier into the treatment region until target levels of circulating lung tumor cells are reached in the blood fluid or lymph fluid of the subject.

Example 3

Device Including Sensor for Detecting One or More Red Blood Cells Infected with *Plasmodium* and for Binding and Modulating the Physiological Effect of Red Blood Cells Infected with *Plasmodium* for Treatment of Malaria A device is described for treating malaria including one or more aptamer-based fluorescent molecular beacon sensors configured to sense one or more *Plasmodium*-infected red blood cells in peripheral blood of a mammalian subject, a controller configured to control flow of the peripheral blood through a controllable flow barrier into one or more lumens in response to the sensor and one or more reactive components including a magnetic component to trap the paramagnetic *Plasmodium*-infected red blood cells and a cytotoxic agent to induce apoptosis or necrosis in *Plasmodium*-infected red blood cells. The device includes a controller to achieve a desired target value of *Plasmodium*-infected red blood cells. The device is placed in or proximal to one or more blood vessels of a subject and includes one or more aptamer-based molecular beacon sensors for sensing *Plasmodium*-infected red blood cells and a controller to receive data regarding the sensed levels of *Plasmodium*-infected red blood cells. The device includes one or more lumens through which blood is controllably diverted based on the sensed levels of *Plasmodium*-infected red blood cells, and one or more reservoirs within the lumens containing one or more cytotoxic agents to disrupt the *Plasmodium*-infected red blood cells. The reactive components include a magnetic component to trap the paramagnetic *Plasmodium*-infected red blood cells and a cytotoxic agent to induce apoptosis or necrosis in *Plasmodium*-infected red blood cells. The reactive components are contained in one or more reservoirs controllably opened or closed by the controller. The controller in communication with the sensor, adjusts access to the magnetic component trap and the cytotoxic agent by controlling flow through the lumen or by controlling the presence of the cytotoxic agents released from or on the surface of the reaction region thus controlling the activity of the cytotoxic agents in order to achieve a target value of the detected *Plasmodium*-infected red blood cells in the blood of the subject. The device optionally can include a receiver for receiving and processing data regarding the sensed levels of *Plasmodium*-infected red blood cells and a transmitter for transmitting data to an external controller, a computing device, a physician, or a caregiver.

The device includes sensors that sense the levels of one or more *Plasmodium*-infected red blood cell. The sensors are aptamer-based molecular beacons designed to fluoresce in response to selectively binding the one or more *Plasmodium*-infected red blood cell. The aptamer is configured to selectively bind the *Plasmodium falciparum* derived erythrocyte membrane protein (PfEMP) expressed on the surface of *Plasmodium*-infected red blood cell. One or more aptamers directed against PfEMP are generated using Systemic Evolution of Ligand by Exponential enrichment (SELEX) as described in Barfod, et al., *Parasitol. Res.* 105: 1557-1566, 2009, which is incorporated herein by reference. The aptamer-based molecular beacon includes a recognition element and at least one fluorescing moiety e.g., AF 647 (Molecular Probes—Invitrogen, Carlsbad, Calif.) and at least one quenching moiety, e.g., QSY 21 (Molecular Probes—Invitrogen, Carlsbad, Calif.). The recognition element generated by SELEX selectively interacts with *Plasmodium*-infected red blood cells. The interaction of the *Plasmodium*-infected red blood cells with the aptamer can be monitored using fluorescence resonance energy transfer (FRET). The aptamer-based molecular beacon is configured such that binding *Plasmodium*-infected red blood cells to the aptamer induces a conformational change in the aptamer and increases the distance between the fluorescing moiety and the quenching moiety resulting in a fluorescent signal in response to electromagnetic energy. The level of fluorescent signal is proportional to the level of *Plasmodium*-infected red blood cells in the blood sample. The emitted fluorescence is captured by a CCD detector, CMOS detector, or other light capture device as part of the sensor, and a corresponding signal is sent to the controller.

The controller calculates the levels of *Plasmodium*-infected red blood cells in the blood of the subject based on the input from the sensors and compares these data with target values, e.g., desired concentrations of target cell types. For malarial disease, the target value of *Plasmodium*-infected red blood cells is ideally zero. However, in some instances, simply lowering the number of *Plasmodium*-infected red blood cells may improve prognosis for malarial disease. The target value for *Plasmodium*-infected red blood cells may represent a reduction of at least 60% or at least 80% relative to the current level of *Plasmodium*-infected red blood cells in the peripheral blood of the subject.

Detection by the one or more aptamer-based molecular beacon sensors of *Plasmodium*-infected red blood cells in the peripheral blood of a subject triggers a response from the controller to divert all or part of the blood flow into one or more treatment regions of the device. The data regarding the current concentration of *Plasmodium*-infected red blood cells is also compared with data point collected previously in time to assess either disease progression and/or treatment efficacy. The controller optionally sends a wireless signal to an external controller to alert the subject and/or one or more caregivers as to the levels of *Plasmodium*-infected red blood cells in the peripheral blood of the subject.

The controller controls flow of the peripheral blood through the flow barrier into one or more lumens based on the sensed levels of *Plasmodium*-infected red blood cells in the blood of the subject. The sensor is operably coupled to the controller, either wirelessly or by circuit, and can transmit data to the controller regarding the detection and/or levels (relative or absolute) of *Plasmodium*-infected red blood cells in the blood of the subject. The controller is an integral component of the device. The controller controls one or more energy sources, e.g., one or more magnetic components, directed against the *Plasmodium*-infected red blood cells. The controller includes access to stored data, or data that is stored off-site and coupled either wirelessly or by circuit to the sensor and the controller. The controller also has access to one or more remote databases that include the stored data. The stored data includes data regarding the normal level of *Plasmodium*-infected red blood cells in normal or healthy subjects without malarial disease. The stored data includes data regarding the baseline level of *Plasmodium*-infected red blood cells in a subject prior to onset of malaria. The stored data also includes data regarding the level of *Plasmodium*-infected red blood cells in a subject at one or more previous time points. The blood of the subject flows into the lumen which includes one or more treatment regions. The treatment regions include one or more magnetic components configured to trap one or more *Plasmodium*-infected red blood cells in the treatment region based on the magnetic properties of the *Plasmodium*-infected red blood cells. Upon infecting red blood cells, *Plasmodium* species degrade the endogenous hemoglobin (an Fe(II) diamagnetic complex) into hemozoin (an Fe(III) paramagnetic complex). The *Plasmodium*-infected red blood cells become paramagnetic and are readily purified away from non-infected cells by magnetic separation. See, e.g., Ribaut, et al., *Malaria J.* 7: 45, 2008, which is incorporated herein by reference.

The controller controls flow of the peripheral blood into the one or more treatment regions of the device. *Plasmodium*-infected red blood cells are selectively retained in treatment regions containing one or more magnetic components. Once sequestered in the treatment region, the *Plasmodium*-infected red blood cells are subjected to one or more reactive components to induce cell-disruption, apoptosis, and or death of the *Plasmodium*-infected red blood cells. The one or more treatment regions include reservoirs configured to release localized high concentrations of one or more cytotoxic agents, e.g., anti-malarial agents, such as quinine, chloroquine, pyrimethamine, sulphadoxine, proguanil, and/or artemesinin configured to disrupt and kill *Plasmodium falciparum*.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will recognize that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if a surgeon determines that speed and accuracy are paramount, the implementer may opt for a mainly hardware and/or firmware vehicle; alternatively, if flexibility is paramount, the implementer may opt for a mainly software implementation; or, yet again alternatively, the surgeon may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In a general sense the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating a neoplastic disease or a neoplastic condition in a vertebrate subject comprising:
providing an implantable device comprising: a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor.

2. The method of claim 1, wherein the at least one treatment region including the one or more reactive components is configured to receive the one or more target cell types, and the one or more reactive components are configured to bind to the one or more target cell types at a surface of the at least one treatment region.

3. The method of claim 1, wherein the one or more reactive components include one or more of a cell-disrupting agent, a binding agent, or an energy source.

4. The method of claim 3, wherein the cell-disrupting agent includes a denaturing agent or a degradative agent.

5. The method of claim 1, wherein the one or more reactive components include a cytotoxic agent, a cytostatic agent, a programmed cell death-inducing agent, a chemotherapeutic agent, or an antibody-toxin agent.

6. The method of claim 1, wherein the one or more reactive components is configured to alter, arrest, or destroy the one or more target cell types.

7. The method of claim 6, wherein the one or more reactive components is configured to produce necrosis or programmed cell death in the one or more target cell types.

8. The method of claim 1, wherein the at least one treatment region is configured to be placed relative to a tumor or an organ in the vertebrate subject.

9. The method of claim 1, wherein the binding agents include one or more of an adhesion molecule, antibody, binding mimetic, polymer, lectin, integrin, or selectin.

10. The method of claim 1, wherein the at least one lumen is configured for fluid flow including the one or more target cell types.

11. The method of claim 1, wherein the one or more sensor is configured to detect the one or more target cell types within the at least one lumen.

12. The method of claim 1, wherein the one or more sensor is configured to detect the one or more target cell types in the at least one treatment region.

13. The method of claim 1, wherein the one or more sensor is configured to detect the one or more target cell types after the one or more target cell types has passed through the at least one lumen or the at least one treatment region.

14. The method of claim 1, wherein the at least one controller is configured to return flow from the at least one lumen to a blood vessel or a lymph vessel.

15. The method of claim 1, wherein the at least one lumen is configured for extended residence time of the blood fluid or the lymph fluid.

16. The method of claim 1, wherein the one or more sensor is external to the at least one lumen.

17. The method of claim 1, wherein the one or more sensor is internal to the at least one lumen.

18. The method of claim 1, further including a transmitter to report to the one or more sensor.

19. The method of claim 1, wherein the sensor is configured to report to an outside source or to a computing device.

20. The method of claim 1, wherein the fluid includes blood or lymph.

21. The method of claim 1, wherein the at least one controller includes a processor.

22. The method of claim 1, wherein the at least one controller is further configured to control interaction between the one or more reactive components and the one or more target cell types.

23. The method of claim 22, further including one or more reservoirs responsive to the controller, wherein the one or more reservoirs is configured to provide the one or more reactive components, and the one or more reservoirs is configured to function in, or proximal to, one or more of a blood vessel or a lymph vessel of the vertebrate subject.

24. The method of claim 1, wherein the one or more sensor is configured to function in, or proximal to, one or more of a blood vessel or a lymph vessel of the vertebrate subject.

25. The method of claim 3, wherein the binding agents include one or more of antibodies, receptors, or cognates configured to bind to at least one of the one or more target cell types.

26. The method of claim 3, wherein the binding agents include one or more energy absorbers designed to absorb energy from the energy source.

27. The method of claim 1, further including two or more parallel lumen configured to receive the one or more target cell types.

28. The method of claim 27, wherein a diameter of each of the two or more lumens are approximately less than two cell diameters.

29. The method of claim 1, wherein the at least one controller is configured to open or close the at least one controllable flow barrier in response to the one or more sensor to achieve a target level of the one or more target cell types in the vertebrate subject.

30. The method of claim 29, wherein the target level includes a desired concentration of the one or more target cell types in the one or more of the blood fluid or lymph fluid.

31. The method of claim 29, wherein the target level includes a desired range of concentrations of the one or more target cell types in the one or more of the blood fluid or lymph fluid.

32. The method of claim 29, wherein the target level includes a desired ratio of concentrations of two or more target cell types in the one or more of the blood fluid or lymph fluid.

33. The method of claim 29, wherein the target level includes a desired ratio of levels of two or more target cell types in the one or more of the blood fluid or lymph fluid.

34. The method of claim 29, wherein the one or more sensor and the at least one controller are configured to control levels of the detected one or more target cell types to limit a deviation from the target level.

35. The method of claim 1, wherein the at least one controller is configured to control release of the one or more reactive components.

36. The method of claim 34, wherein the deviation is determined by a weighted least squares fit.

37. The method of claim 1, wherein the one or more sensor includes a biosensor, chemical sensor, physical sensor, or optical sensor.

38. The method of claim 37, wherein the one or more sensor includes one or more of target recognition elements.

39. The method of claim 1, wherein the sensor is configured to target the device to a site having an elevated level of the target cell types.

40. The method of claim 1, wherein the sensor is configured to report to an outside source or to a computing device, and wherein the sensor is configured to report a level of the one or more target cell types.

41. The method of claim 1, wherein the at least one treatment region includes a matrix configured to present the one or more reactive components.

42. The method of claim 3, wherein the binding agents include one or more target recognition elements.

43. The method of claim 3, wherein the binding agent includes one or more of a specific binding ligand or a hydrophobic surface.

44. The method of claim 3, wherein the energy source includes acoustic energy or electronic energy.

45. The method of claim 44, wherein the energy source includes ultrasound.

46. The method of claim 1, wherein the at least one treatment region includes a source for producing the one or more reactive components.

47. The method of claim 1, wherein the at least one treatment region includes one or more reservoirs including the one or more reactive components.

48. The method of claim 46, wherein the source includes at least one reservoir and at least one producer.

49. The method of claim 46, wherein the source includes at least one encapsulated cell.

50. The method of claim 49, wherein the at least one encapsulated cell includes at least one genetically-engineered cell.

51. The method of claim 1, wherein the one or more target cell types is one or more of circulating cells or circulating emboli.

52. The method of claim 1, wherein the device is intracorporeal.

53. The method of claim 52, wherein the device is configured to be implanted relative to an organ or tissue in the vertebrate subject.

54. The method of claim 52, wherein the device is configured to be mobile relative to an organ or tissue in the vertebrate subject.

55. A method for modulating a neoplastic disease or a neoplastic condition in a vertebrate subject comprising:
providing an implantable device comprising: a body defining at least one lumen configured for fluid flow; at least one controllable flow barrier to the at least one lumen; one or more sensor configured to detect one or more target cell types in blood fluid or lymph fluid of a vertebrate subject; at least one treatment region disposed within the at least one lumen; at least one reactive component disposed in the at least one treatment region, the at least one reactive component configured to modulate the physiological effect of the one or more target cell types in the vertebrate subject; and at least one controller in communication with the one or more sensor and in communication with the at least one controllable flow barrier to the at least one lumen; wherein the at least one controller is configured to open or close the at least one controllable flow barrier in response to the one or more sensor.

* * * * *